United States Patent
Keyak et al.

(10) Patent No.: US 9,597,427 B2
(45) Date of Patent: *Mar. 21, 2017

(54) RADIOACTIVE BONE CEMENT

(71) Applicant: The Regents of the University of California, Oakland, CA (US)

(72) Inventors: Joyce H. Keyak, Orange, CA (US); Tadashi Kaneko, Irvine, CA (US); Harry B. Skinner, Corona del Mar, CA (US); Varun Sehgal, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/938,708

(22) Filed: Nov. 11, 2015

(65) Prior Publication Data

US 2016/0058905 A1 Mar. 3, 2016

Related U.S. Application Data

(63) Continuation of application No. 13/403,915, filed on Feb. 23, 2012, now Pat. No. 9,198,989.
(Continued)

(51) Int. Cl.
*A61L 24/00* (2006.01)
*A61K 51/12* (2006.01)
*A61N 5/10* (2006.01)

(52) U.S. Cl.
CPC ...... *A61L 24/0015* (2013.01); *A61K 51/1279* (2013.01); *A61L 2300/44* (2013.01); *A61N 5/1014* (2013.01)

(58) Field of Classification Search
CPC .......................... A61N 5/1014; A61K 51/1279
See application file for complete search history.

(56) References Cited

U.S. PATENT DOCUMENTS 5,275,610 A 1/1994 Eberbach
5,342,283 A 8/1994 Good
(Continued)

OTHER PUBLICATIONS

Sadeghi, M., et al., "Dosimetry of 32P radiocolloid for treatment of cystic craniopharyngioma", J. Applied Radiation and Isotopes 65: 519-23 (2007).
(Continued)

*Primary Examiner* — Christine H Matthews
*Assistant Examiner* — Joshua D Lannu
(74) *Attorney, Agent, or Firm* — Nathan S. Smith; Mark B. Bentley; McDermott Will & Emery LLP

(57) ABSTRACT

A target tissue can be treated with a radioisotope. Some methods for treating a target tissue with a radioisotope include determining a distance between a target tissue and a surface of a matrix material to be positioned adjacent the target tissue and, based on the determined distance, determining an activity to be mixed with the matrix material to obtain a desired activity concentration. Some methods further include mixing the radioisotope with the matrix material. In some embodiments, the matrix material comprises bone cement, and the target tissue is a tumor in a bone. The radioisotope may be a beta-emitting radioisotope mixed in the cement at a concentration to form a radioactive cement.

21 Claims, 33 Drawing Sheets

Related U.S. Application Data

(60) Provisional application No. 61/445,959, filed on Feb. 23, 2011.

(56) References Cited

U.S. PATENT DOCUMENTS

| | | | |
|---|---|---|---|
| 5,591,170 | A | 1/1997 | Spievack et al. |
| 5,601,572 | A | 2/1997 | Middleman et al. |
| 5,672,173 | A | 9/1997 | Gough et al. |
| 5,678,572 | A | 10/1997 | Shaw et al. |
| 5,709,697 | A | 1/1998 | Ratcliff et al. |
| 5,797,958 | A | 8/1998 | Yoon |
| 5,904,690 | A | 5/1999 | Middleman et al. |
| 6,152,894 | A | 11/2000 | Kubler |
| 6,814,712 | B1 | 11/2004 | Edwards et al. |
| 7,025,768 | B2 | 4/2006 | Elliott |
| 7,513,679 | B2 | 4/2009 | Grebius |
| 7,524,103 | B2 | 4/2009 | McGill et al. |
| 7,524,318 | B2 | 4/2009 | Young et al. |
| 7,713,270 | B2 | 5/2010 | Suzuki |
| 8,221,425 | B2 | 7/2012 | Arcenio et al. |
| 9,198,989 | B2 | 12/2015 | Keyak et al. |
| 2002/0058850 | A1 | 5/2002 | Rosenthal et al. |
| 2003/0009172 | A1 | 1/2003 | Bonutti |
| 2003/0097134 | A1 | 5/2003 | Kunzler |
| 2004/0267269 | A1 | 12/2004 | Middleton et al. |
| 2006/0116690 | A1 | 6/2006 | Pagano |
| 2006/0216230 | A1* | 9/2006 | Keyak ............... A61K 51/12 424/1.11 |
| 2006/0264967 | A1 | 11/2006 | Ferreyro et al. |
| 2007/0123907 | A1 | 5/2007 | Weber |
| 2007/0219549 | A1 | 9/2007 | Marshall et al. |
| 2008/0039880 | A1 | 2/2008 | Nohilly et al. |
| 2008/0114364 | A1 | 5/2008 | Goldin et al. |
| 2008/0249552 | A1 | 10/2008 | Eliachar et al. |
| 2008/0255597 | A1 | 10/2008 | Pravong et al. |
| 2008/0262525 | A1 | 10/2008 | Chang et al. |
| 2010/0249785 | A1 | 9/2010 | Betts |
| 2011/0004210 | A1 | 1/2011 | Johnson et al. |

OTHER PUBLICATIONS

Tassan, V., et al., "Phosphorous-32 Therapy of Cystic Grade IV Astrocytomas: Technique and Preliminary Application", J. Nucl Med. 26:1335-8 (1985).

McGuire, E.L., et al., "Radiation dosimetry considerations in the treatment of cystic suprasselar neoplasms", The British Journal of Radiology, 59:779-85 (1986).

Rojas, E.L., et al., "Dosimetry for radiocolloid therapy of cystic craniopharyngiomas", Med. Phys. 30:24822-*, (2003).

Harbert, "Radiocolloid Therapy of Cystic Craniopharyngiomas", Nuclear Medicine Therapy, Chapter 9 (1987).

* cited by examiner

RADIOACTIVE BONE CEMENT

RELATED APPLICATION

This application is a continuation of U.S. application Ser. No. 13/403,915, filed Feb. 23, 2012, which claims priority benefit under 35 U.S.C. 119(e) from U.S. Provisional Application No. 61/445,959, filed Feb. 23, 2011, the entirety of each of the above applications is incorporated by reference herein.

GOVERNMENT LICENSE RIGHTS

This invention was made with Government support under Grant No. W81XWH-07-1-0397, awarded by the ARMY. The Government has certain rights in this invention.

BACKGROUND

Spinal metastases are a common manifestation of many types of cancer. Specifically, metastatic lesions in the spine have been found in 90.5%, 74.3% and 45% of patients who died from prostate, breast and lung cancer, respectively. Additionally, approximately 200,000 patients die with metastatic lesions in their spine each year in the United States alone. Vertebral metastases cause pain, can degrade bone strength, and, due to the proximity of the spinal cord, can lead to serious neurological complications resulting from vertebral collapse. Treatment must address the tumor itself as well as the structural deficiency it may cause in the bone. The conventional treatment often occurs in two steps—a surgical procedure in which polymethylmethacrylate (PMMA) bone cement is injected into the vertebral body to restore strength to the bone (vertebroplasty or kyphoplasty), followed by multiple daily radiotherapy sessions to control tumor growth. The most common type of radiotherapy for spinal metastases is external beam radiation therapy (EBRT). Although EBRT effectively delivers radiation to the vertebral body, adjacent radiosensitive tissues such as the spinal cord and nerves are also irradiated, often limiting the dose that can be safely delivered to the tumor. Thus, to maximize treatment effectiveness while minimizing collateral damage to normal tissue, EBRT is fractionated into ten daily treatment sessions, inconveniencing patients whose quality of life has already been compromised. Intensity modulated radiation therapy (IMRT) and stereotactic body radiation therapy (SBRT) have emerged as improved radiotherapy techniques, but both techniques still require multiple treatment sessions, still irradiate the spinal cord and nerves (albeit to a lesser extent), and are expensive.

The use of vertebroplasty and kyphoplasty is likely to increase, as both procedures can provide immediate pain relief and patients with metastatic bone disease are living longer. However, conventional radiation therapy modalities can be inconvenient for the patient, as they are performed separately from the surgical procedure and are usually fractionated into multiple treatment sessions to minimize the collateral damage to normal tissue that occurs when radiation is delivered using an external irradiation source. Although radiotherapy can be given in fewer fractions with similar pain relief, patients treated with a single fraction tend to require retreatment more often than patients treated with multiple fractions.

SUMMARY

Described herein are methods for treating a target tissue with a radioisotope that include determining a distance between a target tissue and a surface of a matrix material to be positioned adjacent the target tissue and, based on the determined distance, determining an activity to be mixed with the matrix material to obtain a desired activity concentration. Some methods further include mixing the radioisotope with the matrix material. In some methods, the surface comprises a closest surface of the matrix material to the target tissue. In some methods, the closest surface may be a point on the surface or a small region about the point that is the minimum distance to the target tissue. The matrix material may be a bone cement. The target tissue may be a bone tumor. As used herein, a "bone tumor" or "a tumor in a bone" may include a primary tumor, a secondary tumor, or the presence of both in a bone.

Some methods are described herein for determining an activity concentration of a radioisotope for treating a target tissue in a vertebra. Some methods include, based on (a) a distance between the target tissue and a surface of a matrix mixture, and (b) a dose to be delivered to the target tissue, determining, by a processor, an activity concentration of the radioisotope to be combined with the matrix material to form the mixture. In some methods, the mixture is configured such that when placed in the vertebra and when a closest surface of the mixture is at the distance away from the target tissue, the mixture delivers substantially the dose to the target tissue independently of a total volume of the mixture placed in the vertebra. In certain methods, when the distance is about 3.4 mm, emissions from the radioisotope reaching the target tissue are emitted from substantially only within about 1.0 mm to about 2.5 mm of the closest surface.

Some methods for treating a bone tumor of a patient include determining a distance between the bone tumor and volume of bone cement to be positioned within the patient and, based on at least one dose-to-depth parameter for a radioisotope, determining an activity concentration of a radioactive material to deliver radiation to the bone tumor. In some methods, the tumor resides at the distance from an edge of the volume of bone cement. Some methods further include outputting the activity concentration to a nontransitory computer-readable medium. In some methods, the edge comprises a closest edge of the matrix material to the target tissue.

Some methods for limiting radiation damage while treating a target with a radioisotope described herein include determining a distance between (a) a tissue to be spared radiation damage and (b) a surface of a bone cement to be positioned near the target; based on the determined distance and based on a maximal dose of radiation to the tissue, determining an activity of the radioisotope to be mixed with the bone cement to obtain an activity concentration that limits a dose of radiation to the tissue to less than the maximal dose; and mixing the radioisotope with the bone cement.

Some methods for treating a bone tumor of a patient include the step of, based on (i) a distance between the bone tumor and volume of bone cement to be positioned within the patient, and (ii) at least one dose-to-depth parameter for a radioisotope, determining an activity concentration of a radioactive material to deliver radiation to the bone tumor, the tumor residing at the distance from an edge of the volume of bone cement. Some methods include dispensing the bone cement, having the activity concentration, to a health care worker for delivery to the patient.

In some methods for treating a target tissue with a radioisotope, the methods include mixing a radioisotope uniformly in a matrix material, the material configured to attenuate emissions of the radioisotope such that therapeutic emissions sufficient to treat the target tissue are emitted from substantially only the surface of the matrix material. Some methods further include exposing the target tissue to a radioactive dose that is delivered by the radioisotope substantially only about the surface of the matrix material.

In some methods, an activity per unit volume of the matrix material is used to determine the dose to the target. Some methods provide that an activity concentration and a distance from the surface of the material are used to determine the dose delivered to the target tissue. In some methods, the matrix material comprises polymethylmethacrylate. In some methods, the radioisotope is a beta-emitter, and in some embodiments, the radioisotope is at least one of P-32, Y-90, and Sr-89. Some methods provide that the matrix material comprises a high atomic number material that has been mixed with a gamma-emitting radioisotope.

Some methods described herein are directed to treating a target tissue with a radioisotope. The methods can include determining a distance between a target tissue and a surface of a bone cement to be positioned adjacent the target tissue; based on the determined distance and based on a target dose of radiation to the target tissue, determining an activity of the radioisotope to be mixed with a volume of the bone cement to obtain a desired activity concentration of the radioisotope; and mixing the radioisotope with the bone cement.

In some methods described herein for treating a target tissue with a radioisotope, the methods include determining a distance between a target tissue and a surface of a bone cement to be positioned adjacent the target tissue; based on the determined distance and based on a target dose of radiation to the target tissue, determining an activity of the radioisotope to be mixed with a volume of the bone cement to obtain a desired activity concentration of the radioisotope; and mixing the radioisotope with the bone cement.

In certain methods described herein for treating a bone tumor of a patient, the methods include determining a distance between the bone tumor and a surface of a bone cement to be positioned within the patient; based on the distance and based on a target dose of radiation to the tumor, determining an activity concentration of the radioisotope to deliver radiation to the bone tumor; and outputting the activity concentration to a nontransitory computer-readable medium.

Some methods for treating a bone tumor of a patient include based on (i) a distance between the bone tumor and a surface of bone cement to be positioned within the patient, and (ii) a dose of radiation emitted from a radioactive material, determining an activity concentration of the radioactive material that delivers the dose to the bone tumor; and dispensing the bone cement, having the activity concentration, for delivery to the patient.

In certain methods for limiting radiation damage while treating a target with a radioisotope, the methods include determining a distance between (a) a tissue to be spared radiation damage and (b) a surface of a bone cement to be positioned near the target; based on the determined distance and based on a maximal dose of radiation to the tissue, determining an activity of the radioisotope, to be mixed with the bone cement, that limits a dose of radiation to the tissue to less than the maximal dose; and mixing the radioisotope with the bone cement.

Some methods described herein for limiting radiation damage while treating a target with a radioisotope include determining a distance between (a) tissue to be spared within 10 mm of the bone tumor and (b) a surface of a bone cement to be positioned within the patient; based on the determined distance and based on a maximal dose of radiation to the tissue, determining an activity concentration of the radioisotope, in the bone cement, that limits a dose of radiation to the tissue to less than the maximal dose; and outputting the activity concentration to a nontransitory computer-readable medium.

In some methods for treating a target tissue with a radioisotope, the methods include mixing a radioisotope in a matrix material, the material configured to attenuate emissions of the radioisotope such that therapeutic emissions sufficient to treat the target tissue are emitted from substantially only within about 1.9 mm of a surface of the matrix material; and exposing the target tissue to a radioactive dose that is delivered by the radioisotope substantially only about the surface of the matrix material. In some methods for treating a target tissue with a radioisotope, the methods include mixing a radioisotope in a matrix material, the mixture configured to attenuate emissions of the radioisotope such that therapeutic emissions sufficient to treat the target tissue are emitted from substantially only within about 1.0 to about 2.5 mm of a surface of the matrix material; and exposing the target tissue to a radioactive dose that is delivered by the radioisotope substantially only about the surface of the matrix material. In some embodiments, such as when a low-energy beta-emitting radioisotope is mixed in a matrix material, the therapeutic emissions to treat the target tissue may be emitted from less than about 1 mm from the surface of the material. In some embodiments, such as when a gamma-emitting radioisotope is mixed in a matrix material, the therapeutic emissions to treat the target tissue may be emitted from a depth from the surface greater than about 2.5 mm.

Some methods of treating a target tissue in a patient's body include providing a cement for placement within the patient's body, the cement comprising a plurality of radioisotopes with a range of half-lives; and delivering the cement to a target location within the patient's body, such that the target tissue is treated with a first radioisotope of the plurality, having a half-life shorter than another of the plurality, at a higher dose than a dose administered to the target tissue by another of the plurality.

In some methods, the radioisotope emits gamma rays. This gamma-emitting radioisotope can also have a high atomic number material. For example, the high atomic number material can include at least one of Rhenium, Iridium, Tantalum, Tungsten, Gold, and a Lanthanide series element.

In some methods, the matrix material has a high atomic number material. In some of these methods, the radioisotope can emit gamma rays, and the gamma-emitting radioisotope can have a high atomic number material. The high atomic number material can includes at least one of Rhenium, Iridium, Tantalum, Tungsten, Gold, and a Lanthanide series element.

In some methods, the bone cement includes a high atomic number material that has been mixed with gamma-emitting radioisotopes. Some high atomic number materials can include, for example, Rhenium, Iridium, Tantalum, Tungsten, Gold, and a Lanthanide element. In some methods, the gamma-emitting radioisotope and the high atomic number material are the same material. For example, Rhenium (Re) and Iridium (Ir) are high Z materials and Re-186 and Ir-192 have both beta and gamma emissions. The gamma emissions from these radioisotopes may be attenuated by the Re or Ir, respectively. As a result, only the gamma emissions from the material near the surface of the Re- and/or Ir-laden cement would reach the target, so the dose to the target would be relatively independent of the amount of radioactive cement material is administered. In some methods, elements in the Lanthanide series can also work. For example, Sm-153, in its solid form could be used. These elements have even higher Z. As the Z is greater, the attenuation increases, and the thickness from which the gamma radiation irradiation contributes to the dose decreases.

In some embodiments, radioactive particles and flakes of a material having a high atomic number can be mixed with a liquid cement that cures. This liquid cement, with the high atomic number radioactive material, can be injected into a patient to treat tumors using dosimetry principles discussed herein.

Some embodiments include a radioactive material, for treating target tissue in a patient's body, that include a cement for placement within the patient's body; and a beta-emitting radioisotope mixed in the cement at a concentration of about 4 mCi per ml of cement; wherein, when any volume of the radioactive material is placed about 6 mm or more from a non-target tissue, the non-target tissue will be exposed to less than about 30 Gy; and wherein a volume of the radioactive material contacting the target tissue delivers more than 30 Gy to a depth of up to about 3.5 mm into the target tissue.

Some methods include providing a matrix material for placement within the patient's body, the matrix material comprising a plurality of radioisotopes with a range of half-lives; and delivering the matrix material to a target location within the patient's body, such that the target tissue is treated with a first radioisotope of the plurality, having a half-life shorter than another of the plurality. Some such methods include mixing at least one of Y-90, P-32, and Sr-89 with the matrix material. In some embodiments, methods further include mixing at least one material having a high atomic number in the plurality of radioisotopes. In some such embodiments, the radioisotope can emit gamma rays, and the gamma-emitting radioisotope can have a high atomic number material. The high atomic number radioisotope can include at least one of Rhenium, Iridium, Tantalum, Tungsten, Gold, and a Lanthanide series element. In some embodiments, methods employing a plurality of radioisotopes can include a mixture of beta and gamma emitting radioisotopes.

In some methods of treating a vertebral tumor, the methods include providing a bone cement and a radioisotope to be mixed with the cement to form a mixture, having an activity concentration of the radioisotope, to be placed in a vertebra; wherein the activity concentration is based on (a) a distance between a target tissue and a surface of a mixture when placed in the vertebra, and (b) a dose to be delivered to the target tissue. In some embodiments, the mixture is configured such that when placed in the vertebra and when a closest surface of the mixture is at the distance away from the target tissue, the mixture delivers substantially the dose to the target tissue independently of a total volume of the mixture placed in the vertebra Some embodiments include a radioactive material for treating target tissue in a patient's body, the radioactive material including a cement for placement within the patient's body; and a beta-emitting radioisotope mixed in the cement at a concentration of up to about 100 mCi per ml of cement; wherein, when a volume of the radioactive material is placed within 5 mm of the target tissue, the dose distribution in the target tissue is substantially the same for any volume of the radioactive material greater than about 10 mm in diameter. In some embodiments, when any volume of the radioactive material greater than about 1 to about 3 mm thick, measured in the direction of the radiation emissions to the target, and greater than about 6 mm perpendicular to said direction, is placed near the target tissue, the depth-dose distribution in the target tissue near the closest surface of the radioactive volume is substantially the same.

In some embodiments, a radioactive material for treating a target in a patient's body includes a cement having a density; and a beta-emitting radioisotope mixed with the cement at a concentration of up to about 100 mCi per ml of cement; wherein, when a volume of the radioactive material is placed within 10 mm of the target, the dose distribution in the target is substantially the same for any volume of the radioactive material having a thickness, in a direction of radiation emission from the radioactive material to the target, greater than a threshold inversely related to the density; wherein, when the threshold is about 1.8 mm, the density is about 1.35 gm/cc. In some embodiments, when the threshold is about 1.9 mm, the density is about 1.3 gm/cc.

Some methods include determining an activity concentration of a radioisotope in a mixture for treating a target tissue in a vertebra, the method comprising based on (a) a distance between the target tissue and a surface of the mixture, and (b) a dose of radiation to be delivered to the target tissue by the radioisotope, determining, by a processor, an activity concentration of the radioisotope in the mixture, the mixture resulting from combining a matrix material and the radioisotope, wherein the mixture is configured such that when placed in the vertebra and when a closest surface of the mixture is at the distance away from the target tissue, the mixture delivers substantially the dose to the target tissue independently of a total volume of the mixture placed in the vertebra.

Some methods include determining a distance from a radioisotope mixture to a target tissue in or near a vertebra, the method comprising based on (a) an activity concentration of the radioisotope in the mixture, the mixture resulting from combining a matrix material and the radioisotope, and (b) a dose of radiation to be delivered to the target tissue by the radioisotope, determining, by a processor, a distance between the target tissue and a surface of the mixture, wherein the mixture is configured such that when placed in the vertebra and when a closest surface of the mixture is at the distance away from the target tissue, the mixture delivers substantially the dose to the target tissue independently of a total volume of the mixture placed in the vertebra.

DETAILED DESCRIPTION

Figure 1:
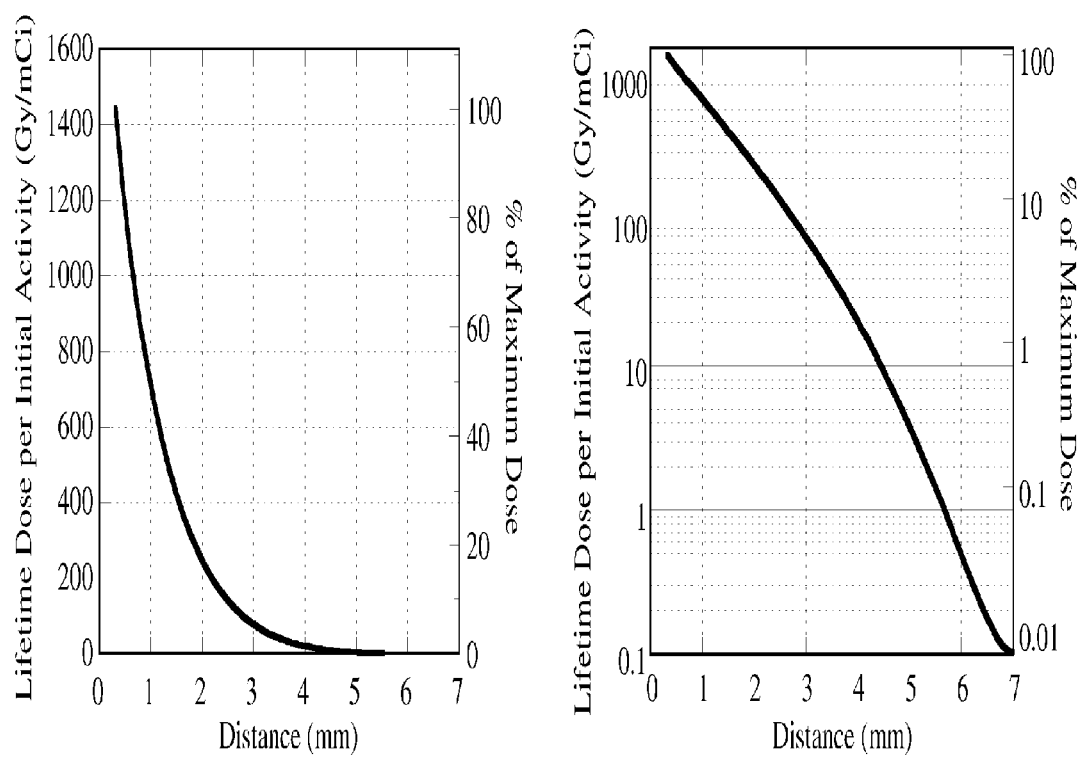
FIG. 1 depicts radial depth-dose curves in connection with embodiments described herein.

For purposes of summarizing the disclosure, certain aspects, advantages, and novel features of the disclosure are described herein. It is to be understood that not necessarily all such advantages may be achieved in accordance with any particular embodiment of the disclosure. Thus, the disclosure may be embodied or carried out in a manner that achieves or optimizes one advantage or group of advantages as taught herein without necessarily achieving other advantages as may be taught or suggested herein.

Additionally, although embodiments of the disclosure have been described in detail, certain variations and modifications will be apparent to those skilled in the art, including embodiments that do not provide all the features and benefits described herein. It will be understood by those skilled in the art that the present disclosure extends beyond the specifically disclosed embodiments to other alternative or additional embodiments and/or uses and obvious modifications and equivalents thereof. Moreover, while a number of variations have been shown and described in varying detail, other modifications, which are within the scope of the present disclosure, will be readily apparent to those of skill in the art based upon this disclosure. It is also contemplated that various combinations or subcombinations of the specific features and aspects of the embodiments may be made and still fall within the scope of the present disclosure. Accordingly, it should be understood that various features and aspects of the disclosed embodiments can be combined with or substituted for one another in order to form varying modes of the present disclosure. Thus, it is intended that the scope of the present disclosure herein disclosed should not be limited by the particular disclosed embodiments described herein.

Disclosed herein are various embodiments related to methods of delivering radiation therapy to a target. It will be understood by the skilled artisan that such radioisotopes may comprise any known radioisotope, including, without limitation, any beta emitter, any combination of beta emitters, any gamma emitter, any combination of gamma emitters, and any mixture of one or more beta emitters with one or more gamma emitters.

Spinal metastases are a common and serious manifestation of cancer, and are often treated with vertebroplasty/kyphoplasty followed by external beam radiation therapy (EBRT). As an alternative, a radioactive bone cement, i.e. bone cement incorporated with a radionuclide, can be introduced. Using a Monte Carlo radiation transport modeling method, dose distributions within vertebrae containing radioactive cement (phosphorus-32 radioactive bone cement) can be evaluated. Such evaluation of vertebrae containing radioactive cement has shown this cement to be clinically useful for treating spinal metastases. Model accuracy was evaluated by comparing model-predicted depth-dose curves to those measured experimentally in eight cadaveric vertebrae using radiochromic film. The high-gradient regions of the depth-dose curves differed by radial distances of 0.3-0.9 mm, an improvement over EBRT dosimetry accuracy. The low-gradient regions differed by 0.033-0.055 Gy/h/mCi, which may be important in situations involving prior spinal cord irradiation. Using a more rigorous evaluation of model accuracy, four models predicted the measured dose distribution within the experimental uncertainty, as represented by the 95% confidence interval of the measured log-linear depth-dose curve. The remaining four models required modification to account for marrow lost from the vertebrae during specimen preparation. However, the accuracy of the modified model results indicated that, when this source of uncertainty is accounted for, this modeling method can be used to predict dose distributions in vertebrae containing radioactive cement.

According to the teachings herein, the two steps of the conventional treatment approach may be combined into a single procedure utilizing radioactive bone cement, i.e. bone cement incorporated with a uniform distribution of a radionuclide. Such a combined approach would integrate radiation therapy and the surgical strength-restoration procedure into a single procedure for treatment. This combined approach can reduce or eliminate having separate radiation therapies and as many as 10-15 visits to the hospital (in the case of EBRT) for a patient whose quality of life has already been compromised. Additionally, by directing radioactive bone cement to the location of the tumor, a beta-emitting radionuclide can be used to create emissions that penetrate only the adjacent bone/tumor, potentially allowing for a higher dose to the target bone and minimal dose to the spinal cord and other normal tissue nearby.

To evaluate feasibility and to guide development of the radioactive bone cement technology, an analytical tool predicts the radiation dose distribution within and adjacent to vertebrae containing radioactive bone cement. Previously, a Monte Carlo model of a vertebra containing a cylinder of radioactive bone cement was presented. Although this voxelized, CT scan-based model represented the vertebral geometry well, model generation was complex, limiting the usefulness of this approach. Subsequently, another study presented the dose distribution from radioactive bone cement in a simplified model that consisted only of cortical bone. Neither study attempted to experimentally evaluate model accuracy.

Described herein is a method for automatically generating anatomically correct, patient-specific, CT scan-based Monte Carlo radiation transport models of vertebrae containing radioactive bone cement, to predict the radiation dose distribution in a vertebral body injected with radioactive bone cement. Model accuracy has been experimentally evaluated and demonstrated to accurately predict the resulting radiation dose distributions. Thus, this modeling method provides a useful analytical tool with which to evaluate the clinical usefulness of the dose distributions resulting from radioactive bone cement.

Model results indicate that a therapeutic dose could be delivered to tumor and bone within about 5 mm of the cement surface, while maintaining a safe dose to radiosensitive tissue, such as the spinal cord, beyond this distance. This therapeutic range should be sufficient to treat target volumes within the vertebral body when tumor ablation techniques are used to create a cavity into which the radioactive cement can be injected. Additionally, the effect of the vertebral bone density on the resulting dose distributions was analyzed and determined to be negligible for physiologic ranges of trabecular bone density within the vertebral body. Thus, with further development, radioactive bone cement may become an alternative to the conventional two-step approach (percutaneous strength-restoration procedure followed by radiotherapy) to treating spinal metastases.

Further embodiments describe different embodiments of various dose distributions resulting from radioactive bone cement. The clinical usefulness of these dose distributions is characterized, in some embodiments, by the attenuation of dose with distance from the cement, as well as the therapeutic range, maximum dose to bone, and dose to the spinal cord for various levels of implanted activity. The effect of the vertebral bone density on the radioactive cement dose distributions was also analyzed, as explained below.

The CT scan-based Monte Carlo radiation transport modeling method was used to evaluate dose distributions from radioactive bone cement. Models were also used to predict and compare dose distributions in a vertebra with its actual heterogeneous distribution of bone density, as well as uniform distributions of various bone densities.

The T12 vertebra was acquired for the model from a 69-year-old female donor who died from anoxic encephalopathy. A silicone mold of the posterior element of the vertebra was created and used to hold the specimen in place during CT scanning, and CT scans were obtained with the vertebra immersed in water to minimize streak artifacts (GE Discovery VCT PET/CT, standard reconstruction, 0.625-mm pixel size, 1.25-mm slice thickness, 80 kVp, 280 mAs). A calcium hydroxyapatite calibration phantom (Image Analysis Inc., Columbia, Ky.) was included in each scan and used to calculate the quantitative CT density ($\rho_{QCT}$) of each pixel.

In-house software was used to transform the CT scan data into a Monte Carlo N-Particle (MCNP) model consisting of a three-dimensional rectangular lattice of 0.625 mm×0.625 mm×1.25 mm voxels. All bone in the model was assigned a material number according to $\rho_{QCT}$ of the corresponding CT voxel. Each bone material was defined by its density and atomic composition and represented one of thirty complementary volume fractions of solid cortical bone and marrow. All soft tissue in the model, including the spinal cord, muscle, and fat, was represented by a single material. A 1.19 cm-diameter×1.13 cm-height cylindrical volume of Arthro-Care Parallax® PMMA bone cement (ArthroCare Corp., Sunnyvale, Calif.) was simulated within the model, replacing trabecular bone at the approximate center of the vertebral body. A phosphorus-32 (P-32) radionuclide source was modeled as uniformly distributed within all cement voxels, with the complete energy spectrum from Medical Internal Radiation Dose (MIRD) data. P-32 was selected due to its high-energy beta emissions (maximum: 1.71 MeV), clinically-relevant half-life (14.3 days), prior use as a radiopharmaceutical for pain palliation in patients with bone metastases, and because model accuracy was previously validated for P-32 as the radionuclide. Although this analysis was carried out using P-32, in alternate embodiments, methods of the invention may employ other radioisotopes, including, without limitation, other beta emitters, gamma emitters, and mixtures thereof. One skilled in the art will recognize that the specific numerical results of MCNP models employing other radioisotopes may differ from those described herein.

Thirty million particle histories were simulated (MCNPX v.2.5.0, Los Alamos National Laboratory, LANL) using the default cross-sections. The dose distribution was assumed to be axisymmetric about the cylindrical radioactive cement source, and pulse-height energy distribution tallies were averaged over four radial directions (anterior, posterior, left lateral, right lateral) within each of three consecutive transverse planes near the center of the height of the cement cylinder. The dose distribution was characterized by a radial depth-dose curve, i.e., the absorbed dose (Gy) over the lifetime of the radionuclide, for 1 mCi (37 MBq) of initial activity, versus radial distance from the surface of the radioactive cement, with tally results assumed to be at the center of each voxel.

The radial depth-dose curve was analyzed to evaluate the clinical usefulness of the dose distribution. The curve was first used to characterize the attenuation of dose with distance from the radioactive source, represented by the distance from the cement at which the absorbed dose was attenuated to 10% and 1% of the maximum absorbed dose in the voxel directly adjacent to the cement ($R_{10\%}$ and $R_{1\%}$, respectively).

Since the dose distribution linearly scales according to the amount of initial activity, radial depth-dose curves were then also plotted for initial activities of 2, 4, 8, and 16 mCi (74, 148, 296, and 592 MBq, respectively). For each initial activity, the resulting radial depth-dose curve was used to quantify the radial distance at which a therapeutic dose (38 Gy) is delivered ($R_{TD}$); the maximum absorbed dose in the voxel directly adjacent to the cement ($D_{Max}$); the radial distance at which the maximum allowable dose to the spinal cord (54 Gy) is delivered ($R_{cord}$); and the absorbed dose at the anterior surface of the spinal canal, corresponding to a radial distance of 7 mm from the cement ($D_{7mm}$).

To demonstrate how changes in the vertebral bone density affect the dose distribution from radioactive bone cement, nine MCNP models were created in which all bone in the vertebra was modeled as a uniform distribution of a single bone material. To accomplish this, the model described above was modified such that all thirty bone material definitions consisted of the same density and atomic composition, while the model geometry, soft tissue material definition, radioactive cement source, and tallies all remained the same. Models with a uniform distribution of bone density were created using the bone densities and corresponding volume fractions of marrow and cortical bone shown in Table 1.

TABLE 1

| Model ID | Bone Density (g/cm³) | Volume fractions (%) Marrow | Volume fractions (%) Bone |
|---|---|---|---|
| B01 | 0.980 | 100 | 0 |
| B06 | 1.104 | 89.8 | 10.2 |

TABLE 1-continued

| Model ID | Bone Density (g/cm³) | Volume fractions (%) Marrow | Volume fractions (%) Bone |
|---|---|---|---|
| B13 | 1.221 | 80.2 | 19.8 |
| B18 | 1.369 | 68.1 | 31.9 |
| B21 | 1.497 | 57.6 | 42.4 |
| B23 | 1.606 | 48.7 | 51.3 |
| B25 | 1.738 | 37.9 | 62.1 |
| B27 | 1.897 | 24.9 | 75.1 |
| B30 | 2.200 | 0 | 100 |

Note that these densities are true bone densities, accounting for bone as well as marrow within its pores, and not bone mineral densities. For each model, the resulting radial depth-dose curve was normalized to the maximum absorbed dose in the voxel directly adjacent to the cement. The effect of the surrounding bone density on the radiation dose distributions was then quantified by estimating $R_{10\%}$ and $R_{1\%}$ for each normalized radial depth-dose curve.

For the model with the CT scan-based, heterogeneous distribution of bone density, the lifetime dose per mCi of initial activity is shown in FIG. 1 on a linear (left) and log (right) scale. The secondary y-axis of each plot indicates the values on the primary y-axis normalized to the maximum absorbed dose in the voxel directly adjacent to the radioactive cement. The radial depth-dose curve decreases exponentially with increasing distance from the radioactive cement. The radial depth-dose curve for the model with the actual, CT scan-based, distribution of bone density demonstrated that the lifetime dose per mCi of initial activity decreases exponentially with increasing distance from the radioactive cement, yielding an $R_{10\%}$ and $R_{1\%}$ of 2.5 mm and 4.2 mm, respectively.

Figure 2:
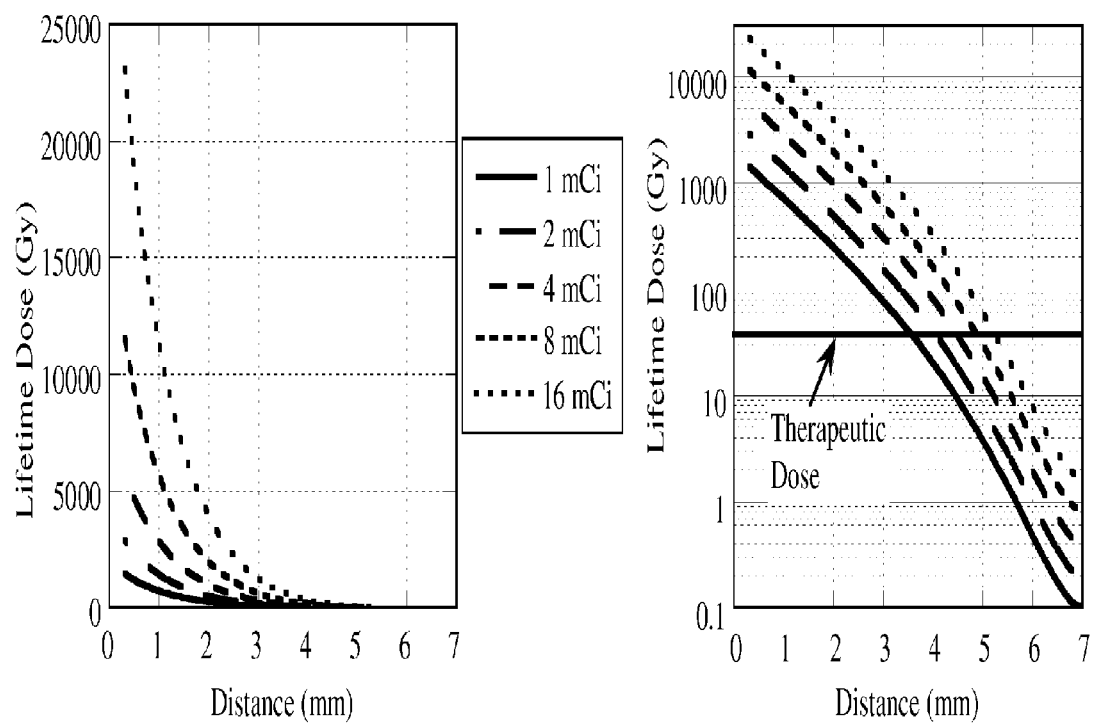
FIG. 2 depicts radial depth-dose curves in connection with embodiments described herein.

In addition to the radial depth-dose curve for an initial activity of 1 mCi, above, the radial depth-dose curves for initial activities of 2, 4, 8, and 16 mCi (74, 148, 296, and 592 MBq, respectively) were constructed, with the therapeutic dose of 38 Gy also indicated. For the model with the CT scan-based, heterogeneous distribution of bone density, the lifetime dose for various initial activities is shown in FIG. 2 on a linear (left) and log (right) scale. For reference, the therapeutic dose of 38 Gy is also shown on the log scale plot. The corresponding $R_{TD}$ ranged from 3.5-5.1 mm; the corresponding $D_{Max}$ ranged from 1445-23119 Gy; the corresponding $R_{cord}$ ranged from 3.2-5.0 mm; and the corresponding $D_{7mm}$ ranged from 0.10-1.56 Gy, as shown below in Table 2, which shows dosimetric characteristics of the radial depth-dose curve for the model with actual bone density distribution using various initial activities.

TABLE 2

| Initial Activity | | $R_{TD}$ (mm) | $D_{Max}$ (Gy) | $R_{cord}$ (mm) | $D_{7\,mm}$ (Gy) |
|---|---|---|---|---|---|
| 1 mCi | 37 MBq | 3.5 | 1445 | 3.2 | 0.10 |
| 2 mCi | 74 MBq | 4.0 | 2890 | 3.8 | 0.19 |
| 4 mCi | 148 MBq | 4.4 | 5780 | 4.2 | 0.39 |
| 8 mCi | 296 MBq | 4.8 | 11559 | 4.6 | 0.78 |
| 16 mCi | 592 MBq | 5.1 | 23119 | 5.0 | 1.56 |

For each model with a uniform distribution of bone density, the resulting radial depth-dose curve, normalized to the maximum absorbed dose in the voxel directly adjacent to the cement demonstrated that for these models, $R_{10\%}$ and $R_{1\%}$ were between 1.5-2.7 mm and 2.4-4.5 mm, respectively, as shown in Table 3, which shows attenuation characteristics of the radial depth-dose curve for each model with a uniform distribution of bone density.

TABLE 3

| Model ID | $R_{10\%}$ (mm) | $R_{1\%}$ (mm) |
|---|---|---|
| B01 | 2.7 | 4.5 |
| B06 | 2.4 | 4.1 |
| B13 | 2.3 | 3.7 |
| B18 | 2.1 | 3.4 |
| B21 | 1.9 | 3.2 |
| B23 | 1.8 | 3.0 |
| B25 | 1.7 | 2.8 |
| B27 | 1.6 | 2.6 |
| B30 | 1.5 | 2.4 |

The clinical usefulness of dose distributions from P-32 radioactive bone cement was examined by determining the therapeutic range, maximum dose, and dose to the spinal cord of these dose distributions. The results of this study indicate that these dose distributions could be used to deliver a therapeutic dose to a clinically useful distance within vertebrae with spinal metastases, while maintaining a safe dose to the spinal cord. As mentioned above, although this analysis was carried out using P-32, in alternate embodiments, methods of the invention may employ other radioisotopes, including, without limitation, other beta emitters, gamma emitters, and mixtures thereof. One skilled in the art will recognize that the specific numerical results of MCNP models employing other radioisotopes may differ from those described herein.

For the initial model with the CT scan-based heterogeneous distribution of bone density, the absorbed dose is attenuated exponentially with distance from the cement. The steep gradient of this dose distribution results in a highly-localized dose and minimal exposure to nearby radiosensitive tissues, a result that would be difficult or impossible to achieve with a gamma-emitting radionuclide. Conversely, the gradient is flat enough that 10% of the maximum dose is delivered to bone within ~2.5 mm and 1% of the maximum dose is delivered within ~4.2 mm. This result might be difficult, or less-likely, to achieve with an alpha-emitting or low-energy beta-emitting radionuclide, which would likely produce emissions that may be completely absorbed by bone immediately adjacent to the cement. These attenuation characteristics indicate that the dose distributions from P-32 radioactive cement may be clinically useful. It was also noted that the dose distribution linearly scales according to the amount of initial activity.

The therapeutic range of the dose distribution increases by 0.3-0.5 mm for every doubling of the initial activity. However, considering that $D_{Max}$ also doubles with each doubling of the initial activity (discussed below), the practical limit on the level of implanted activity is likely between 10-20 mCi (370-740 MBq), yielding a maximum therapeutic range for P-32 radioactive bone cement of about 5 mm. The clinical usefulness of this distance would be dependent on the accuracy with which the cement could be placed near the target volume within the vertebra. This issue is slightly complicated by the fact that the target volume used in SBRT for spinal metastases is not yet standardized, ranging from only the identifiable extent of the tumor to the entire vertebra, including the pedicles and posterior elements.

Injection of bone cement directly into a lesion has been shown to fill more than 75% of the tumor volume with cement. For a target volume consisting of only the identifiable extent of the tumor, injecting radioactive bone cement directly into the tumor would likely deliver a therapeutic dose to most or all of the target volume. However, since the tumor tissue acts as an incompressible space-occupier, extensive filling of the tumor itself also leads to increased risk of cement and/or tumor extravasation into the spinal canal. Thus, embodiments of tumor removal or ablation techniques, such as curetting, laser-induced thermotherapy, and plasma-mediated radiofrequency ablation, can be used to debulk the tumor tissue prior to cement injection, creating a cavity into which the cement can then be injected. These techniques can enable radioactive bone cement to be accurately placed directly in the target volume, immediately adjacent to residual tumor tissue that may remain after debulking, and with minimal risk of cement extravasation. Thus, when used in conjunction with these ablation techniques, radioactive bone cement with a therapeutic range of 5 mm would likely be appropriate to treat a target volume consisting of the extent of the tumor.

When used in conjunction with ablation and other cavity-creating techniques, radioactive bone cement may also be able to effectively treat target volumes beyond the extent of the tumor. These tumor debulking methods would enable the radioactive cement injection to be accurately controlled and placed in specific locations within the vertebral body, resulting in a predictable cement fill that would perhaps make a therapeutic range of 5 mm sufficient to treat the entirety of even a large vertebral body. However, in the event that a region is not adequately irradiated and/or a tumor recurs, it should also be noted that prior use of radioactive bone cement would not preclude repeating this treatment or subsequent treatment with conventional radiotherapy.

Although the therapeutic range of radioactive bone cement can be extended by increasing the initial activity, the maximum dose to bone directly adjacent to the cement doubles with each doubling of the initial activity, thus presenting an upper limit to the initial activity that can be safely implanted. The maximum doses for the initial activities studied here might be particularly useful for treating tumors that are relatively insensitive to radiation, such as melanoma, renal cell, and thyroid metastases. However, absorbed doses as high as 23 kGy, as predicted in this study for an initial activity of 16 mCi, would also be expected to lead to bone resorption and necrosis, potentially leading to an eventual reduction in the structural integrity of the vertebral body. Fortunately, this effect would be mitigated by the presence of the cement itself, which would provide structural reinforcement to the affected region. Furthermore, the compressive mechanical properties of human trabecular bone become significantly degraded at doses between 51 kGy and 60 kGy, above the predicted dose, so the short-term structural integrity of the bone surrounding the radioactive cement would be less likely at risk. Such high doses would also not be expected to significantly degrade the mechanical properties of the cement itself, as only slight reductions result from doses as high as 100 kGy.

Finally, $R_{cord}$ and $D_{7mm}$ can be used to determine whether radioactive bone cement would deliver excessive radiation to radiosensitive tissues such as the spinal cord. Values of $R_{cord}$ for the initial activities studied here indicate that the radioactive cement could not be safely placed within 3-5 mm of the spinal cord, similar to the 5 mm margin between tumor and spinal cord used in SBRT. In this particular model, where the anterior surface of the spinal canal is 7 mm away from the surface of the radioactive cement, the absorbed doses ($D_{7mm}$) are much lower than the maximum allowable dose to the spinal cord, even for the highest level of initial activity. Thus, even in patients with prior spinal cord irradiation, the absorbed dose at this distance would be unlikely to cause spinal cord myelopathy.

Figure 3:
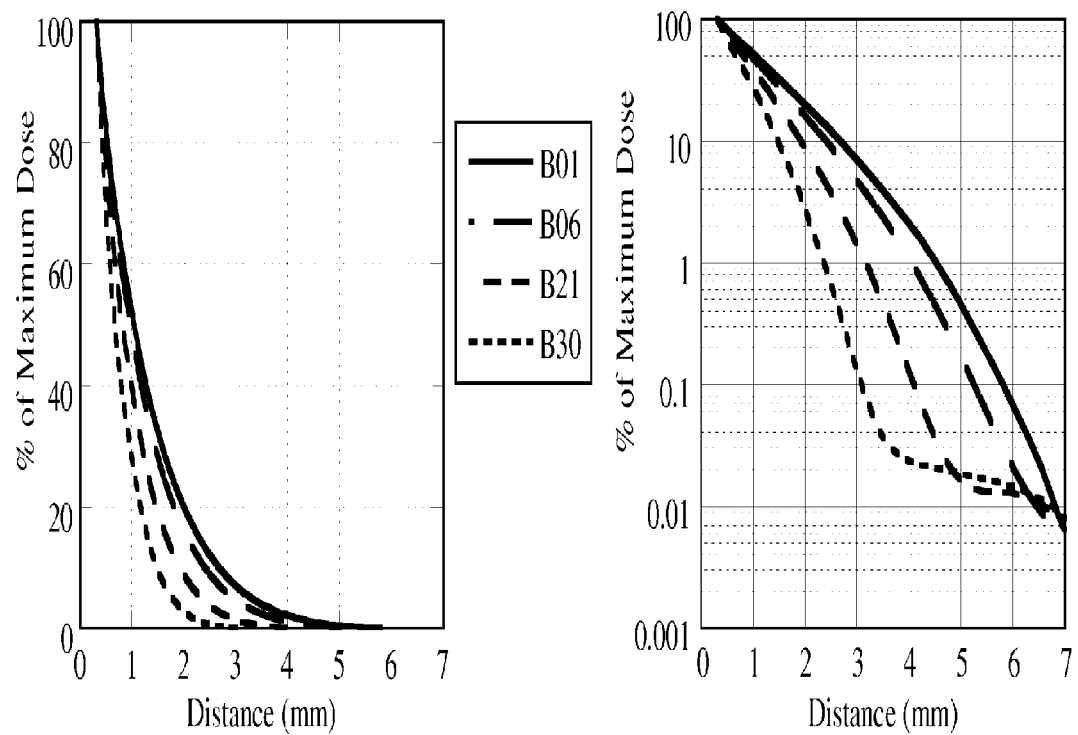
FIG. 3 depicts radial depth-dose curves in connection with embodiments described herein.

For four of the models with a uniform distribution of bone density, the radial depth-dose curve, normalized to the maximum absorbed dose in the voxel directly adjacent to the radioactive cement, is shown in FIG. 3 on a linear (left) and log (right) scale. Curves of FIG. 3 indicate that the dose from radioactive bone cement is attenuated more rapidly by higher density bone than lower density bone. This effect may be of little importance when the functional range of the dose distribution is completely confined within the interior of the vertebral body, which consists of trabecular bone with a comparatively narrow density range. For three female and six male donors between the ages of 44-88 years, the density (with marrow) of vertebral trabecular bone was between 1.0-1.1 g/cm$^3$. The differences between $R_{10\%}$ and $R_{1\%}$ on the radial depth-dose curves for bone densities of 0.980 g/cm$^3$ (model B01) and 1.104 g/cm$^3$ (model B06) was 0.3 mm and 0.4 mm, respectively, indicating that the sensitivity of the dose to realistic variations in trabecular bone density is negligible. However, presence of blastic lesions may increase attenuation of the radiation and reduce the dose. Further, the increased attenuation of high density bone might be beneficial for shielding the spinal cord and nerves, as the cortical shell would provide additional attenuation of the radiation dose as it exits the vertebral body. For the model of solid cortical bone (with a density of 2.200 g/cm$^3$), our values for $R_{10\%}$ and $R_{1\%}$ (1.5 mm and 2.4 mm, respectively) are similar to an other researcher's estimates for $R_{10\%}$ and $R_{1\%}$ of 1.03 mm and 2.00 mm, respectively. These results compare well after considering that our tally results were assumed to be at the center of each voxel, while other calculations assume tally results to be at the edge closest to the cement, leading to an offset in the radial distance of 0.3125 mm.

This study evaluated dose distributions resulting from radioactive bone cement using P-32 as the radionuclide. Alternative radionuclides such as strontium-89 (Sr-89), yttrium-90 (Y-90), and rhenium-188 (Re-188), each with their own characteristic energy spectrum and particle emissions type, would produce dose distributions that might vary greatly from those presented here. Using these radionuclides in combination may also provide some benefits by taking advantage of varying half-lives and particle energies. The MCNP models can be easily modified to predict dose distributions from alternative radionuclides or combinations thereof. However, an experimental evaluation of model accuracy, as was performed previously for P-32, would be carried out when employing alternative radionuclides. Thus, methods of the invention may include any mixture of Y-90, P-32, and Sr-89. In some embodiments, methods may also include at least one radioisotope having a high atomic number. In some such embodiments, the radioisotope can emit gamma rays, and the gamma-emitting radioisotope can have a high atomic number. The high atomic number radioisotope can include at least one of Rhenium, Iridium, Tantalum, Tungsten, Gold, a Lanthanide series element, and mixtures thereof. In some embodiments, methods employing a plurality of radioisotopes can include a mixture of beta and gamma emitting radioisotopes.

Dose distributions were evaluated using an idealized, cylindrical volume of radioactive bone cement. Clinical vertebroplasty may involve cement distributions that are more complex and involve cement-bone interdigitation. However, the cylindrical cement specimens enabled their resulting axisymmetric dose distributions to be quantified by a single radial depth-dose curve, greatly simplifying their characterization and dosimetric analysis. Use of the idealized cement geometry also allowed the surrounding bone density to be easily modified, enabling a systematic analysis of its effect on the resulting dose distribution.

Since extravasation of radioactive bone cement into the spinal canal could lead to an extremely high dose to the spinal cord, use of radioactive bone cement with tumor ablation techniques may be advisable. Additionally, the cement viscosity at the time of injection could affect the likelihood of extravasation, and guidelines for injecting at the optimal viscosity may thus be developed.

Although systemic uptake of a liquid radionuclide has been used in conjunction with kyphoplasty, it is desirable for leaching of the radionuclide from the cement be prevented to minimize toxicity in radiosensitive tissues outside of the vertebra. This issue is dependent on the chemical form of the radionuclide.

Dose distributions from P-32 radioactive bone cement were evaluated and shown to be clinically useful for treating spinal metastases. Model results indicated that a therapeutic dose could be delivered to tumor and bone within about 5 mm of the cement surface, while maintaining a safe dose to radiosensitive tissue, such as the spinal cord, beyond this distance. This therapeutic range should be sufficient to treat target volumes within the vertebral body when tumor ablation techniques are used to create a cavity into which the radioactive cement can be injected. Additionally, the effect of the vertebral bone density on the resulting dose distributions was analyzed and determined to be negligible for physiologic ranges of trabecular bone density within the vertebral body. Thus, radioactive bone cement may be used as an alternative to the conventional two-step approach (percutaneous strength restoration procedure followed by radiotherapy) to treating spinal metastases.

The therapeutic dose and an upper limit of allowable dose, in some embodiments, to the spinal cord were calculated using the linear-quadratic approach to provide doses with the same biological effectiveness as the corresponding doses used in conventional radiotherapy. For conventional radiotherapy, the biologically effective dose (BED) is given by:

$$BED = nd\left(1 + \frac{d}{\alpha/\beta}\right) \quad (1)$$

where n and d are the number of fractions and the dose per fraction, respectively, for fractionated radiotherapy, and α/β is a characteristic of the fractionation sensitivity specific to each tissue type. For a permanent implant, the BED is given by:

$$BED = D\left\{1 + \left[\frac{D \cdot \lambda}{(\mu + \lambda)(\alpha/\beta)}\right]\right\} \quad (2)$$

where D is the total absorbed dose over the lifetime of the radionuclide, λ is the radioactive decay constant of the radionuclide, and μ is the tissue repair rate constant, assumed to be 0.46 h$^{-1}$. Substituting (1) into (2) results in a quadratic equation that can be solved for D, yielding the physical lifetime dose from a permanent implant that has the same biological effectiveness as the fractionated radiotherapy to which it is compared. For patients receiving EBRT for spinal metastases, a total dose of 30 Gy fractionated over 10 daily treatment sessions of 3 Gy/fraction is often prescribed. Using $\alpha/\beta=10$ Gy for tumor control, this corresponds to a BED of 39 $Gy_{10}$. Likewise, for patients receiving a single fraction of SBRT for spinal metastases, the maximum allowable dose to the spinal cord is often set at 10 Gy. Using $\alpha/\beta=2$ Gy for late effects in the spinal cord, this corresponds to a BED of 60 $Gy_2$. For a P-32 permanent implant, these BEDs correspond to physical lifetime doses of 38 Gy and 54 Gy for a therapeutic dose and the maximum allowable dose to the spinal cord, respectively. That the therapeutic dose is less than the maximum allowable dose to the spinal cord is a result of the difference between the $\alpha/\beta$ ratios used for acute tumor effects ($\alpha/\beta=10$ Gy) and late-reacting tissues such as the spinal cord ($\alpha/\beta=2$ Gy), as well as the half-life of P-32. The extended delivery period of the P-32 radionuclide allows for more repair of late-reacting tissue than does a single, hypofractionated dose from SBRT.

Some embodiments herein relate to a characteristic of the radioactive bone cement and are in contrast with the conventional approach to brachytherapy. In conventional brachytherapy, radioactive seeds are implanted in or next to the tissue requiring radiation therapy (the tumor, or target, region). Since each brachytherapy seed contributes to the dose to the target region, increasing the activity increases the dose, and treatment guidelines are developed in terms of the total activity implanted.

In comparison, since radioactive bone cement is intended to provide structural support in addition to radiation therapy, the volume of cement injected depends on the size of the cavity it fills, so the entire volume of radioactive bone cement is not necessarily in close proximity to the target region. When P-32, a radioactive isotope of phosphorous and a beta-emitter, is used as the radioisotope, increasing the dose to the target region is not necessarily accomplished by adding more radioactive bone cement, since the additional bone cement may be farther away from the target region than the range of the P-32 emissions. Instead, the radiation dose delivered to the target region is dependent only on the activity in the cement that is within a certain specified distance. This distance is a characteristic of the particular radioisotope. Therefore, treatment guidelines for using radioactive bone cement with P-32 as the radioisotope should not be developed in terms of the total amount of cement (and, thus, the total activity) implanted in the bone, but should instead be in terms of the activity concentration in the cement (mCi per ml of cement). The following example illustrates the underlying principle. If the amount of cement injected into a bone is doubled, the total activity in the bone would be doubled, but the dose to a given target region will change only when that target region is within a certain specified distance from the additional volume of cement.

Figure 4:
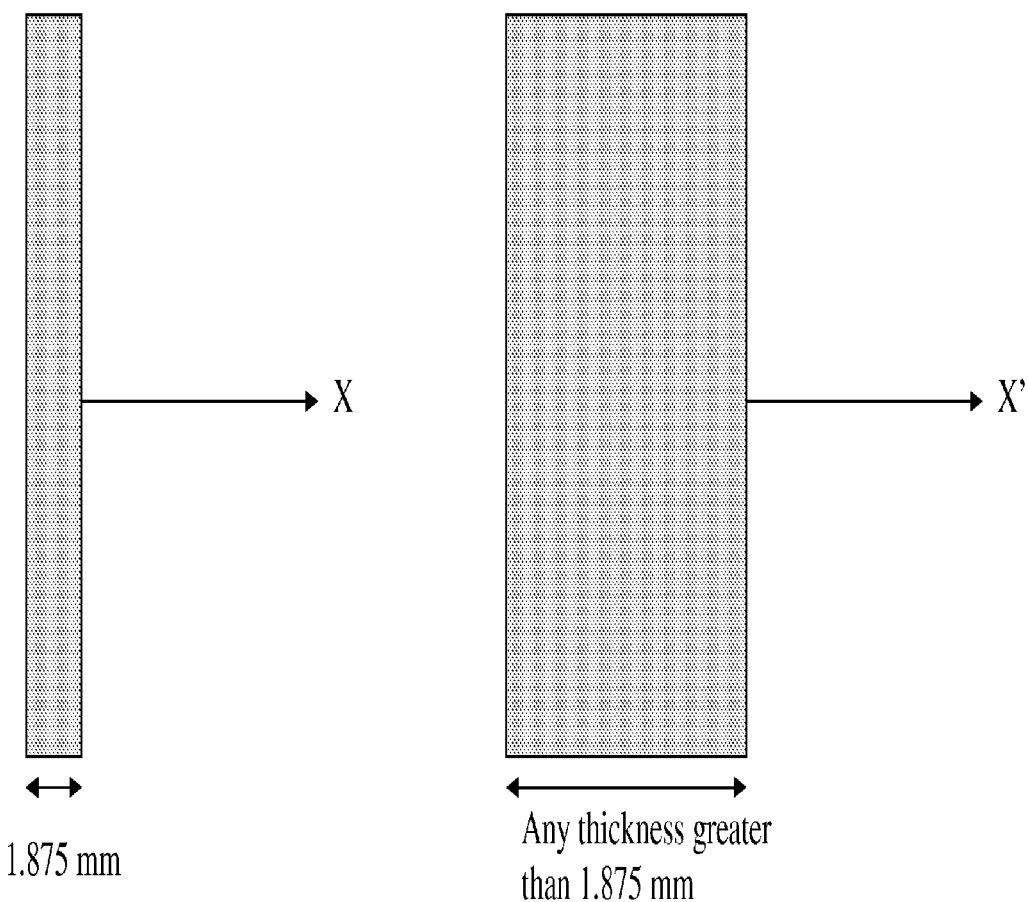
FIG. 4 illustrates effect of cement thickness on dose distributions in accordance with embodiments herein.

Specific calculated values of the cement thickness beyond which additional cement will not increase the dose delivered to target tissue (tissue near the X and X' axes) are illustrated in FIG. 4.

The fundamental reason that the radioactive cement demonstrates this property is that beta emissions penetrate only a short distance through polymethylmethacrylate (PMMA). As a result, the radiation dose to target tissue, which would be near the X and X' axes in FIG. 4, depends almost entirely on the activity of the radioactive material that is near the surface of the bone cement. Based on computer models, the dose to target tissue from about a 2 mm thick layer of radioactive cement is essentially identical to the dose from an infinitely thick layer of cement. This is correct if the thickness of the cement that is placed in the tissue is greater than approximately 1.875 mm. As shown in FIG. 4, the dose distribution along axis X is the same as that along axis X', as long as the cements are identical. The 1.875 mm figure is for P-32.

A lower energy beta emitter would require a lower thickness (compared with 1.875 mm for P-32) to exhibit this behavior. In some embodiments, such as when a low-energy beta-emitting radioisotope is mixed in a matrix material, the surface thickness may be less than about 1.0 mm. The lower energy beta emitter would also not penetrate as deeply into the surrounding tissues. This could be useful for very sensitive tissues in which penetration is to be very short.

This characteristic is probably not true for most gamma emitting radioisotopes because gamma radiation can penetrate bone cement. However, very low-energy gamma emitters may exhibit this behavior. In some embodiments, such as when a gamma-emitting radioisotope is mixed in a matrix material, the surface thickness may be greater than about 2.5 mm. Further, for a gamma-emitting radioisotope, gamma emissions may be sufficiently attenuated by a matrix material with a high atomic number and/or a high density to cause the dose to a target tissue at a specific distance from the cement surface to be approximately constant when the cement thickness reaches or exceeds a particular thickness.

The amount of activity that can be mixed with the cement to deliver a clinically relevant dose to the bone is feasible from a logistical, economic, and physical perspective, despite the fact that only the activity "near the surface" of the cement influences the dose to the bone. If, say, only the cement within 0.01 mm of the surface were responsible for the dose to the bone, the amount of activity that would be necessary to mix with the cement would be so great that it would be prohibitively expensive. Also, it is possible that, for some radioisotopes, it could be physically impossible to achieve a sufficient specific activity (mCi per unit mass) to make a useful radioactive bone cement (e.g. if the specific activity required was too high to achieve with available nuclear reactors, and/or if the achievable specific activity required such a great amount of radioactive compound that it would affect the mechanical properties of the cement).

Figure 5:
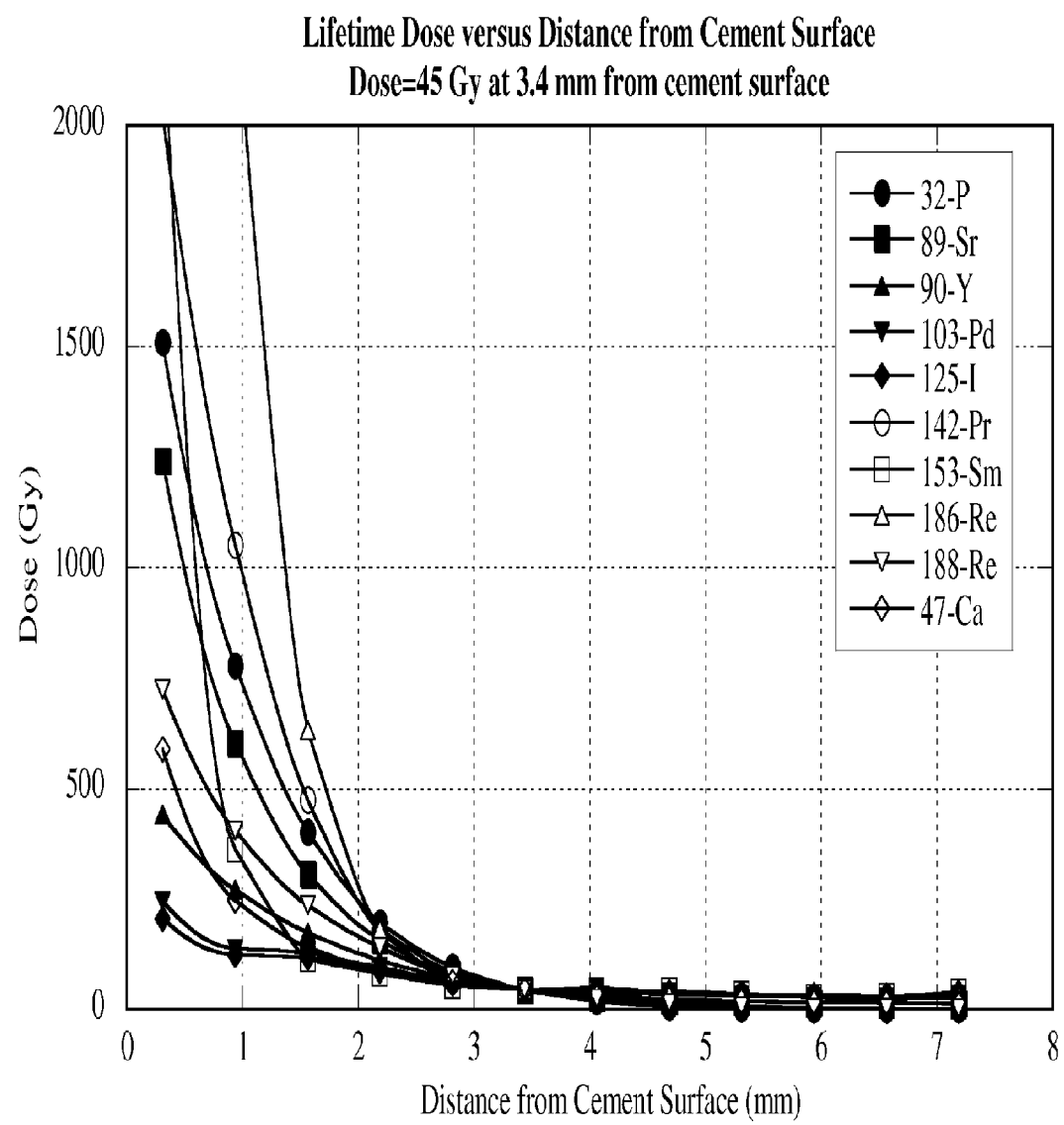
FIG. 5 depicts dose distributions for various radionuclides potentially used in radioactive cement, where each dose distribution has been adjusted to deliver 45 Gy to bone 3.5 mm from a surface of a cement.

Although the disclosure throughout describes studies and methods conducted with P-32, there may be a number of radioisotopes that can be used. For example, Sr-89 behaves much like P-32. The required activity to deliver the target dose depends on the energy (which determines the thickness through which the beta emission will pass), the half-life, and whether the radioisotope is a gamma or beta-emitter. FIG. 5 and Table 4 shows the results of preliminary models that determined the activity required to deliver 45 Gy to bone 3.5 mm from the surface of the cement.

TABLE 4

| Isotope | Half life (days) | Max β- Energy (MeV) | Mean β- Energy (MeV) | γ Energy (MeV) | γ Emissions (%) | Activity Req'd (mCi) | Dose (Gy) at 0.3 mm | Dose (Gy) at 7.2 mm |
|---|---|---|---|---|---|---|---|---|
| P-32 | 14.3 | 1.709 | 0.695 | n/a | n/a | 0.94 | 1508.4 | 0.0 |
| Ca-45 | 163.8 | 0.251 | 0.0769 | 0.0125 | 0.000003 | 810.38 | 138265.8 | 23.4 |
| Ca-47 | 4.536 | 1.94 | 0.398 | | | 5.01 | 589.7 | 13.5 |

TABLE 4-continued

| Isotope | Half life (days) | Max β- Energy (MeV) | Mean β- Energy (MeV) | γ Energy (MeV) | γ Emissions (%) | Activity Req'd (mCi) | Dose (Gy) at 0.3 mm | Dose (Gy) at 7.2 mm |
|---|---|---|---|---|---|---|---|---|
| Sr-89 | 50.5 | 1.46 | 0.58 | 0.91 | 0.009 | 0.51 | 1241.4 | 14.0 |
| Y-90 | 2.67 | 2.281 | 0.934 | n/a | n/a | 1.06 | 440.5 | 0.9 |
| Pd-103 | 17 | 0.493 | | 0.021 | | 44.21 | 245.9 | 33.5 |
| I-125 | 60.1 | 0.031 | | 0.0274 | | 10.42 | 205.4 | 39.5 |
| Pr-142 | 0.797 | 2.162 | 0.809 | 1.58 | 3.700 | 37.59 | 2019.9 | 23.7 |
| Sm-153 | 1.95 | 0.81 | 0.23 | 0.103 | 28.000 | 348.94 | 2254.2 | 39.9 |
| Re-186 | 3.87 | 1.071 | 0.323 | 0.137 | 9.500 | 137.18 | 7768.8 | 30.8 |
| Re-188 | 0.708 | 2.118 | 0.765 | 0.155 | 15.000 | 21.75 | 723.5 | 2.0 |

If the radioactive cement that were used did not exhibit the property of surface emission, methods of application would include estimating the volume of cement that would be injected before doing the procedure and then performing computer modeling or, perhaps, using charts to determine in advance how much activity can be mixed with the total amount of cement that would be injected. In many instances, this approach can be logistically difficult.

Also, in many such instances, radioactive seeds, not radioactive cement, may be used. Prior to implanting the seeds, calculations can be performed to determine the number of seeds, the activity in each seed, and placement locations in order to achieve the desired dose and dose distribution. Increasing the number of seeds and/or the activity in each seed would result in a greater dose. In many instances, this approach can also be logistically difficult.

In some embodiments described herein, the desired dose is determined in connection with the distance between the target dose and the surface of the cement. These parameters can be used to determine the activity concentration (mCi per vol. of cement) that are used in the mix. In some embodiments, the amount of cement injected is not required for the administering calculation as long as the surface of the cement is positioned in the proper location, relative to the target, in order to obtain the desired or target dose.

A number of parametric studies were conducted to examine the sensitivity of the radiation transport modeling method to various model components including the volume/shape of the cement source, the material definitions of the surrounding bone, and the specific form of the radioisotope and bone cement used. As such, these factors were adjusted independently of the remaining model parameters to determine their effect on the resulting dose distribution. The volume and shape of the radioactive cement source, as well as the density of the surrounding bone material, influence the resulting dose distribution within the vertebral body; while the atomic composition of the surrounding bone, the specific radioactive compounds analyzed, and the bone cement brands analyzed, do not. The effects of the cement volume and shape on dose distribution may have important implications for the clinical implementation of radioactive bone cement to treat spinal metastases. This information will be important in the development of clinical treatment guidelines. The relative effects of all of the studied parameters on the resulting dose distribution are valuable for other parts of this study, in which the accuracy of the MCNP modeling method will be evaluated, and the models modified as necessary until the predicted dose distributions agree with those measured experimentally.

The basis for the parametric studies was a CT scan-based MCNP model of an L4 vertebra, created using the modeling method developed and with the following model characteristics: three-dimensional rectangular lattice of 0.625 mm×0.625 mm×1.25 mm voxels; thirty bone materials and one soft tissue material, as described previously; P-32 radioisotope source uniformly distributed within ArthroCare Parallax® Bone Cement (ArthroCare Corp., Sunnyvale, Calif.); pulseheight energy tallies in a column of voxels extending away from the center of the posterior face of the cement volume (FIG. 6, FIG. 9); 30 million particle histories; MCNPX v.2.5.0. The tally results were used to predict lifetime dose distributions for each set of input parameters, thereby allowing the effect of changes in each model parameter to be elucidated.

Figure 6:
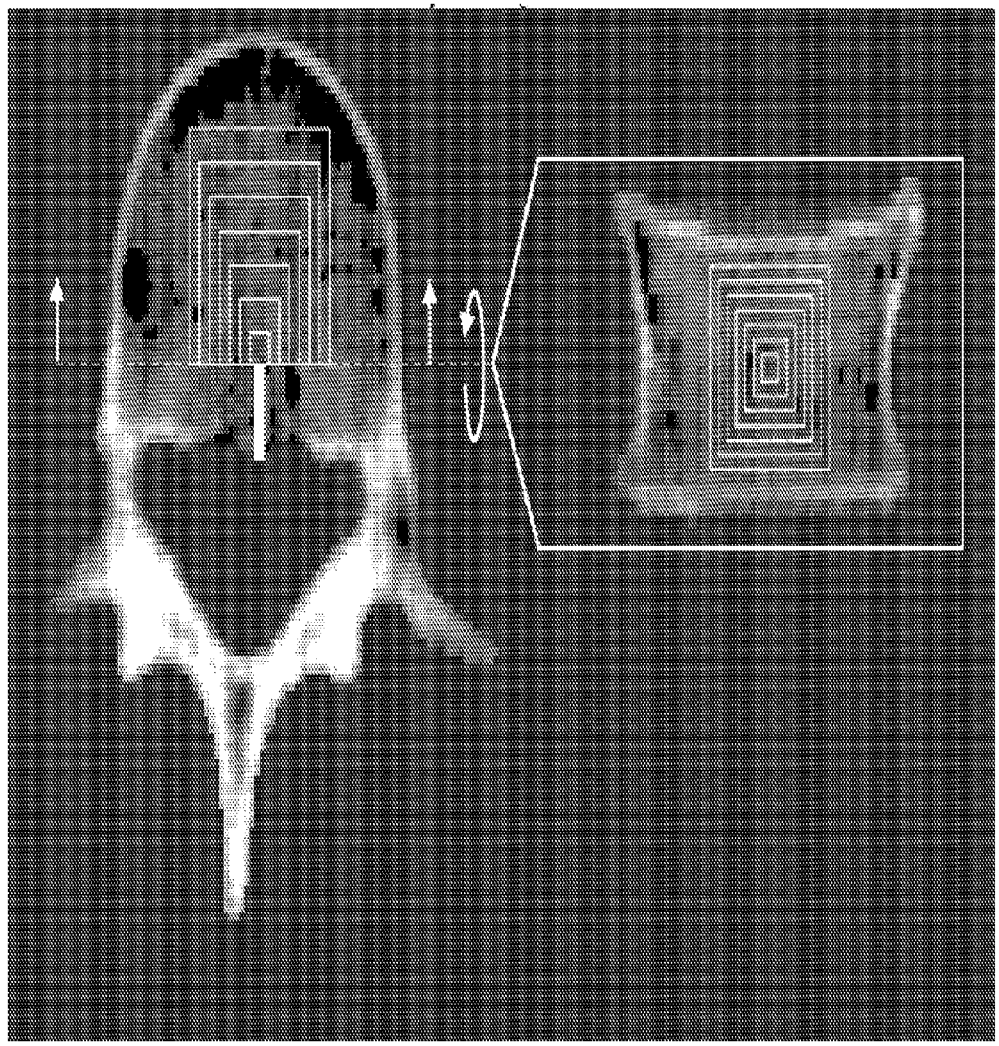
FIG. 6 is an image of a transverse and a coronal cross-section of a vertebra, showing outlines of the cubic volumes of radioactive bone cement that were modeled in each of seven MCNP models, and the voxels in which dose was determined.

To understand the effect of volume of the cement source on the dose distribution, seven Monte Carlo N-Particle (MCNP) radiation transport models were created of an L4 vertebra. Each model contained a cubic volume of cement, with edge lengths ranging from 2.5 mm to 17.5 mm, in 2.5 mm increments, and located within the vertebral body such that the posterior face of each cube was centered in the same position (FIG. 6). FIG. 6 depicts a transverse cross-section of the L4 vertebra from Donor 1 (discussed further below, with reference to Table 5), showing outlines of the cubic volumes of radioactive bone cement that were modeled. In each model, the dose distribution was analyzed in a column of bone voxels extending away from the center of the posterior face, represented by the solid white column (FIG. 6). The analyzed voxels were the same for each model, so observed differences were due only to changes in the volume of the cement source. The inlay shows a coronal cross-section of the vertebra, viewed in the anterior direction (in the direction of the arrows), and the position of each cubic volume of cement within the coronal plane.

Figure 7:
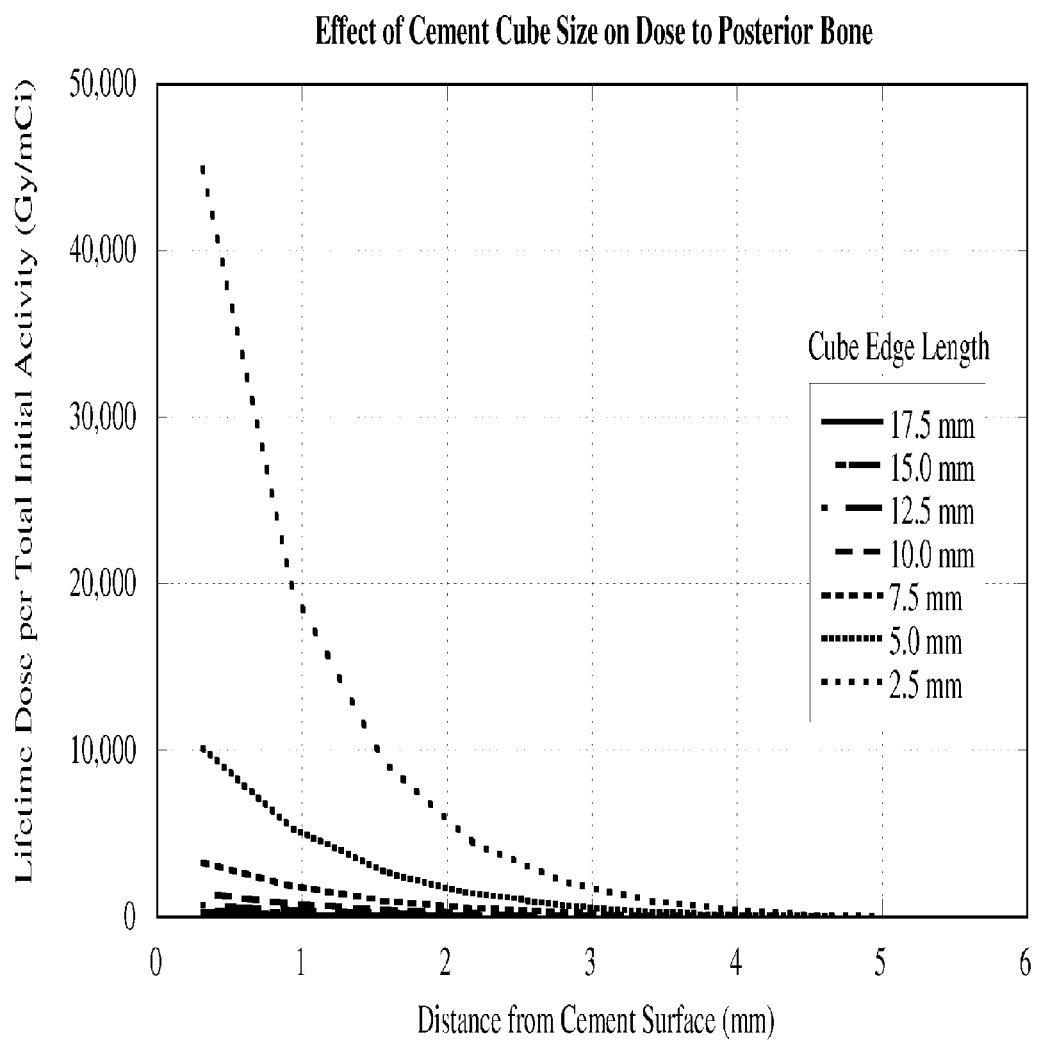
FIG. 7 depicts distributions of dose per total initial activity for the seven MCNP models containing various sizes of cubes of radioactive bone cement.

The distributions of dose per mCi of total initial activity for each volume of cement for the seven MCNP models containing various sizes of cubes of radioactive bone cement are shown in FIG. 7. The distributions indicate that, if the total initial activity mixed with the cement is held constant, a smaller volume of cement yields a greater dose to the target region than a larger volume of cement. This result can be attributed to the fact that the total initial activity is more highly concentrated in a smaller volume than a larger volume. Accordingly, it is likely that more clinically relevant information can be elucidated by analyzing dose distributions for a constant initial activity concentration, i.e., dose per mCi per unit volume of the cement.

Figure 8:
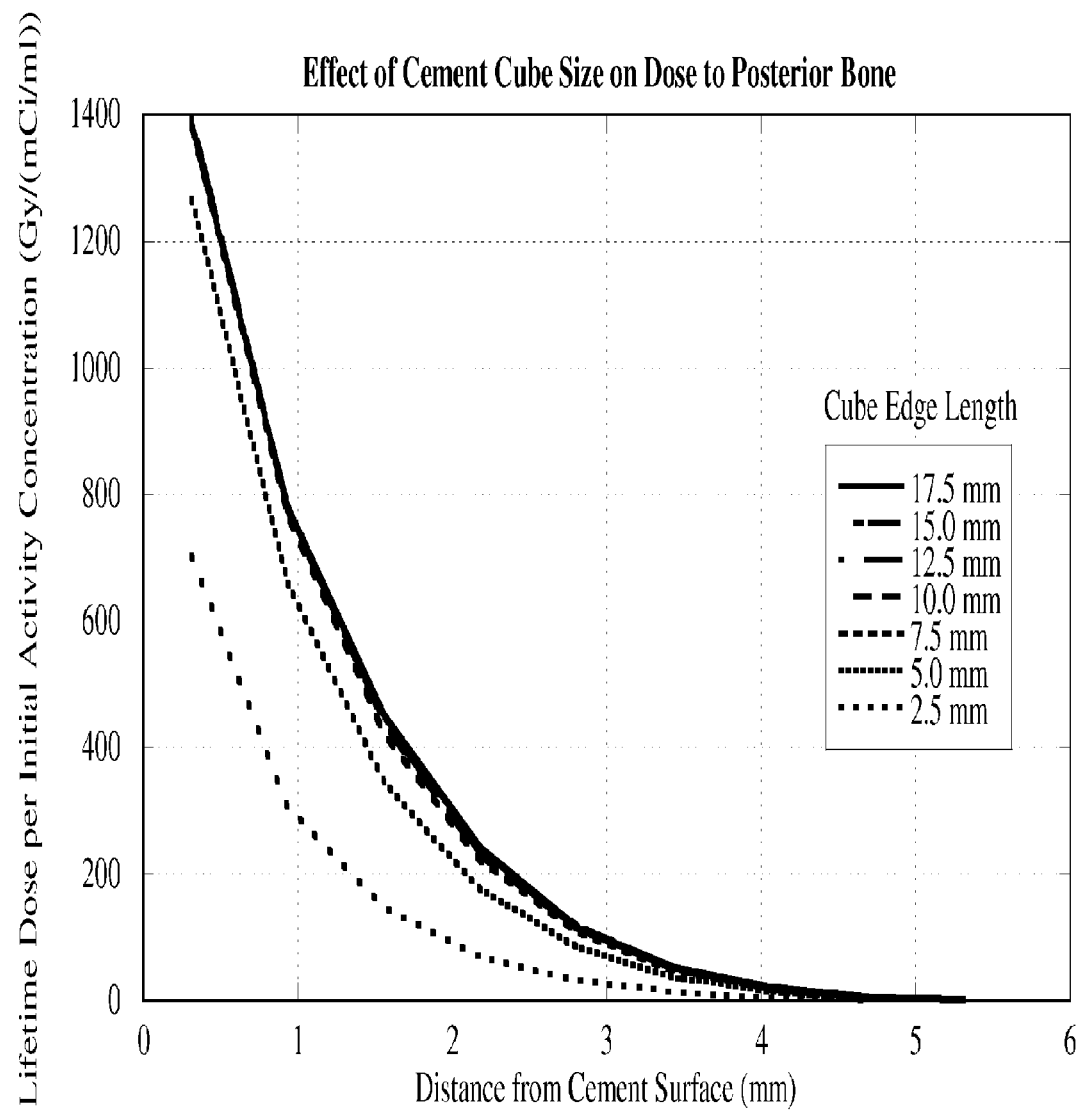
FIG. 8 depicts distributions of dose per initial activity concentration for the seven MCNP models containing various sizes of cubes of radioactive bone cement.

FIG. 8 illustrates distributions of dose per initial activity concentration for the seven MCNP models containing various sizes of cubes of radioactive bone cement. The dose distributions indicate that, as the cube size increases, the dose distribution in the target region approaches a constant value. This result demonstrates the limited range of beta radiation emitted from a P-32 source and indicates that source particles contribute to the dose distribution in a specific target region only when they originate within a certain distance from the target region. Subsequent analyses were performed on dose distributions per initial activity concentration, i.e., dose per mCi per unit volume of the cement.

The effect of cement shape on dose distribution was further characterized by creating 11 additional MCNP models in which only one of the dimensions of a hexahedral cement volume was varied. For all models, dose per initial activity concentration (Gy/(mCi/ml)) was analyzed in the same column of voxels as were analyzed for the cubic volumes of cement, regardless of which dimension was being varied (FIG. 9).

Figure 9:
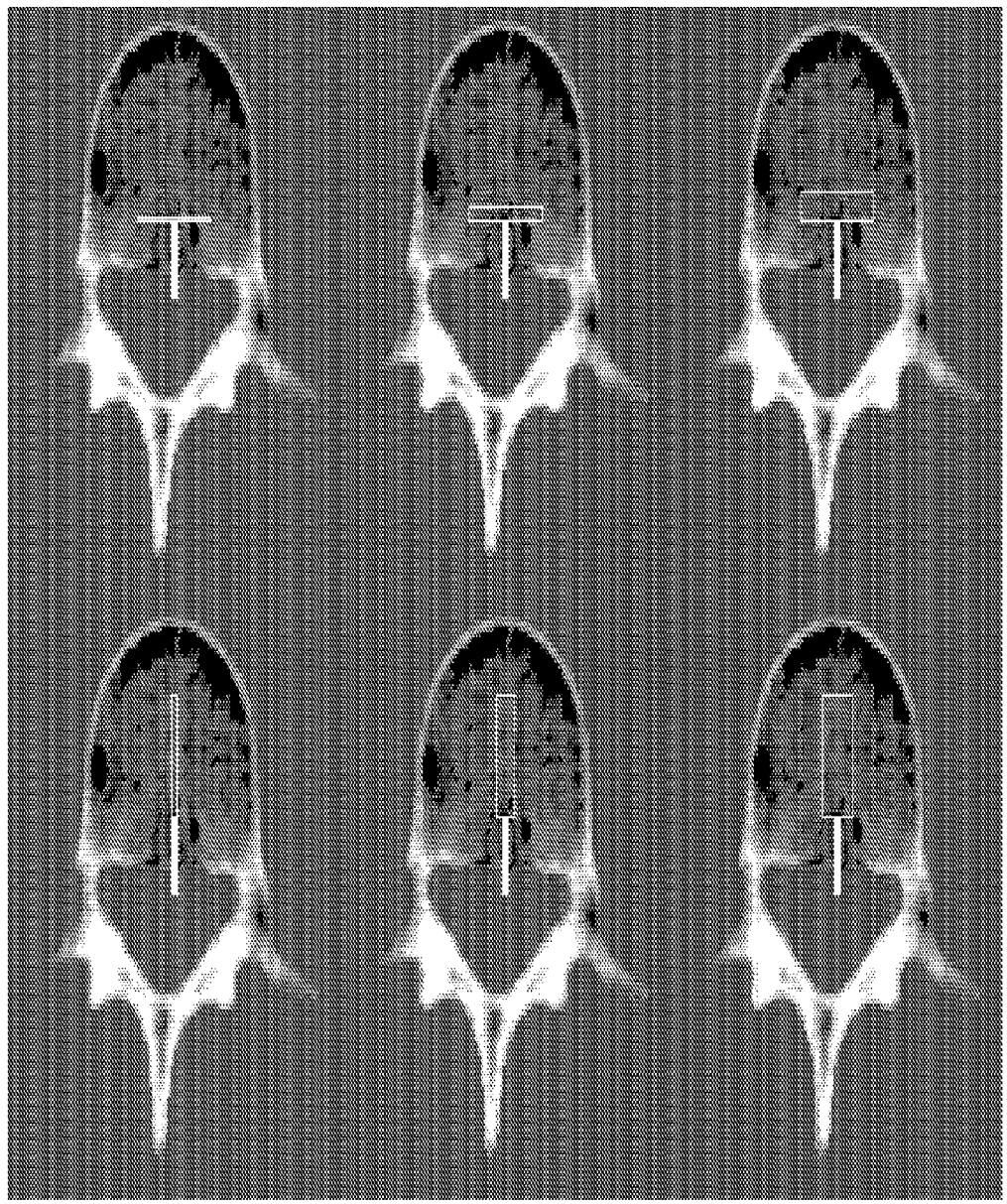
FIG. 9 depicts a transverse cross-section of the vertebra, showing outlines of three-dimensional hexahedrons of radioactive bone cement, of which one dimension was varied, and the voxels in which dose was determined.

FIG. 9 depicts a transverse cross-section of the L4 vertebra, showing outlines of three-dimensional hexahedrons of radioactive bone cement, of which one dimension was varied. Each hexahedron was based on the 15 mm edge-length cubic volume studied previously, with a 15 mm×15 mm face and various anterior depths (top) or lateral widths (bottom). Three of the five depths (0.625, 1.875, and 3.75 mm, top, left-to-right) and three of the six widths (1.25, 3.75, and 6.25 mm, bottom, left-to-right) are shown. The dose distribution was analyzed in the same region in each model, represented by the solid white columns.

Figure 10:
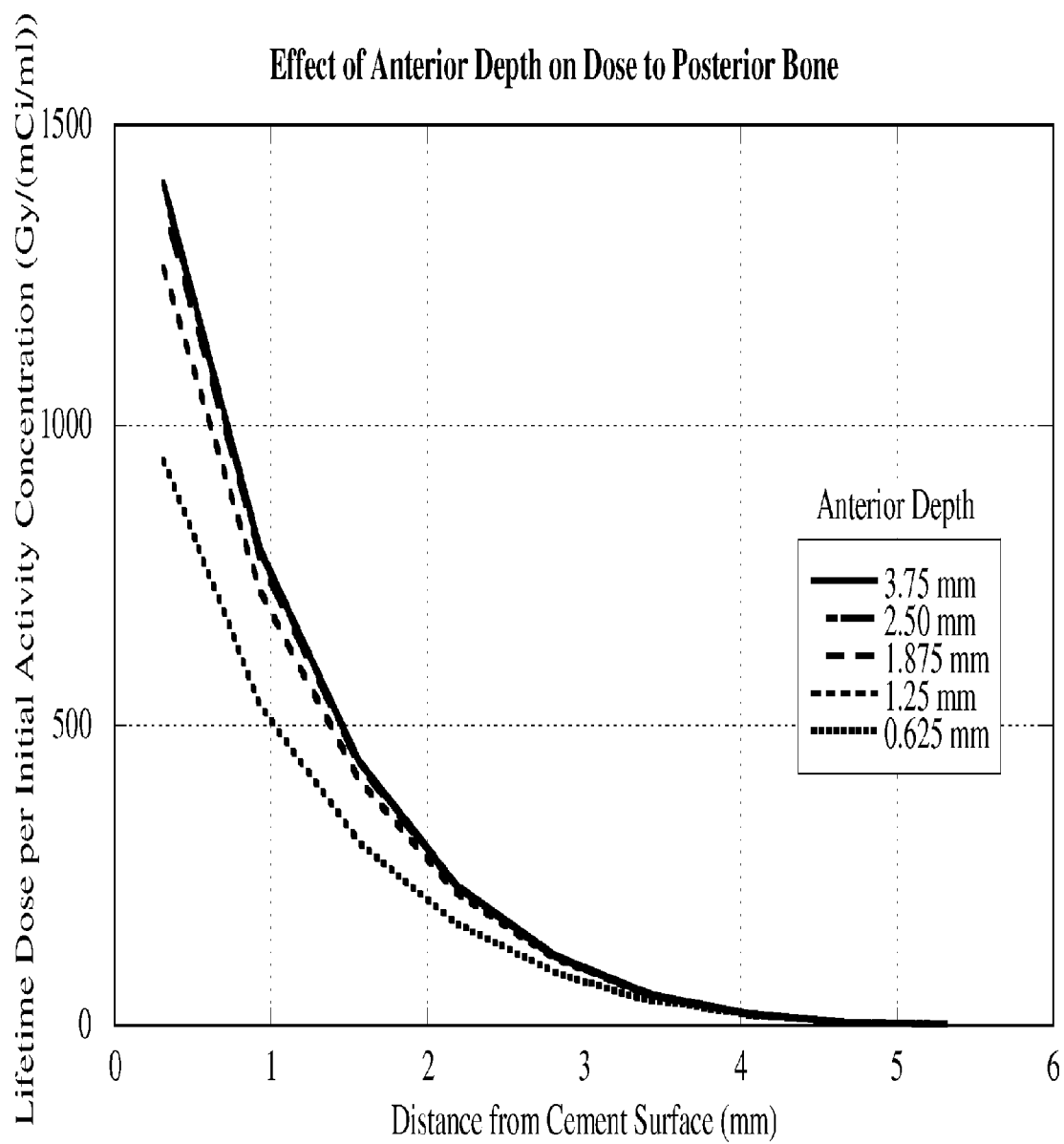
FIG. 10 depicts distributions of dose per initial activity concentration for the five MCNP models containing hexahedrons of radioactive bone cement with a 15 mm×15 mm face in the coronal plane and various anterior depths.

To analyze the effect of the anterior depth of the hexahedron, the dimensions of the 15 mm×15 mm face in the coronal plane were held constant, and depth in the anterior direction was varied (0.625, 1.25, 1.875, 2.5, and 3.75 mm) (FIG. 9, top). Illustrated in FIG. 10 are distributions of dose per initial activity concentration for the five MCNP models. For depths greater than 1.875 mm, the dose distribution curves are nearly identical (FIG. 10), indicating that there is a depth of the hexahedron beyond which additional source particles no longer contribute to the dose in the target region. This result demonstrates the shielding effect of the cement itself, and indicates that it is mainly the source particles generated near the surface of the volume that contribute to the target dose. Thus, only a thin layer of radioactive cement using a beta-emitter such as P-32 may be sufficient to produce the clinically-desired dose distribution in a given region of bone. Accordingly, some embodiments can include a first layer of substantially uniform distribution of radio-isotopes, and a second, internal layer that does not have the substantially uniform distribution.

Figure 11A:
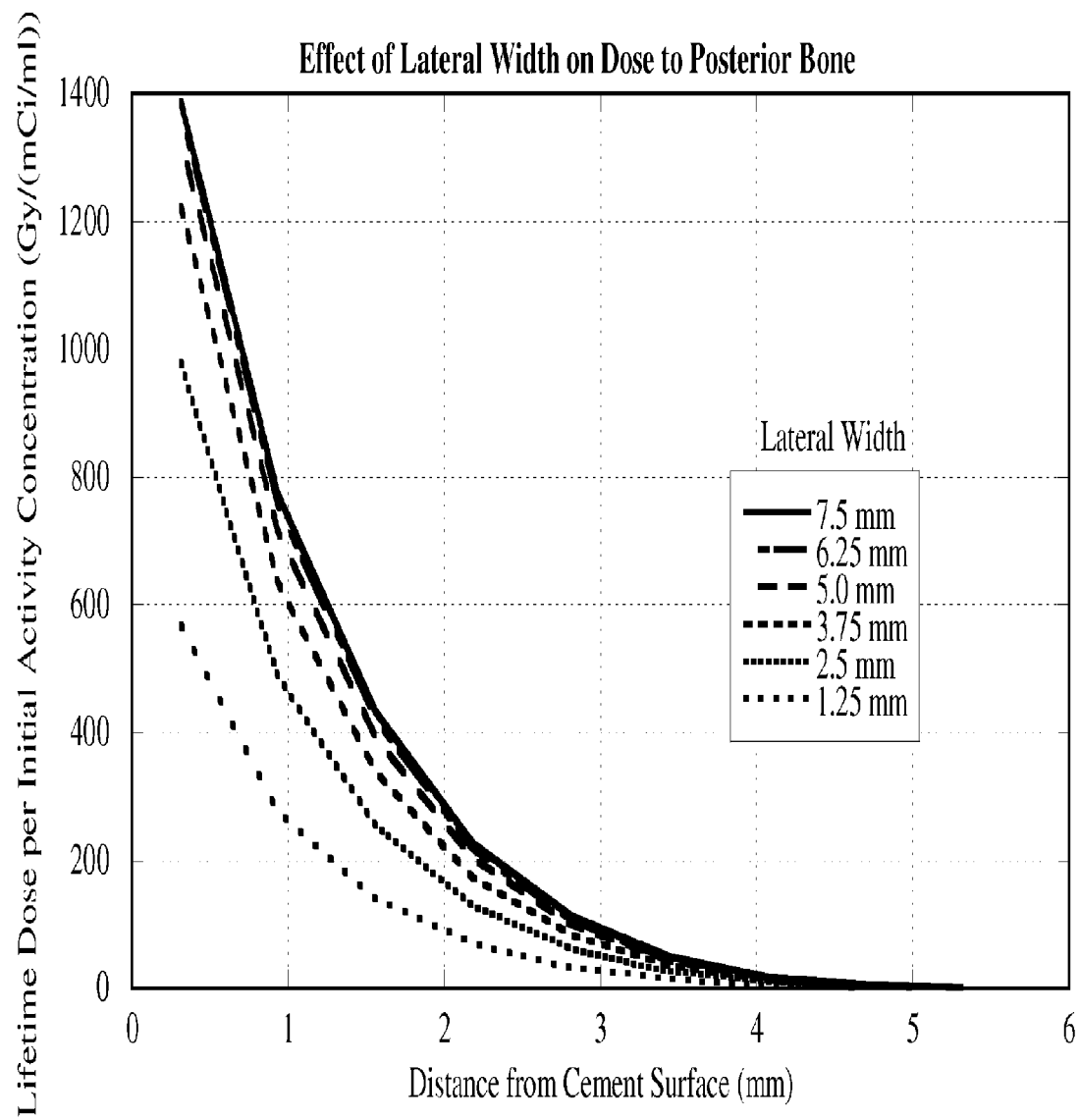
FIG. 11a depicts distributions of dose per initial activity concentration for the six MCNP models containing hexahedrons of radioactive bone cement with a 15 mm×15 mm face in the sagittal plane and various lateral widths.

To analyze the effect of the lateral width of the hexahedron, the dimensions of the 15 mm×15 mm face in the sagittal plane were held constant, and width in the lateral direction was varied (1.25, 2.5, 3.75, 5.0, 6.25, and 7.5 mm) (FIG. 9, bottom). FIG. 11a illustrates distributions of dose per initial activity concentration for these MCNP models. For widths greater than 6.25 mm, the dose distribution curves are nearly identical (FIG. 11), indicating that there is a width of the hexahedron beyond which additional source particles no longer contribute to the dose in the target region. This result demonstrates the range of source particles within the bone, as source particles generated a certain distance to either side (half the lateral width of the hexahedron) never reach the target region and do not contribute to its dose distribution. This may be a less clinically-relevant result than the effect of the anterior depth of the hexahedron, since it is unlikely that the clinical target region will be as narrow as the column of voxels examined here. Thus, source particles generated too far to the side of one target region will still likely contribute to the dose distribution in adjacent target regions.

The relationship between dose and cement volume for a constant activity concentration was further established using MCNP models of P-32 radioactive bone cement surrounded by a uniform distribution of bone. The density of the surrounding bone was 1.22 g/cm$^3$, representing typical human vertebral trabecular bone. Other densities would yield analogous results. Models were created for cylinders, spheres, and cubes of radioactive cement, as explained in the following examples.

For cylindrical cement volumes, a cylinder height of 2 cm and diameters (d) from 2.5 mm to 30 mm were evaluated. Tallies were obtained in concentric cylindrical shells of bone (each measuring 0.625-mm thick and 2-cm tall), located concentrically about the cement cylinder. For spherical cement volumes, diameters (d) from 2.5 mm to 30 mm were evaluated. Tallies were obtained in concentric spherical shells of bone (each measuring 0.625-mm thick), located concentrically about the cement sphere. For cubic cement volumes, edge lengths (L) from 2.5 mm to 25 mm were evaluated. Tallies were obtained in a layer of bone 0.625-mm-thick×L×L hexahedrons placed on one face of the cement cube.

For spherical cement volumes, diameters (d) from 2.5 mm to 30 mm were evaluated. Tallies were obtained in concentric spherical shells (each measuring 0.625-mm thick), located concentrically about the cement sphere. For cubic cement volumes, edge lengths (L) from 2.5 mm to 25 mm were evaluated. Tallies were obtained in a layer of 0.625-mm-thick×L×L hexahedrons placed on one face of the cement cube. The density of the surrounding bone was 1.22 g/cm$^3$, representing typical human vertebral trabecular bone. Other densities would yield analogous results. Moreover, although this analysis was performed for P-32, one skilled in the art would further recognize that analogous results may be obtained for other beta emitters or gamma emitters.

Figure 11B:
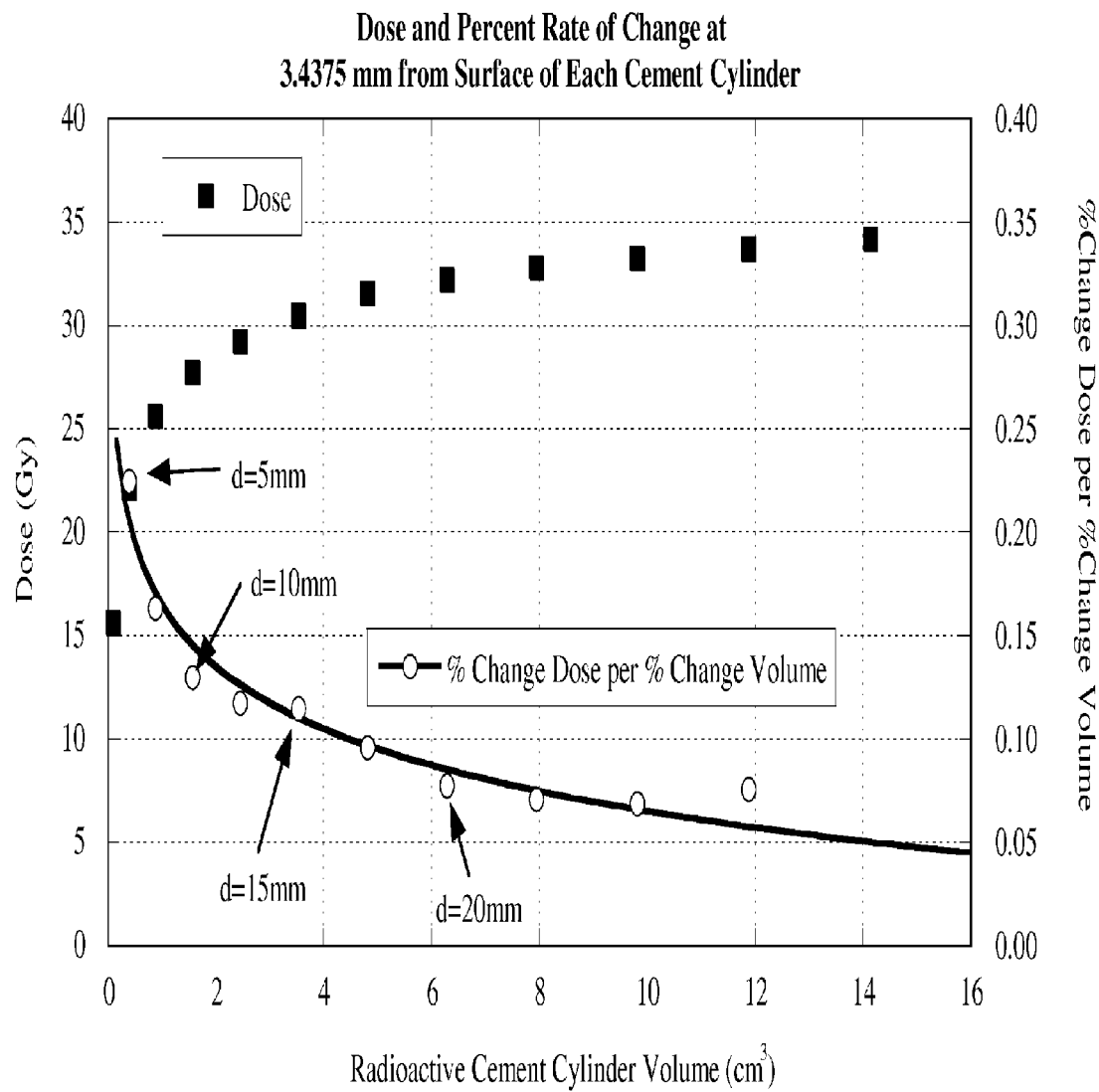
FIG. 11b depicts a plot of dose and percent change in dose per percent change in volume as a function of cement cylinder volume at a fixed distance from the surface of each cement cylinder.
Figure 11C:
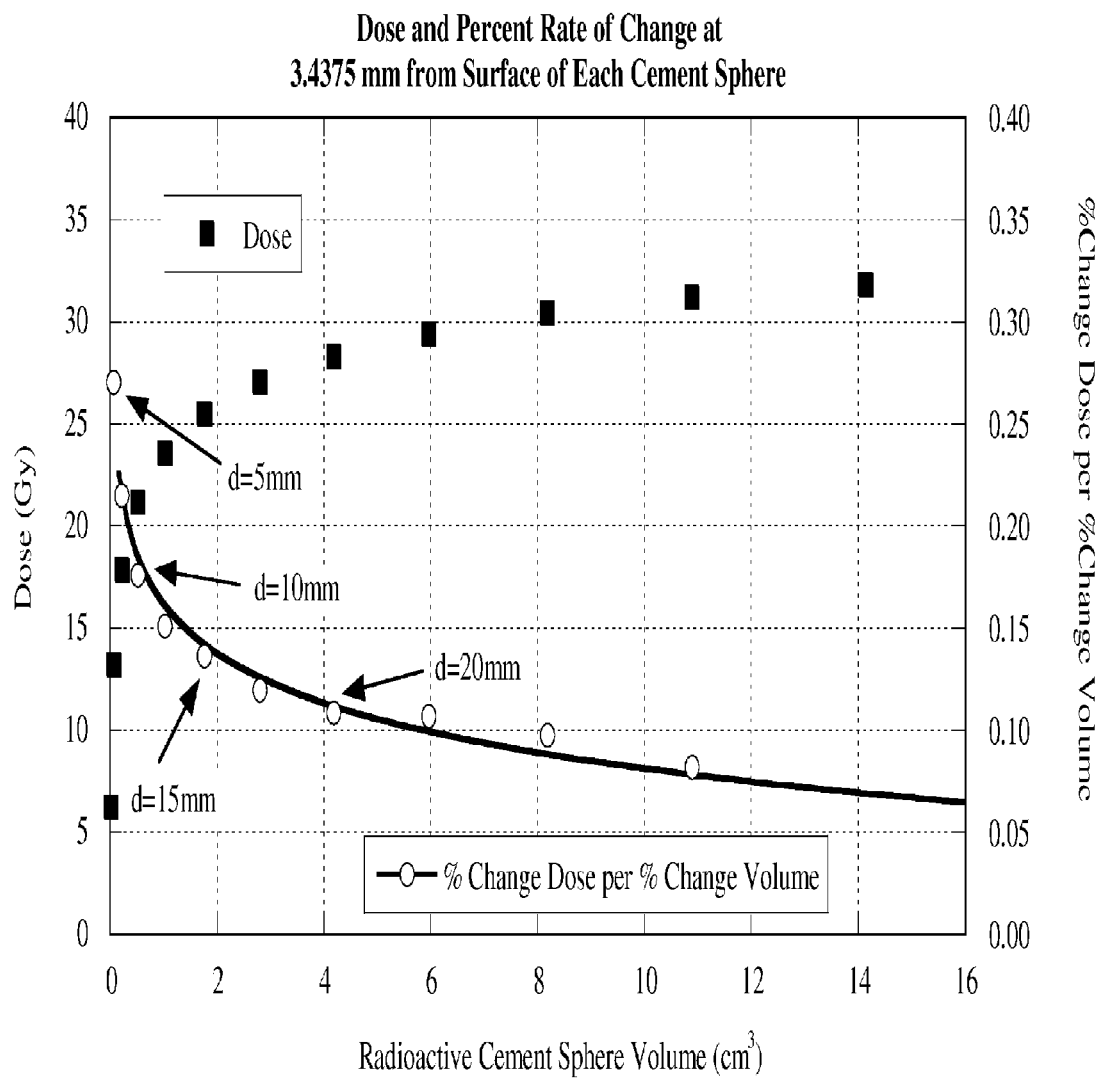
FIG. 11c depicts a plot of dose and percent change in dose per percent change in volume as a function of cement sphere volume at a fixed distance from the surface of each cement sphere.
Figure 11D:
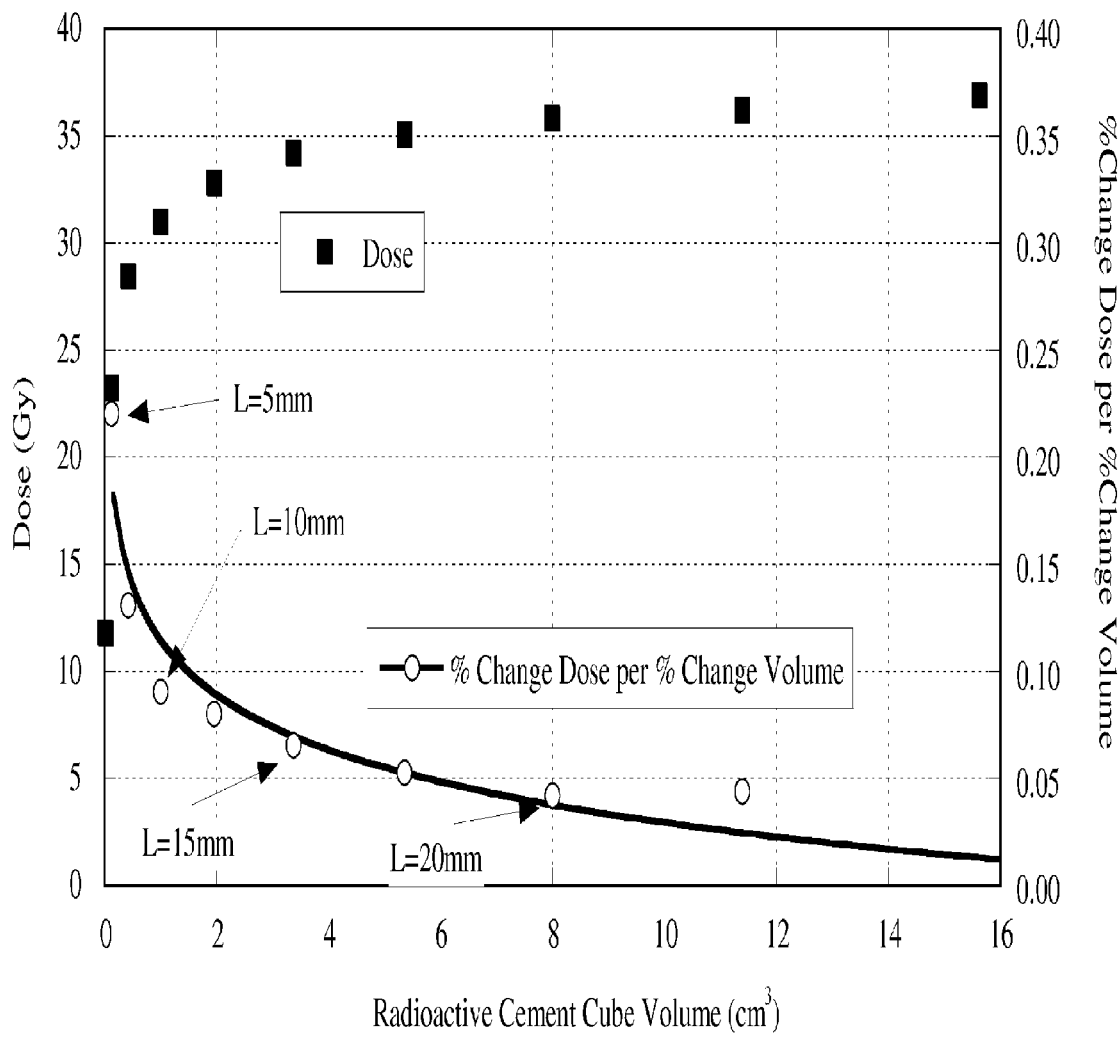
FIG. 11d depicts a plot of dose and percent change in dose per percent change in volume as a function of cement cube volume at a fixed distance from the surface of each cement cube.

Tally results were used to create depth-dose curves (lifetime dose versus distance from the surface of the cement volume) for each model, assuming an initial activity concentration of 1 mCi per ml of cement. Total activity is proportional to cement volume for a constant activity concentration. The computed dose at fixed distances of 2.1875, 3.4375, and 4.0625 mm (the center of the fourth, sixth, and seventh tallies from the cement surface, respectively) was plotted against cement volume, and the results for a distance of 3.4375 mm are shown in FIGS. 11b-11d. This range of distances was selected because the computed dose over this range approximates a therapeutic dose for initial activity concentrations of between 0.2-4 mCi per mL of cement. Results for dose at other distances would be analogous. For example, in some embodiments, the distance ranges from about 3 mm to about 4 mm. In some embodiments, the distance ranges from about 3.25 mm to about 3.75 mm. In some embodiments, the distance ranges from about 2 mm to about 5 mm. In some embodiments, the distance ranges from less than about 2 mm or greater than about 5 mm. For each distance, the central finite difference method was used to calculate the percent rate of change in dose per percent rate of change in volume (% Change Dose per % Change Volume) at each dose-volume data point (squares on FIGS. 11b-11d). % Change Dose per % Change Volume was then plotted against cement volume, and a logarithmic curve was fit to the data. FIGS. 11b-11d show the % Change Dose per % Change Volume data for a distance of 3.4375 mm, and the logarithmic curve fit for all three distances from the cement surface.

As shown in the plots of % Change Dose per % Change Volume versus cement volume, for all three cement shapes, increasing the implanted volume of radioactive cement, which increases the total implanted initial activity, does not yield a proportional increase in the dose at a fixed distance from the cement surface (3.4375 mm in FIGS. 11b-11d). (In the case of the cement cylinder, increasing the volume was due solely to increasing the cylinder diameter, as the cylinder height remained constant.) Thus, unlike a conventional brachytherapy implant, the dose from P-32 radioactive bone cement does not necessarily depend on the total implanted activity. Furthermore, as the implanted radioactive cement volume increases, the dose at a fixed distance from the cement surface approaches a constant, maximum value. The low sensitivity of dose to changes in volume is indicated by % Change Dose per % Change Volume and is similar for all of the analyzed shapes and at all three distances from the cement surface. These shapes are clinically relevant because each individual shape or a combination of multiple shapes (cylinders, spheres and/or cubes) can be used to approximate the shape of actual radioactive cement implants. For example, in some embodiments, cylinders can be combined with cubes, spheres, other cylinders and/or other shapes; cubes can be combined with cylinders, spheres, other cubes and/or other shapes; and spheres can be combined with cylinders, cubes, other spheres and/or other shapes.

These results make it possible to base guidelines for treatment of bone metastases with radioactive cement solely on the activity concentration of the cement rather than on the total implanted activity. For example, for a clinically-relevant cement volume of about 2 cm$^3$, % Change Dose per % Change Volume ranges from 0.085-0.155 for all cement shapes and distances from the cement surface (FIGS. 11b-11d, Table 5). Then, for a maximum allowable % Change Dose of 10% (the maximum deviation from the prescribed dose for a clinical treatment), the corresponding maximum allowable % Change Volume would range from 65-118%. Thus, when the anticipated initial cement volume is 2 cm$^3$, regardless of cement shape, an actual volume of up to 3.3-4.4 cm$^3$ could be implanted without changing the dose by more than 10%. Examples for other initial cement volumes can be found in Table 5, where the range of % Change Volume for each initial volume is indicated with bold type.

TABLE 5

| Cement Shape | Initial Volume (cm$^3$) | % Change Dose per % Change Volume at Various Distances | | | Maximum Allowable % Change Volume for % Change Dose = 10% | | |
|---|---|---|---|---|---|---|---|
| | | 2.1875 mm | 3.4375 mm | 4.0625 mm | 2.1875 mm | 3.4375 mm | 4.0625 mm |
| Cylinder | 0.5 | 0.19 | 0.195 | 0.2 | 53% | 51% | 50% |
| Sphere | 0.5 | 0.175 | 0.19 | 0.195 | 57% | 53% | 51% |
| Cube | 0.5 | 0.14 | 0.14 | 0.14 | 71% | 71% | 71% |
| Cylinder | 1 | 0.155 | 0.165 | 0.175 | 65% | 61% | 57% |
| Sphere | 1 | 0.145 | 0.165 | 0.175 | 69% | 61% | 57% |
| Cube | 1 | 0.115 | 0.115 | 0.115 | 87% | 87% | 87% |
| Cylinder | 2 | 0.12 | 0.135 | 0.145 | 83% | 74% | 69% |
| Sphere | 2 | 0.12 | 0.14 | 0.155 | 83% | 71% | 65% |
| Cube | 2 | 0.085 | 0.09 | 0.09 | 118% | 111% | 111% |
| Cylinder | 3 | 0.1 | 0.115 | 0.13 | 100% | 87% | 77% |
| Sphere | 3 | 0.1 | 0.125 | 0.145 | 100% | 80% | 69% |
| Cube | 3 | 0.07 | 0.075 | 0.075 | 143% | 133% | 133% |
| Cylinder | 5 | 0.075 | 0.095 | 0.11 | 133% | 105% | 91% |
| Sphere | 5 | 0.08 | 0.105 | 0.125 | 125% | 95% | 80% |
| Cube | 5 | 0.05 | 0.055 | 0.055 | 200% | 182% | 182% |

Additional MCNP models were analyzed to demonstrate that the relative independence of dose on cement volume (and therefore activity) is due to the attenuation properties of the cement matrix material, and is not simply due to the distribution of the radioisotope. These models were identical to the models described above, with the exception that the radioactive source was P-32 uniformly distributed within a cylindrical volume of air instead of bone cement.

Figure 11E:
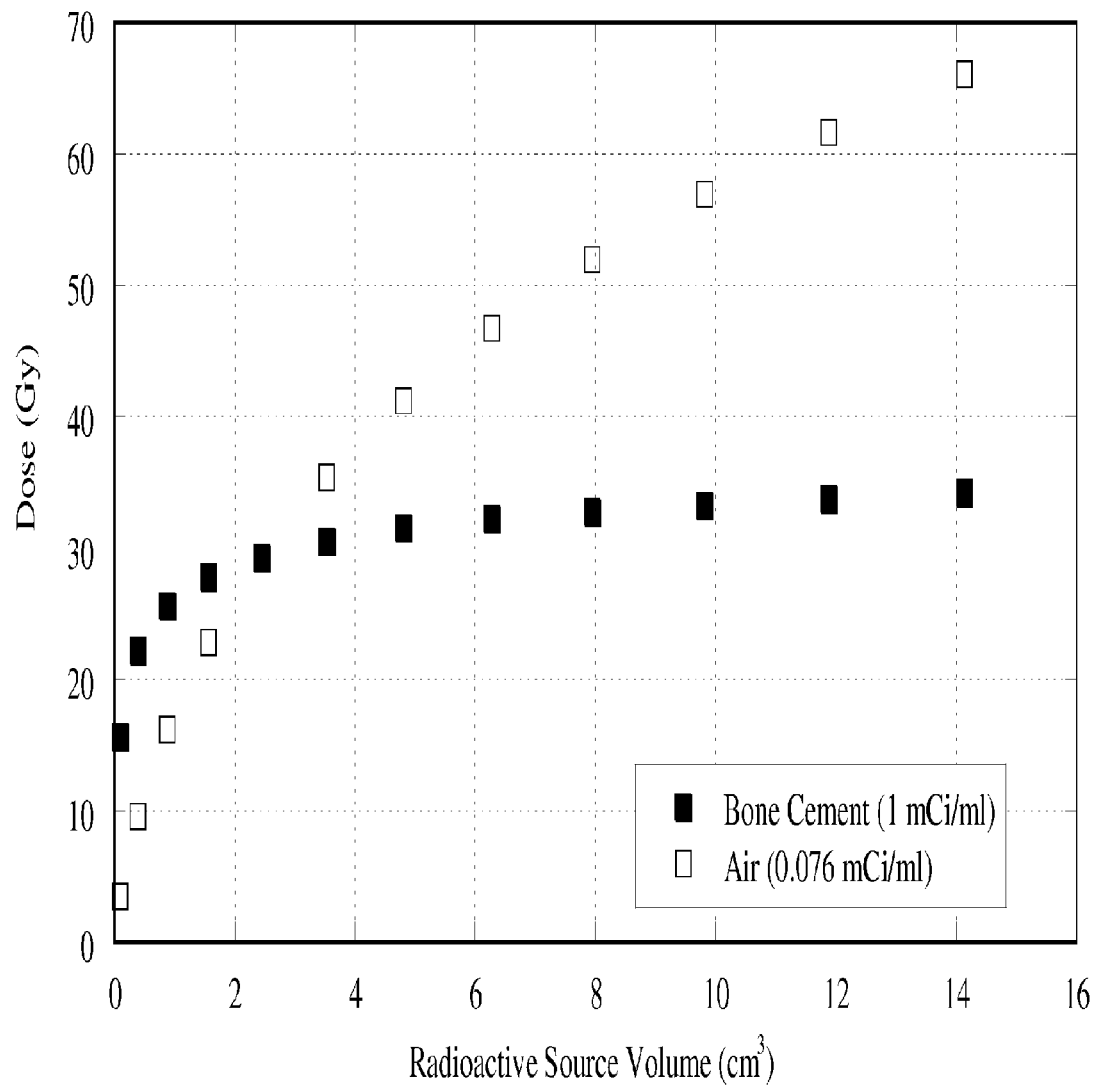
FIG. 11e depicts a plot of dose as a function radioactive source volume, at a fixed distance, for air and for bone cement as matrix materials.
Figure 11F:
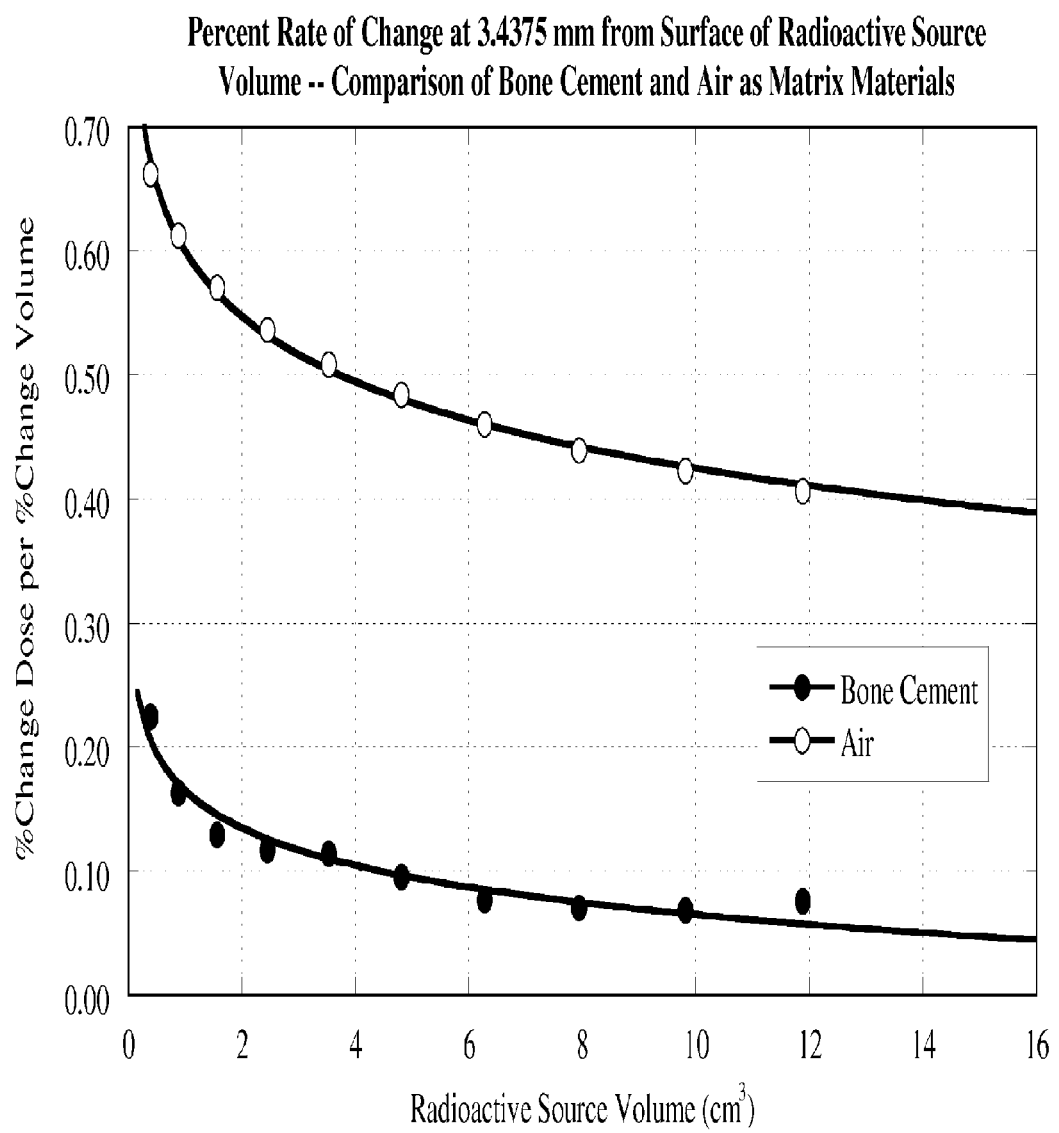
FIG. 11f depicts a plot of percent change in dose per percent change in volume as a function radioactive source volume, at a fixed distance, for air and for bone cement as matrix materials.

Without the shielding effect of the bone cement, a greater proportion of the radiation from P-32 escapes the source volume of air and is deposited within the surrounding bone. Thus, to facilitate comparison of P-32 in air with P-32 in bone cement, the activity concentration for P-32 in air was scaled so that both P-32 in air and P-32 in bone cement delivered the same dose (29 Gy) at 3.4375 mm for a clinically relevant source volume of 2.5 ml. The results are shown in FIGS. 11e and 11f. Unlike the behavior for P-32 in bone cement, the dose at 3.4375 mm for P-32 in air does not approach a maximum value and, in fact, continuously increases with increasing source volume, as shown in FIG. 11e. These results demonstrate that the dose from P-32 in bone cement is relatively insensitive to source volume (and therefore total activity) and that this characteristic can be attributed to the attenuation properties of the bone cement.

Figure 11G:
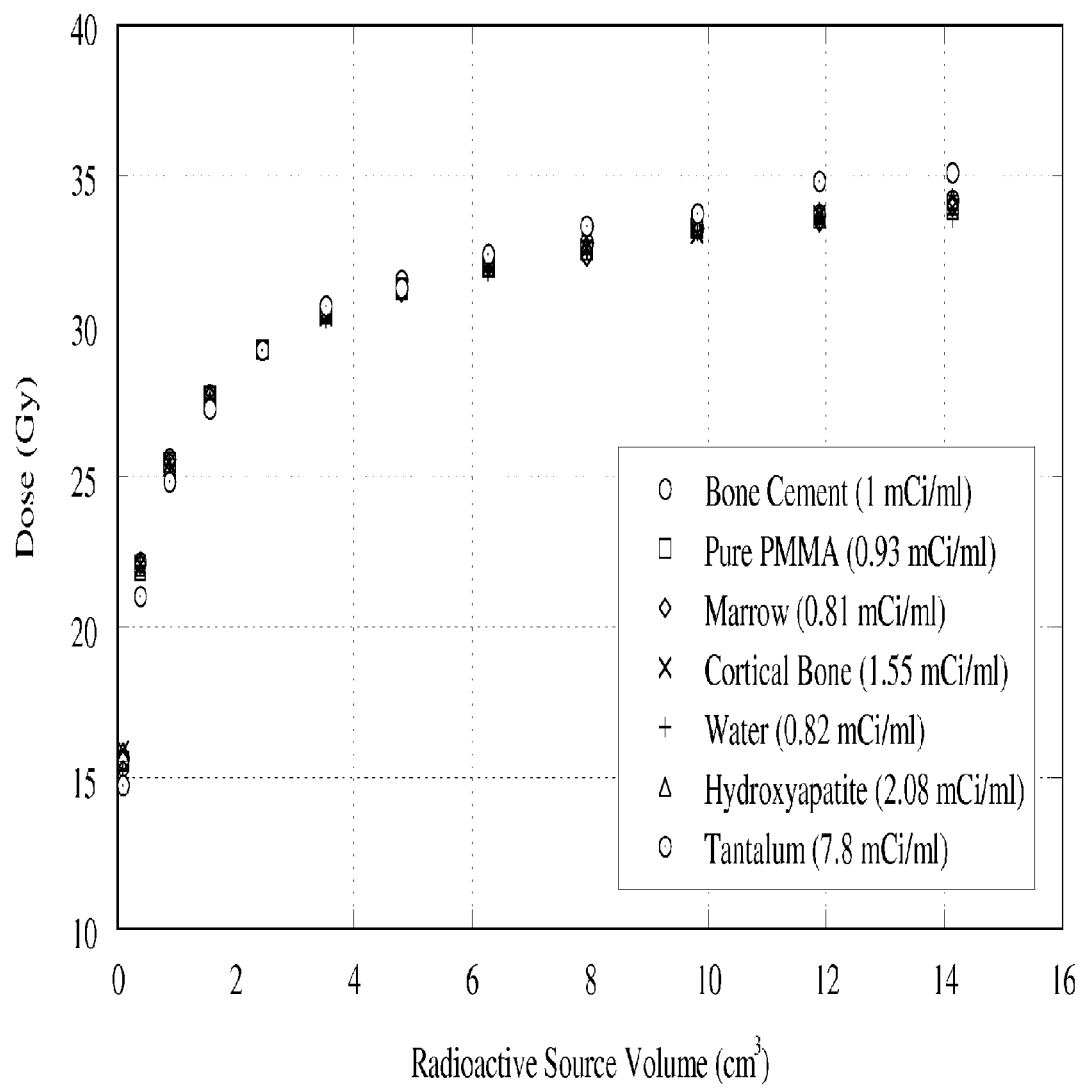
FIG. 11g depicts a plot of dose as a function radioactive source volume, at a fixed distance, for various matrix materials.
Figure 11H:
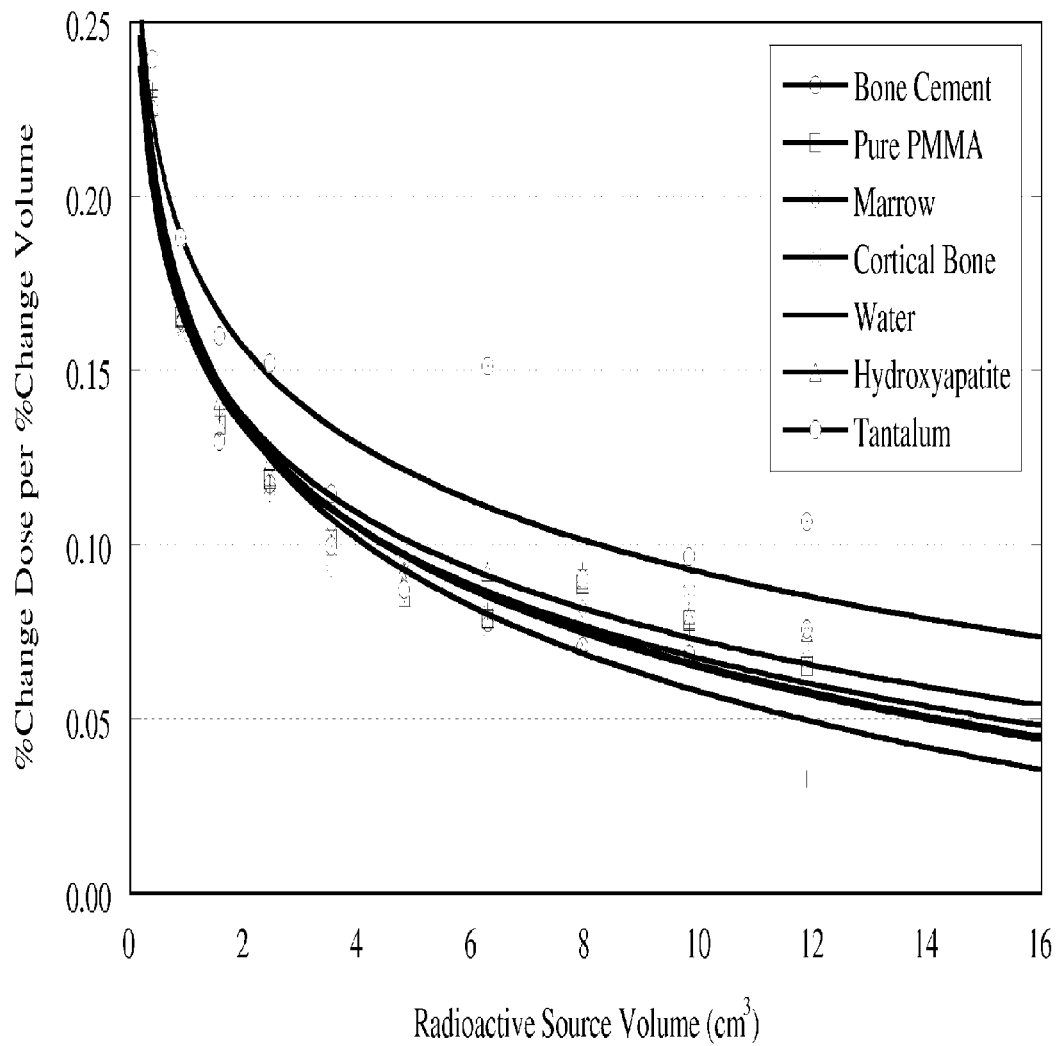
FIG. 11h depicts a plot of percent change in dose per percent change in volume as a function radioactive source volume, at a fixed distance, for various matrix materials.

Finally, MCNP models were analyzed to demonstrate this characteristic for P-32 in other matrix materials, as shown in FIGS. 11g and 11h. These models were identical to the cylinder source models described above, with P-32 modeled as uniformly distributed within a cylindrical volume of pure polymethylmethacrylate (PMMA, no barium sulfate added), marrow, solid cortical bone, water, hydroxyapatite, and tantalum. The density of the surrounding bone was 1.22 g/cm$^3$, representing typical human vertebral trabecular bone. Other densities would yield analogous results.

As before, the activity concentration in each matrix material was scaled so that the same dose (29 Gy) at 3.4375 mm was delivered for a source volume of 2.5 ml. The resulting dose-volume curves and % Change Dose per % Change Volume versus volume curves are very similar for every matrix material (FIGS. 11g and 11h). These results indicate that the relative independence of dose from total activity is a characteristic of P-32 uniformly distributed within a wide range of matrix materials, from low-density marrow (0.98 g/cm$^3$) to high-density tantalum (16.7 g/cm$^3$). The materials examined here are not all-inclusive and were selected to illustrate that a number of matrix materials, some of which may have biologically, structurally, or otherwise useful features, could be mixed with a beta-emitting radioisotope to achieve relative independence of dose on volume. The resulting mixture may be a cement, a putty-like material that is shaped and pressed into place, a liquid or powder contained in a balloon or bag, etc. Once placed in the body, the dose to the target would be relatively independent of the volume or shape of the material.

To determine the effect of different bone materials on the dose distribution of radioactive bone cement, eight MCNP models containing the 15 mm-edge-length cubic volume of radioactive bone cement were created, and all bone in the vertebra was modeled as a uniform distribution of a single bone material. In each model, all of the surrounding bone was assigned one of the material definitions in Table 1.

Figure 12:
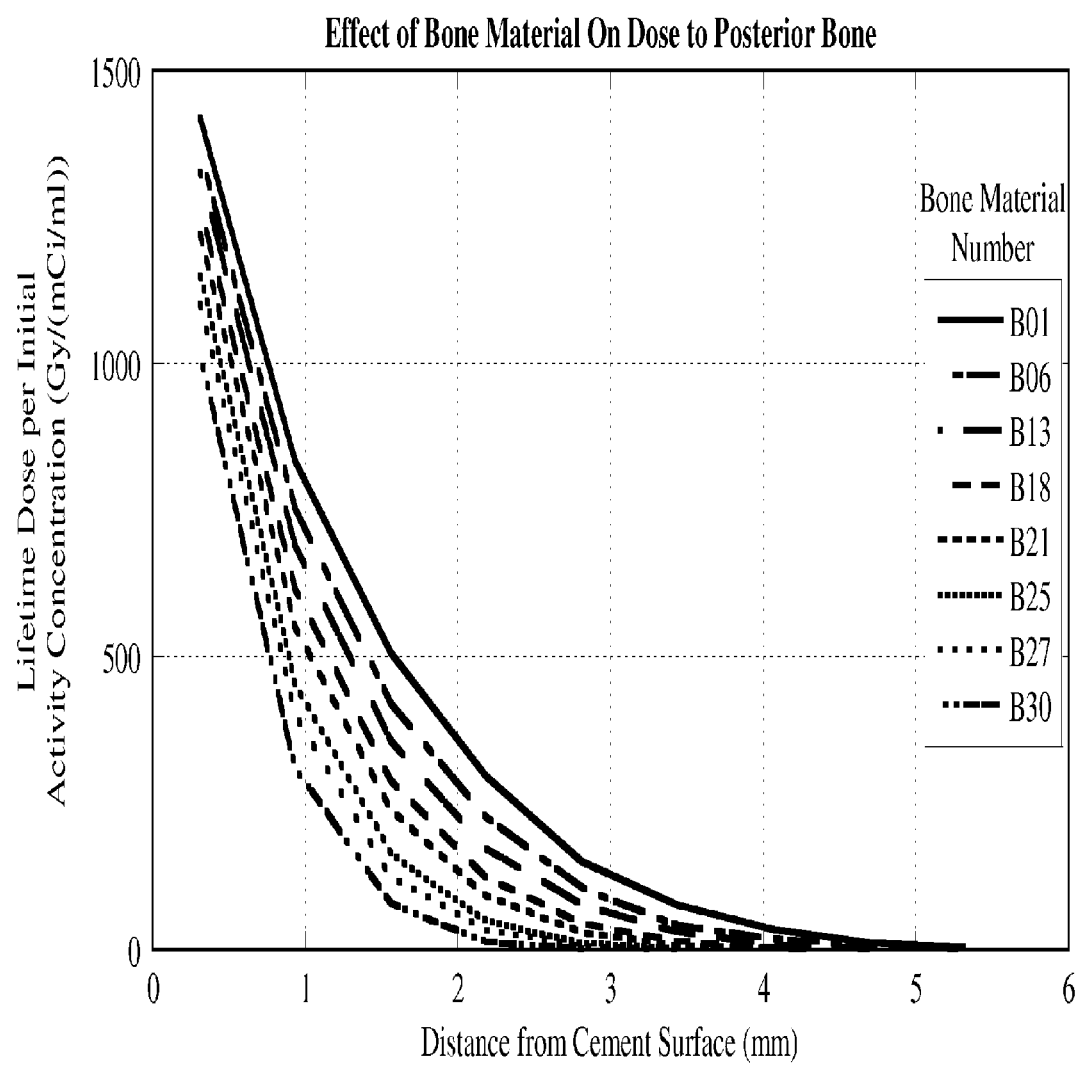
FIG. 12 depicts distributions of dose per initial activity concentration for the eight MCNP models containing a 15-mm cubic volume of radioactive bone cement with surrounding bone modeled as a uniform distribution of various bone materials.

The dose distribution curves for each model are shown in FIG. 12. As the cortical bone volume fraction of the surrounding bone material increases, the dose gradient becomes steeper, indicating that higher density bone attenuates the radiation to a greater extent than lower density bone. This may be a clinically important result since the cortical shell separating the vertebral body from the spinal canal would then be expected to enhance the shielding effect of the bone and prevent harmful radiation from reaching the spinal cord. This effect may also be important in determining dose requirements for targeting a tumor confined within the vertebral body if regions of very high density tissue (such as a blastic tumor) exist between the cement source and the targeted tumor.

Since bone material definitions include both atomic composition and density, the effect of bone material was further analyzed by independently varying atomic composition and density separately. Fourteen additional MCNP models of the 15 mm-edge-length cubic volume of radioactive bone cement were created, with bone material definitions based on material B13 (80.2% marrow/19.8% cortical bone, 1.221 g/cm$^3$ density), a bone material that was observed in the trabecular bone of the models of the vertebral body. In seven of the MCNP models, the density of the surrounding bone material was held constant while the atomic composition was varied among the atomic compositions of seven of the other eight material definitions used in Table 1. In the other seven MCNP models, the atomic composition of the surrounding bone material was held constant while the density was varied among the densities of the other seven materials.

Figure 13:
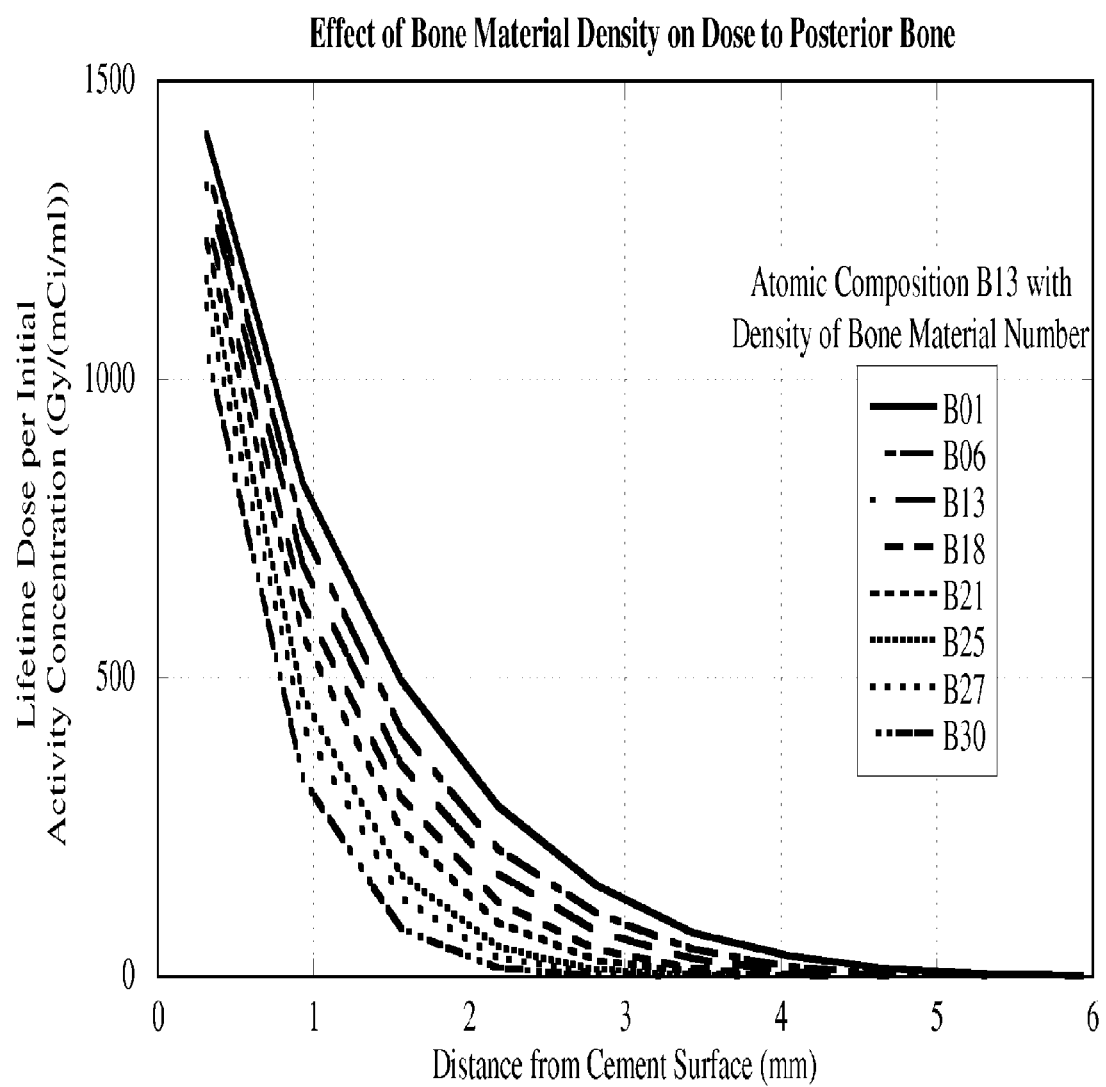
FIG. 13 depicts distributions of dose per initial activity concentration for the eight MCNP models containing a 15-mm cubic volume of radioactive bone cement with surrounding bone modeled as a uniform distribution of a material with a specific atomic composition and various densities.
Figure 14:
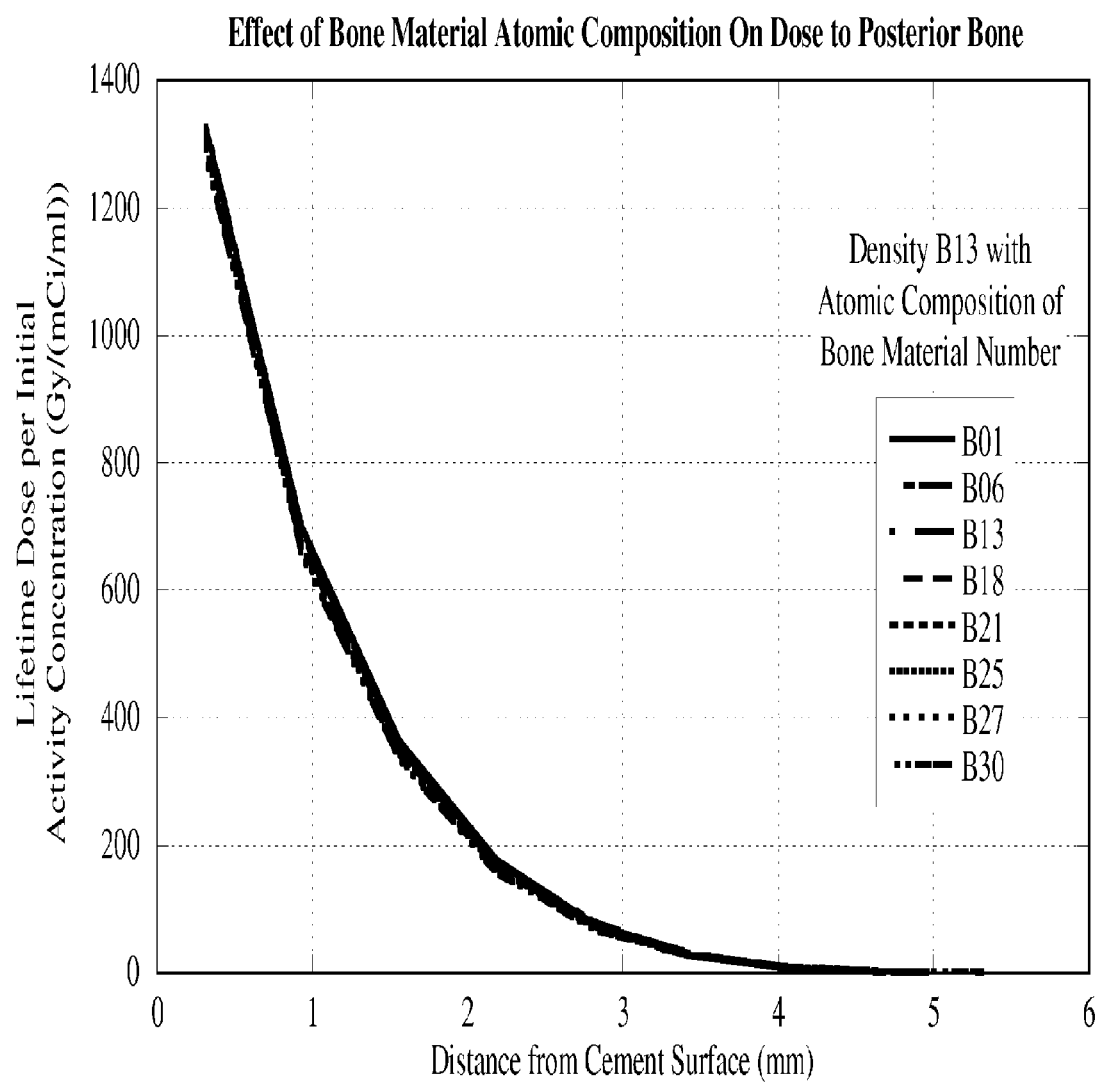
FIG. 14 depicts distributions of dose per initial activity concentration for the eight MCNP models containing a 15-mm cubic volume of radioactive bone cement with surrounding bone modeled as a uniform distribution of a material with a specific density and various atomic compositions.

The dose distribution curves for each of these models is shown in FIG. 13 and FIG. 14. When the atomic composition is held constant and the material density is varied, the dose distributions resemble those in FIG. 12, in which both the atomic composition and density of the bone materials were varied (FIG. 13). However, when the density is held constant and the atomic composition is varied, the dose distributions are virtually identical to each other (FIG. 14). Thus, it can be concluded that the observed differences in dose distributions in FIG. 12 are mostly due to the difference in density, rather than atomic composition, between the different bone materials. This result may be useful for evaluation of model accuracy, as it indicates that the modeling method is more sensitive to changes in density than it is to changes in atomic composition.

Since P-32 can be activated using a number of different methods, some of which may produce additional radioisotopes, it is necessary to determine the effect of the actual composition of the radioactive compound on dose distribution. The MCNP models described to this point have assumed a pure P-32 radioactive source, which would be the case for a compound that is synthesized with P-32. However, a P-32 source that is also under consideration is manufactured in a way that produces trace amounts of calcium-47 (Ca-47, 4.5 day half-life) and its daughter scandium-47 (Sc-47, 3.4 day half-life). To determine the effect of the presence of additional radioisotopes on the predicted dose distribution, two additional MCNP models were created and analyzed, in which the 15 mm-edge-length cubic volume of radioactive bone cement modeled above contained Ca-47 and Sc-47 source definitions. The resulting dose distributions were added to the P-32 dose distributions, taking into account the half-life of each radioisotope and its relative initial activity (0.6 μCi of each radioisotope per 1 mCi of P-32).

Figure 15:
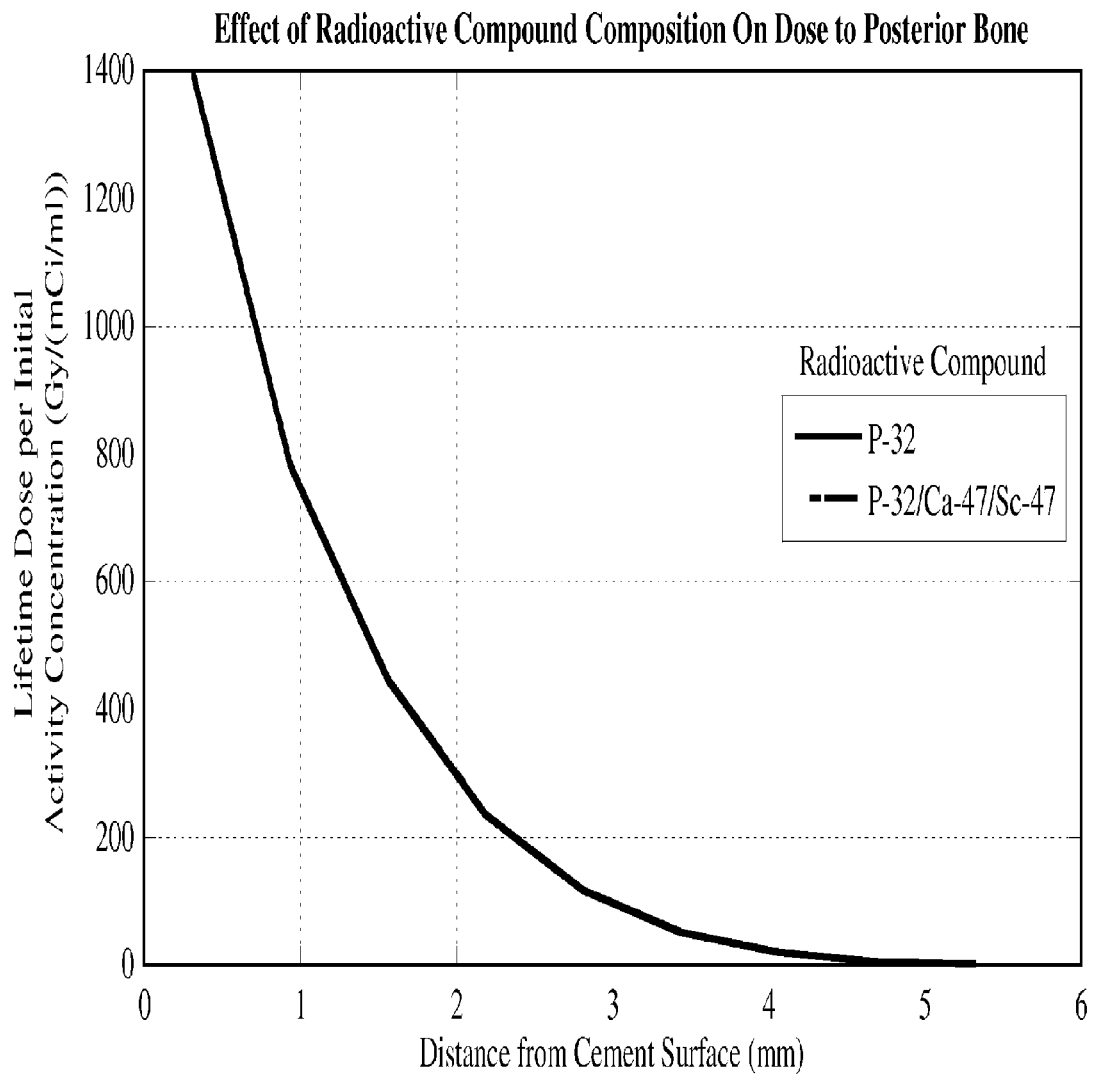
FIG. 15 depicts distributions of dose per initial activity concentration for the two MCNP models containing a 15-mm cubic volume of radioactive bone cement with either a pure P-32 radioactive source or a P-32/Ca-47/Sc-47 radioactive compound source.

There was no visible difference in the dose distributions for the pure P-32 radioactive source and the P-32/Ca-47/Sc-47 radioactive source (FIG. 15). Although both Ca-47 and Sc-47 decay with a small amount of gamma emissions, their initial activities relative to P-32 are extremely small and their half-lives are relatively short, resulting in a negligible effect on the dose distribution of the entire compound. Although this effect can be confirmed for additional radioactive compounds, it is likely that other methods of synthesizing P-32 as the primary radioisotope would yield similarly insignificant quantities of compound impurities.

To determine the effect on dose distribution of the specific type of bone cement used, four additional MCNP models of the 15 mm-edge-length cubic volume of radioactive bone cement modeled above were created and analyzed. In these models, the original P-32 radioisotope source was uniformly distributed within several types of bone cement commonly used in orthopaedic procedures. Three models examined bone cements used in the vertebroplasty and kyphoplasty procedures that radioactive bone cement would be used with to treat spinal metastases: ArthroCare Parallax® Bone Cement, ArthroCare Parallax® Bone Cement with TRAC-ERS® Bone Cement Opacifier, and Stryker Spineplex® Bone Cement. Additionally, one model examined Stryker Surgical Simplex® P Bone Cement, which might be used in a percutaneous hip repair procedure. Although these brands are very similar polymethylmethacrylate bone cements, their exact compositions vary.

Figure 16:
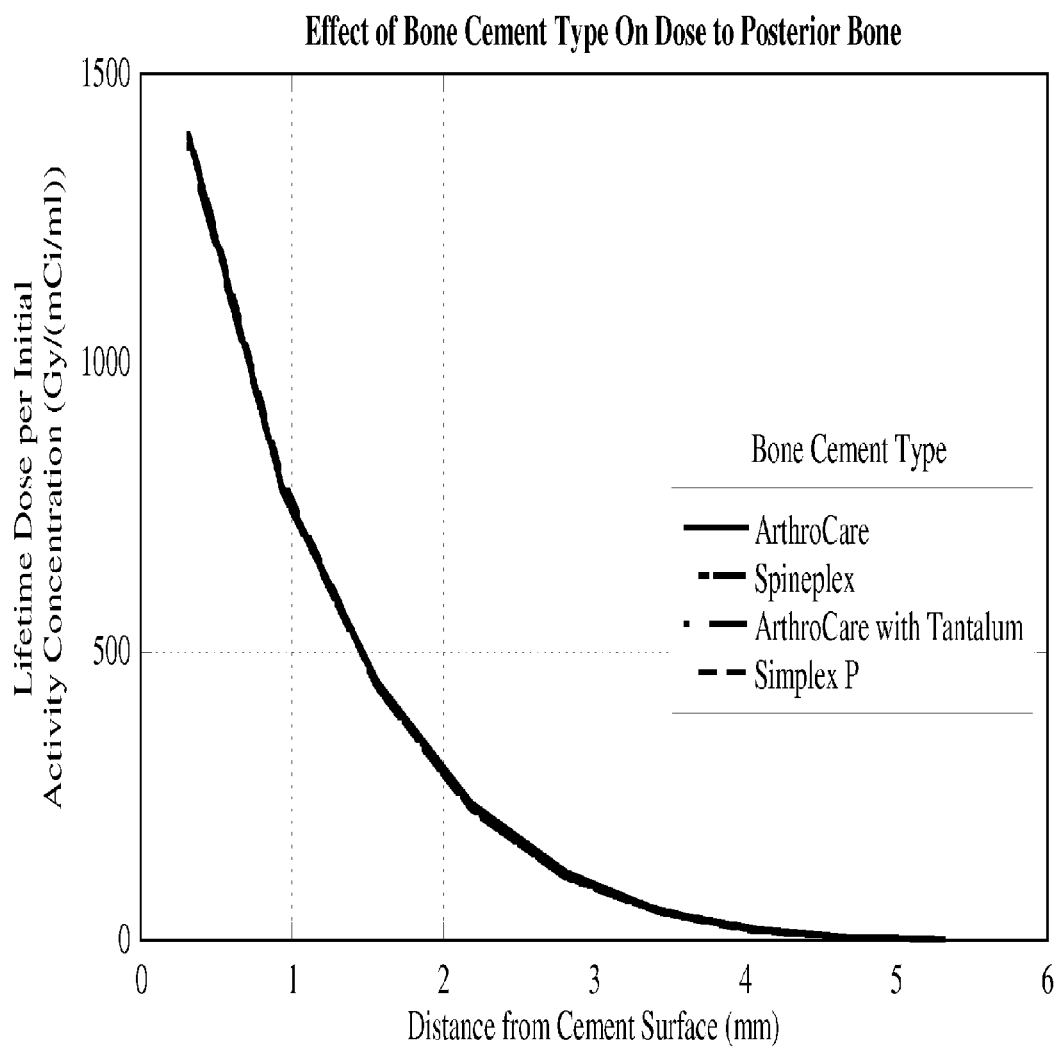
FIG. 16 depicts distributions of dose per initial activity concentration for the four MCNP models containing a 15-mm cubic volume of P-32 uniformly distributed within various bone cement types.

The dose distributions curves for each model are virtually identical (FIG. 16), indicating that variations in the composition of each of the analyzed bone cements do not have a significant effect on the resulting dose distributions. Given the similarity in atomic composition for each of these bone cement formulations, this result is to be expected. Although it would be necessary to confirm this effect for additional bone cements, most PMMA bone cement formulations are very similar and likely would not significantly affect the resulting dose distribution, meaning that the clinical feasibility of radioactive bone cement is likely independent of the specific type of PMMA used.

In some embodiments, the method for treating a target tissue includes identifying a vertebral tumor; determining its distance from the cement that would be injected during vertebroplasty; and, based on a dose-to-depth parameter, determining the activity concentration to deliver a target dose at a specified distance from the surface of the cement. Accordingly, as the vertebral tumor is within the specified distance from the surface of the cement, additional activity contained within cement delivered elsewhere within the vertebral body will not affect the dose distribution in the target tissue.

Dose distributions predicted using the radiation transport modeling method developed were compared to those measured experimentally with radiochromic film. As necessary, experimental sources of error were identified and the Monte Carlo models were modified until the predicted and measured dose distributions agreed within the experimental uncertainty.

Figure 17:
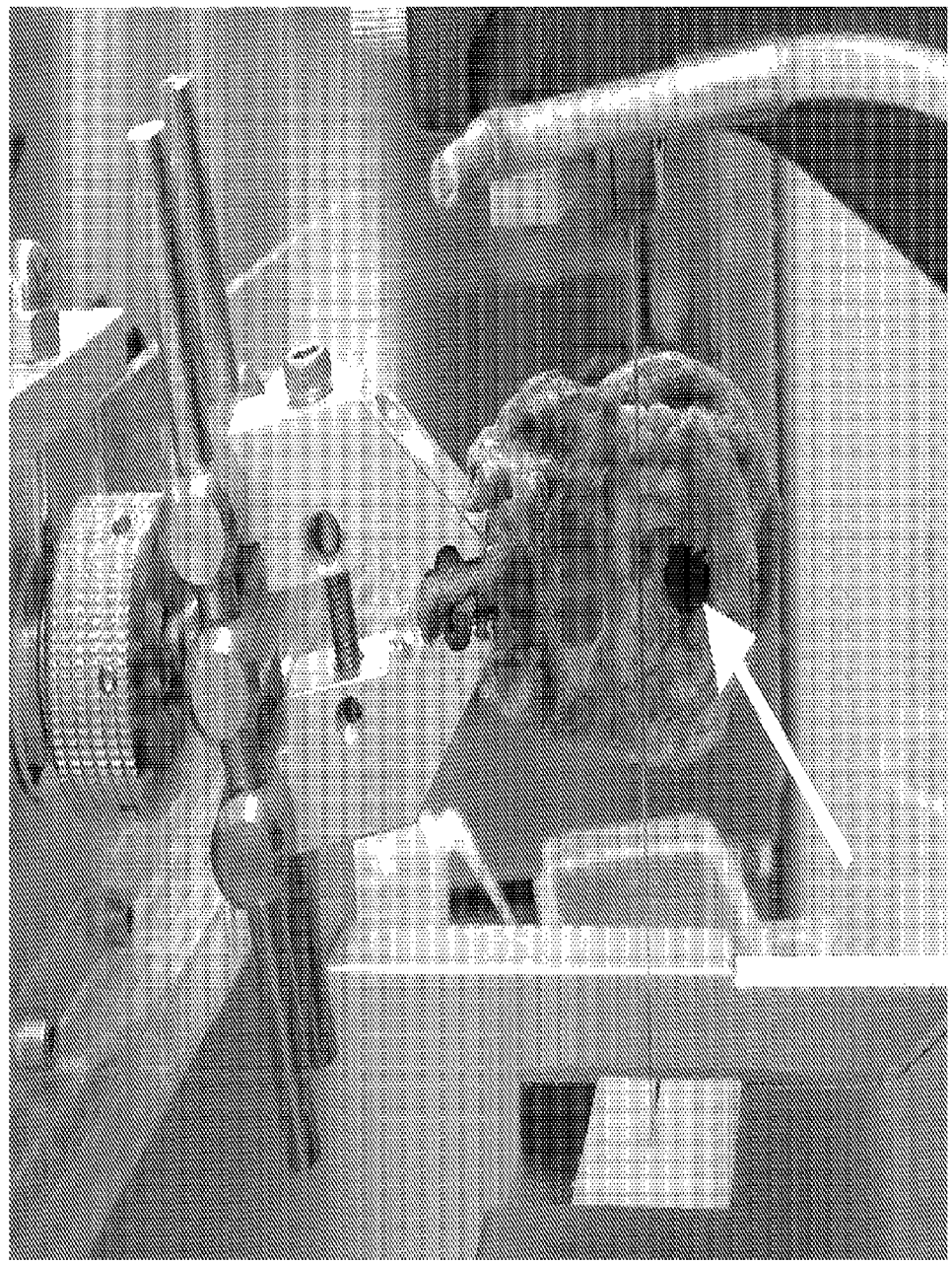
FIG. 17 depicts an image of coronal slots posterior to a cylindrical hole and sagittal slots lateral to the cylindrical hole, in either or both directions.

Nine human cadaveric vertebrae were obtained from three female donors (Table 5). In each vertebra, a flat-bottom cylindrical hole was created in the vertebral body, entering through the superior face and to a depth of about 75% of the vertebral body height, using a 6.35 mm diameter (for the C7 and T1 vertebrae) or a 9.53 mm diameter (for the T5, T6, T11 and T12 vertebrae) drill bit and end mill bit. This hole would allow for the placement of a preformed cylinder of radioactive bone cement within the vertebral body during the subsequent laboratory experiment. The dimensions of each cylindrical hole were measured and recorded, and an aluminum mold was fabricated for molding appropriately sized cylinders of radioactive bone cement. A precision band saw with a diamond-coated blade (EXAKT 300CP, EXAKT Technologies, Inc., Oklahoma City, Okla., USA) was then used to create 0.25 mm thick slots within the vertebral body for placement of radiochromic film. These slots were approximately parallel to the axis of the cylindrical hole and oriented in the coronal and sagittal planes of the vertebrae. At their closest point, the slots were about 0.1 mm to 7 mm from the surface of the cylindrical hole, as measured on the superior face of the vertebral body. Coronal slots were posterior to the cylindrical hole, intended to measure the dose approaching the spinal canal. Sagittal slots were lateral to the cylindrical hole, in either or both directions (FIG. 17; arrow indicates cylindrical hole for placement of radioactive cement cylinder).

TABLE 5

| Donor | Age (years) | Cause of death | Vertebral specimens (study ID) |
|---|---|---|---|
| 1 | 69 | Anoxic encephalopathy | T1 (0101), T6 (0106), T12 (0112) |
| 2 | 80 | Cardiac arrest | T1 (0201), T5 (0205), T12 (0212) |
| 3 | 84 | Artherosclerotic vascular disease | C7 (0300), T4 (0304), T11 (0311) |

A silicone mold was created around the posterior element of each vertebra to hold the specimens in place. CT scans were obtained with the vertebrae immersed in water to minimize streak artifacts (GE Discovery VCT PET/CT, standard reconstruction, 80 kVp, 280 mAs). To enable accurate measurement of apparent wet bone mineral density (BMD), the vertebrae from donor 1 were scanned with 0.625 mm pixels and the vertebrae from donors 2 and 3 were scanned with 0.3125 mm pixels. The vertebrae from donors 2 and 3 were scanned with smaller pixels in an effort to refine model resolution. However, this did not have the desired effect, and the CT data were later reconstructed to provide 0.625 mm pixels. A plastic calibration phantom containing chambers that were radiographically equivalent to 0, 75, and 150 mg cm$^{-3}$ of calcium hydroxyapatite in water (Image Analysis Inc., Columbia, Ky.) was included in each scan. To minimize the size of the subsequent Monte Carlo model while maintaining adequate resolution, CT scans were obtained with contiguous 1.25 mm thick slices.

Figure 18:
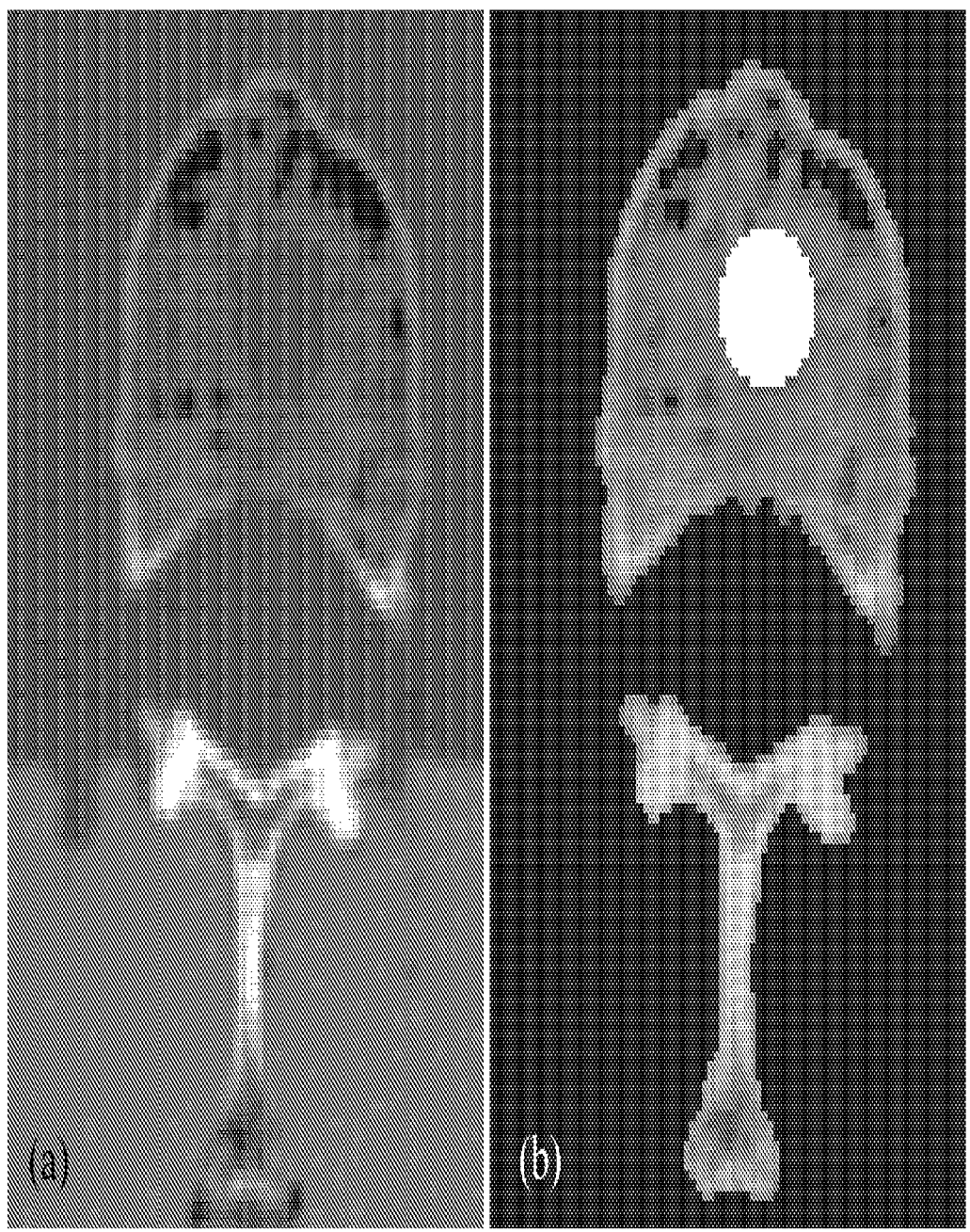
FIG. 18 depicts images showing transverse cross-sections of a modeled vertebra.

In-house software was developed and used to transform the CT scan data for each vertebra into a Monte Carlo N-Particle (MCNP) model (X-5 Monte Carlo Team 2005) consisting of a three-dimensional rectangular lattice of 0.625 mm×0.625 mm×1.25 mm voxels (FIG. 18). Bone in the model was represented by as many as thirty bone material definitions, with both trabecular and cortical bone represented by a spectrum of complementary volume fractions of bone marrow and solid cortical bone, ranging from 100% bone marrow to 100% solid cortical bone. Each voxel of bone was assigned a bone material (i.e. one of the thirty bone volume fractions) by converting its quantitative CT density ($\rho_{QCT}$, g cm$^{-3}$) to ash density ($\rho_{ash}$, g cm$^{-3}$) ($\rho_{ash}$=0.0633+ 0.887$\rho_{QCT}$, r=0.997), and then converting apparent wet BMD ($\rho_{wet}$, g cm$^3$) ($\rho_{wet}$=1.79$\rho_{ash}$+0.0119, r=0.992). Then, using the rule of mixtures, the real density of the bone tissue plus marrow was calculated by adding the density of the complementary volume fraction of marrow to apparent wet BMD. The atomic composition of each bone material was also calculated using the rule of mixtures, where the atomic compositions of the bone (H: 3.4%, C: 15.5%, N: 4.2%, O: 43.5%, Na: 0.1%, Mg: 0.2%, P: 10.3%, S: 0.1%, Ca: 22.5%) and marrow (H: 11.5%, C: 64.4%, N: 0.7%, O: 23.1%, Na: 0.1%, S: 0.1%, Ca: 0.1%) volume fractions were given by prior studies. Since the vertebrae were not immersed in water during the subsequent laboratory experiment, all voxels that were outside the bone were assigned the density and atomic composition of air. The cylindrical hole that was previously created within each vertebral body was identified on the CT scans and the constituent voxels within that hole were assigned the properties of Parallax® PMMA bone cement (ArthroCare Corp., Sunnyvale, Calif., USA) (FIG. 18). FIG. 18 shows a transverse cross-section of a modeled vertebra. The cylindrical drill hole is apparent in (a) the CT scan image and was modeled as a volume of radioactive bone cement (white circle) in (b) the MCNP model. A phosphorus-32 (P-32) radionuclide source was modeled as uniformly distributed within all bone cement voxels, with a complete energy spectrum from medical internal radiation dose (MIRD) data. P-32 is an ideal radionuclide for radioactive bone cement due to its high-energy beta emissions (maximum: 1.71 MeV), clinically relevant half-life (14.3 days), and prior use as a radiopharmaceutical for pain palliation in patients with bone metastases.

Each voxel in the model included a pulse-height energy distribution tally, and thirty million particle histories were simulated with Monte Carlo N-Particle eXtended v. 2.5.0 (MCNPX, Los Alamos National Laboratory, Los Alamos, N. Mex., USA, 2005) using the default cross-sections. The presence of the cement within the model ensured that all self-shielding effects were accurately represented. For each voxel tally, the energy deposited per source particle was used to calculate the dose rate per unit of initial activity, hereafter referred to simply as 'dose rate', with units of Gy/h/mCi. Matlab R2006a (The Mathworks, Inc., Natick, Mass., USA) was first used to visually confirm that the dose distributions were axisymmetric by generating isodose contour lines for three dose rates within the vertebral body: 0.3 Gy/h/mCi, 0.5 Gy/h/mCi and 2 Gy/h/mCi. Once confirmed to be axisymmetric, the dose distribution for each specimen was characterized by a single radial depth-dose curve, i.e. an exponential curve of dose rate versus radial distance from the surface of the radioactive cement. To minimize local effects, the radial depth-dose curve was averaged over four radial directions (anterior, posterior, left lateral, right lateral) within each of three consecutive transverse planes near the center of the cylinder of cement. Tally results were assumed to be at the center of each voxel. To ensure adequate precision of the model data, the predicted radial depth-dose curves were calculated using only those tallies with a relative error (X-5 Monte Carlo Team 2005) less than 0.05.

The dose distribution in each vertebra was measured experimentally using radiochromic film, a radiation dosimetry tool that consists of a thin active layer of monomeric molecules sandwiched between two thin polyester sheets. The monomeric molecules polymerize upon exposure to ionizing radiation, resulting in a color change to blue that is dependent on the absorbed dose of the film. In this study, Gafchromic EBT radiochromic film (Lot #47277-061, Exp. Date October 2009, International Specialty Products, Wayne, N.J., USA) was selected for its ease of use, high spatial resolution, and electron energy- and dose-rate-independent response. Dose calibration was performed by irradiating 27 pieces of the film at doses of 0-15 Gy using a 12 MeV electron beam produced by a Clinac 21-EX linear accelerator (Varian Medical Systems, Inc., Palo Alto, Calif., USA), calibrated according to the TG-51 protocol. The 12 MeV electron beam was selected because it has a broad depth of dose maximum, which minimizes the effect of positioning uncertainties in the calibration setup. Each piece of film was placed at the depth of dose maximum (dmax=28 mm) in a solid water phantom and irradiated under calibration conditions of 100 cm source-to-surface distance and 15×15 cm$^2$ size electron applicator. Each piece of film was then scanned on an Epson VX700 flatbed scanner (Epson America, Inc., Long Beach, Calif., USA) at 122 dpi with the film in landscape orientation (with respect to the original, uncut sheets) relative to the axis of the scanner bed. Red channel pixel intensity was converted to optical density, and the average optical density within a 100 pixel×200 pixel region in the center of each film was calculated. The net optical density (netOD) for each film was calculated relative to the optical density of the unexposed film, and plotted against the corresponding dose level for that film. A calibration equation was described using a third-order polynomial function and used to determine the radiochromic film dose rates in the experiment.

For the experiment, P-32 was mixed with Parallax® bone cement powder and shaken to ensure a uniform distribution of the radionuclide within the cement powder. The liquid monomer was added and the cement was mixed according to the manufacturer's recommended procedure, creating radioactive bone cement. The cement was prepared under the approval and guidance of the Environmental Health and Safety office at the University of California, Irvine, with all steps taken to minimize the risk of harmful radiation exposure. The radioactive cement was then injected into the aluminum molds that were fabricated previously for making cement cylinders, after which the cured radioactive cement cylinders were inserted into the cylindrical hole of the appropriate vertebral body. The total initial activity contained within each cylinder and implanted into each specimen was calculated from the manufacturer's assayed level of activity, after accounting for decay from the assay date to the date of the experiment, and ranged from 0.062 mCi (2.294 MBq) to 0.36 mCi (13.32 MBq), depending on the size of each implanted cylinder.

After the creation of the cylindrical specimens, the excess radioactive cement was injected into a plastic tube (6 cm length, 5 mm inner diameter, 0.7 mm wall thickness), allowed to cure, and placed directly on top of a piece of radiochromic film for 24 hours. The exposed radiochromic film was then scanned using the procedures described previously. The uniformity of the dose distribution and, therefore, the uniformity of the P-32 distribution within the cement, was then evaluated by calculating the standard deviation as a percentage of the mean of the dose rate along a straight line on the axis of the tube.

Figure 19:
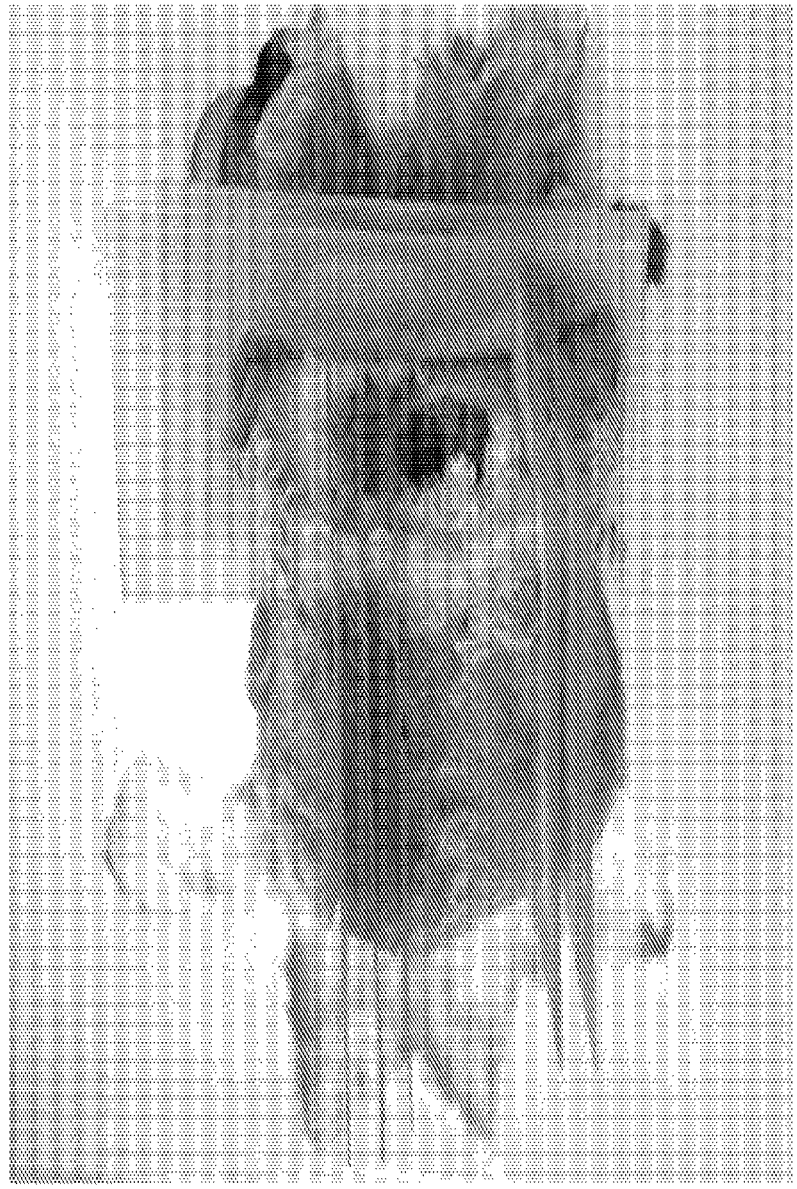
FIG. 19 is an image showing pieces of radiochromic film cut to size, labeled and placed within the coronal and sagittal slots that had been previously cut in the vertebral body.

Pieces of radiochromic film that had been cut to size and labeled were placed within the coronal and sagittal slots that had been previously cut in the vertebral body (FIG. 19). The exposure time for each piece of film was in the range of 6-168 h, selected to maximize contrast while preventing overexposure, given the expected dose rate at each film location. When one piece of film was removed from the vertebral body, a replacement scrap piece was inserted in its place to maintain the attenuation characteristic across the plane of the film. At the conclusion of the experiment, the exposed film pieces were scanned as described previously and the experimental dose (dose over the experimental exposure period) measured by each piece of film was quantified using the calibration equation obtained previously.

The maximum experimental dose measured in any pixel on each piece of film was determined and divided by the corresponding exposure time and initial activity to calculate the maximum experimental dose rate (Gy/h/mCi) for each piece of film. Analogous to the MCNP-predicted dose distribution, the measured dose distribution for each specimen was assumed to be axisymmetric about the radioactive cement implant and was characterized by a radial depth-dose curve. For each vertebra considered separately, the measured radial depth-dose curve was generated by plotting the maximum dose rate for each piece of film within that vertebra versus the shortest radial distance from the surface of the radioactive cement to the corresponding film.

Accuracy of the MCNP models was evaluated by comparing the predicted and measured dose distributions. For radial distances of 1 mm, 2 mm, and 3 mm on the predicted depth-dose curve, the absolute value of the horizontal distance between the predicted and measured curves was calculated for each specimen and averaged across all specimens. This approach is recommended by the International Commission on Radiation Units and Measurements (1987) for high-gradient regions of depth-dose curves. In the low-gradient region of the depth-dose curves, the vertical difference (measured dose rate minus predicted dose rate) between the depth-dose curves at radial distances of 5 mm and 6 mm was calculated for each specimen and averaged across all specimens.

As a more rigorous evaluation of model accuracy, the predicted and measured dose distributions were evaluated for agreement within the experimental uncertainty. Since dose rate decreased exponentially with distance, regression analysis (SigmaStat, San Jose, Calif., USA) was used to compute log-linear depth-dose curves, i.e. linear relationships between ln(dose rate) and radial distance, for the predicted and measured data for each specimen. Additionally, the 95% confidence interval (CI) of the measured log-linear depth-dose curve was determined. The models were deemed to be accurate when the dose distributions agreed within the experimental uncertainty, i.e. when the predicted log-linear depth-dose curve fell within the 95% CI of the measured log-linear depth-dose curve.

A potential source of uncertainty is related to a loss of marrow from within the vertebral body during specimen preparation. The modeled bone materials were based on the CT densities of bone that contained marrow or water within the trabecular pores, since marrow may have been displaced from the vertebral body when the vertebrae were immersed in water for CT scanning. However, since the vertebrae were removed from the water after CT scanning, the marrow that had been displaced by water may have been replaced by air during the experiment, potentially causing the experimental condition to be modeled somewhat inaccurately. To determine whether model inaccuracy could be attributed to this source of uncertainty, models that were not accurate according to the above definition were modified by reducing the density of the bone marrow constituent of the bone material definitions until the predicted and measured dose distributions agreed within the experimental uncertainty. This reduction in bone marrow density was intended to represent a reduced quantity of marrow within each specimen.

Figure 20:
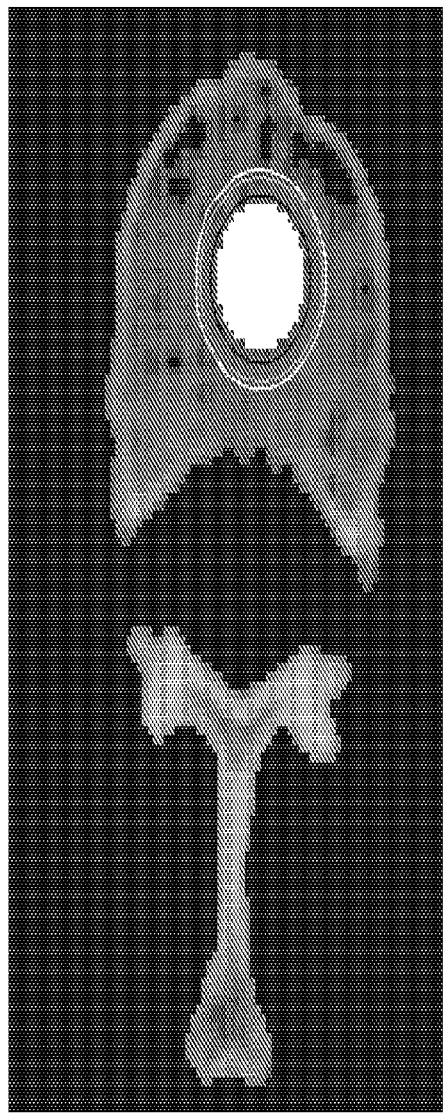
FIG. 20 is an image illustrating that an isodose contour plot of the predicted dose distribution exhibits an axisymmetric distribution about the cylindrical radioactive cement source.

Specimen 0201 (Table 5, row 2, column 4) was destroyed during experiment handling, leaving eight specimens for evaluation. The isodose contour plot of the predicted dose distribution within each vertebral body confirmed an axisymmetric distribution about the cylindrical radioactive cement source and rapidly decreasing dose with increasing radial distance from the cement surface, as shown in FIG. 20. Isodose lines represent constant dose rates of 0.3 Gy/h/mCi, 0.5 Gy/h/mCi, and 1.9 Gy/h/mCi, from the largest to the smallest circles.

Figure 21:
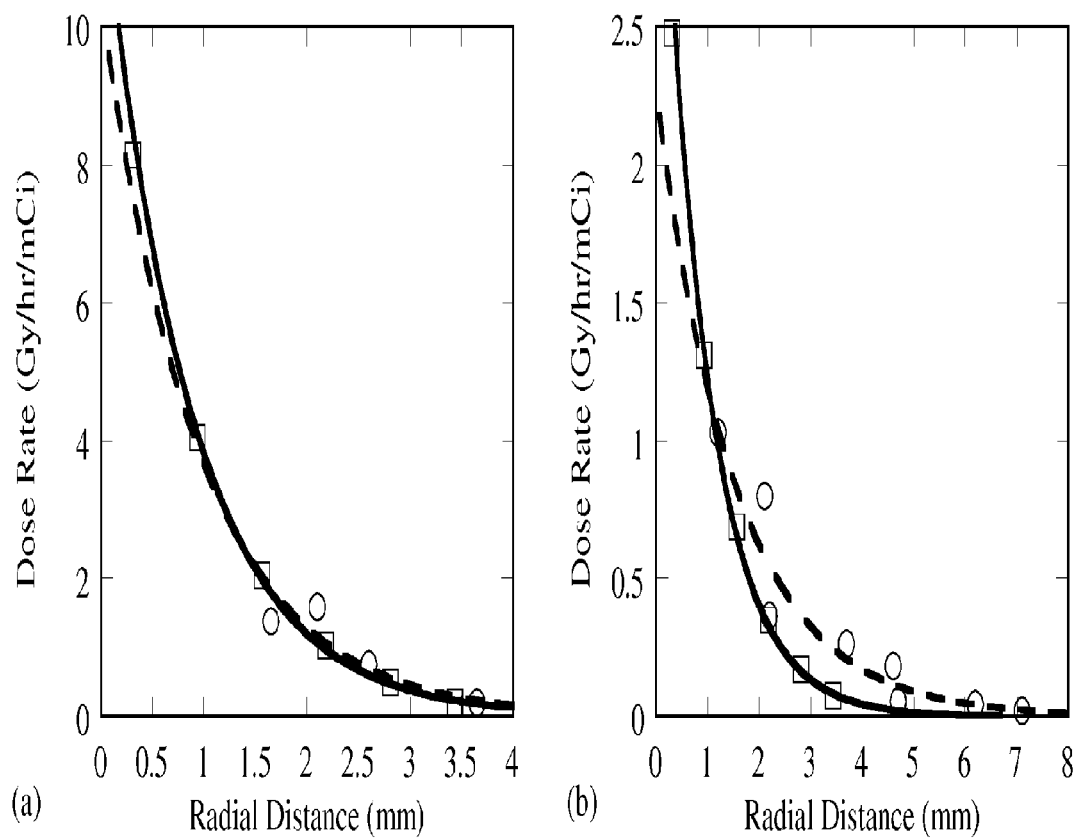
FIG. 21 depicts plots of predicted and measured radial depth-dose curves for two different specimens.

In the high-gradient region of the depth-dose curves, the average absolute value of the horizontal distance from the predicted curve to the measured curve was 0.27, 0.49 and 0.90 mm at radial distances of 1, 2, and 3 mm, respectively, from the surface of the radioactive cement source. In the low-gradient region of the depth-dose curves, the average vertical difference from the predicted depth-dose curve to the measured depth-dose curve was 0.055 and 0.033 Gy/h/mCi at 5 and 6 mm, respectively (FIG. 21). FIG. 21(a) illustrates predicted (squares, solid line) and measured (circles, dashed line) radial depth-dose curves for specimen 0101, and FIG. 21(b) predicted (squares, solid line) and measured (circles, dashed line) radial depth-dose curves for specimen 0212.

Figure 22:
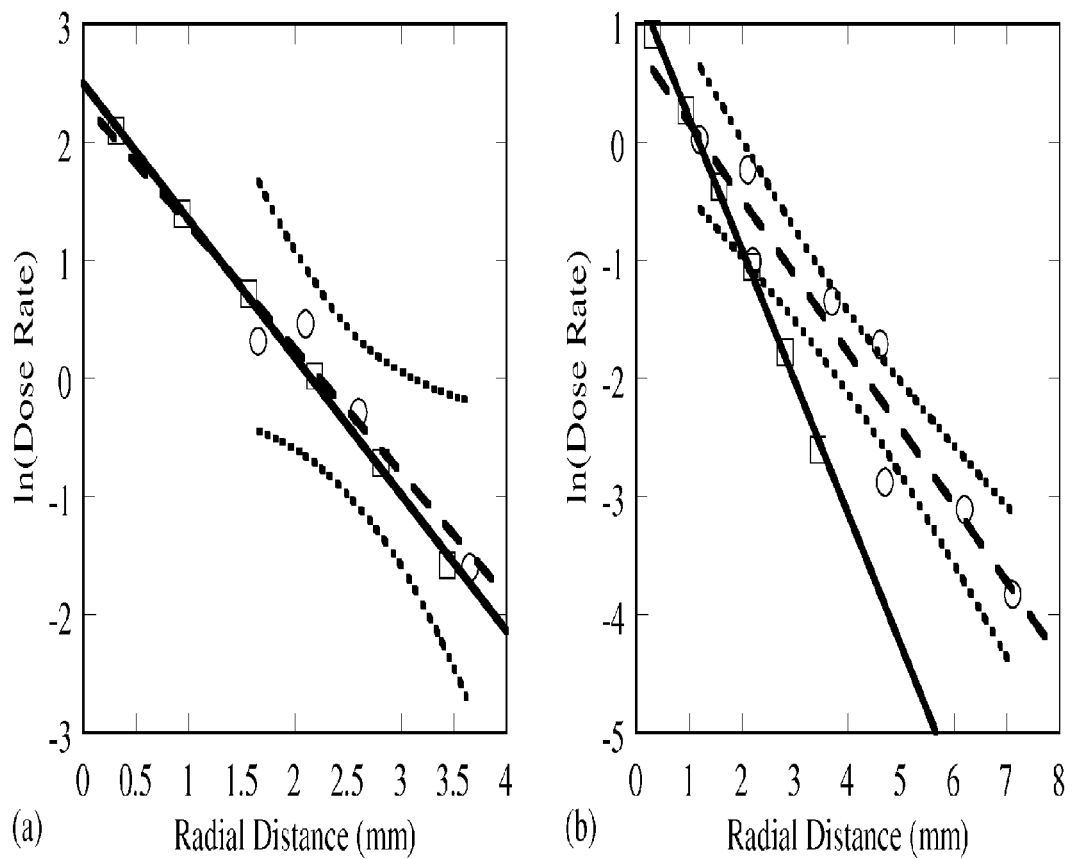
FIG. 22 depicts predicted and measured log-linear depth-dose curves for the specimens.
Figure 23:
FIG. 23 is an image illustrating open trabecular pores in one specimen, a result of marrow loss that occurred during experimental specimen preparation.
Figure 24:
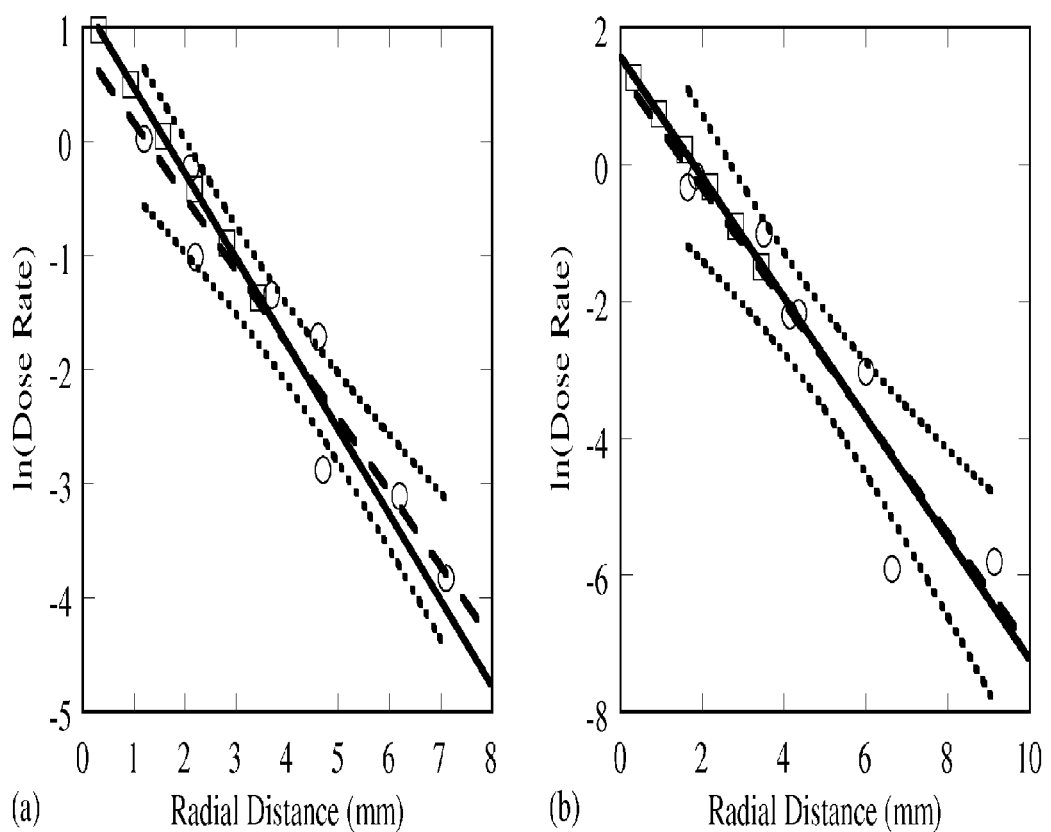
FIG. 24 depicts predicted and measured log-linear depth-dose curves for modified MCNP models of two specimens

FIG. 22 illustrates predicted (squares, solid line) and measured (circles, dashed line) log-linear depth-dose curves for specimens (a) 0101 and (b) 0212. For four of the eight specimens, the predicted and measured dose distributions agreed within the experimental uncertainty over the entire radial distance range (FIG. 22(a)). For the remaining four specimens, the predicted log-linear depth-dose curve fell within the 95% CI of the measured log-linear depth-dose curve for distances up to ~2 mm, but consistently understated the measured dose rate at points far from the cement surface (i.e., at distances greater than ~2 mm) (FIG. 22(b)). The bone marrow density in these models was decreased by 20-40% to account for an absence of marrow that was observed in the trabecular pores of some specimens, as illustrated by a post-experiment photograph (FIG. 23) showing open trabecular pores resulting from marrow loss during the experimental specimen preparation procedure. This resulted in predicted and measured dose distributions that agreed within the experimental uncertainty, as illustrated by FIG. 24 which shows predicted (squares, solid line) and measured (circles, dashed line) log-linear depth-dose curves for the modified MCNP models for specimens (a) 0212 (40% marrow reduction) and (b) 0311 (20% marrow reduction). For all four modified MCNP models, decreasing the bone marrow density by 20-40% resulted in dose distributions that agreed within the experimental uncertainty.

The above-described radiation transport modeling method can automatically generate anatomically correct, patient-specific, CT scan-based MCNP models of vertebrae containing radioactive bone cement. The accuracy of the modeling method was evaluated by comparing dose distributions calculated by the models to those measured in human cadaveric vertebral bodies in which radioactive bone cement had been implanted. The results presented indicate that these models can predict measured dose distributions with clinically relevant accuracy and within the experimental uncertainty, making this modeling method a useful analytical tool for developing radioactive bone cement to treat spinal metastases.

The radiochromic film used to evaluate the uniformity of the distribution of P-32 within the radioactive cement revealed that the standard deviation of the dose rate along the axis of the cement-filled tube was 0.33% of the mean. This result indicates that the P-32 was sufficiently mixed within the radioactive cement, thereby validating the uniform distribution of radionuclide within the MCNP cement voxels.

In the high-gradient region of the depth-dose curves, the average horizontal distances between the predicted and measured radial depth-dose curves can be compared to the results of a first study, that measured differences of 0.2-0.5 mm, and a second study, that measured differences of 0.5-0.7 mm (in both of these studies, it was not stated whether these are absolute or signed values). Our average absolute differences of 0.27-0.90 mm are approximately the same as those of previous studies, a notable result considering the heterogeneity and inherent complexity of cadaveric vertebral bodies compared to the homogeneous solid water and "tissue-substitute" plastic phantoms used previously. Our results indicate that if the MCNP models were used to predict the dose rate within the vertebral body at a radial distance of, e.g., 2 mm from the surface of the radioactive cement, the actual radial distance at which that dose rate would occur might differ by about 0.2 mm. This difference is much lower than the 2-4 mm criteria of acceptability established as the benchmarks for EBRT treatment planning accuracy.

In the low-gradient region of the depth-dose curves, the average vertical differences between the predicted and measured radial depth-dose curves indicate that if the MCNP models were used to predict the dose rate within the vertebral body at a radial distance of, e.g., 6 mm from the surface of the radioactive cement, the actual dose rate at that distance might be about 0.033 Gy/h/mCi greater than the model prediction. For the levels of activity that were implanted in this study, this difference corresponds to a predicted lifetime dose of 0.28-1.6 Gy when the actual lifetime dose would be 1.3-7.5 Gy. Depending on the location of the radioactive bone cement within the vertebral body, this region of the depth-dose curve may be used for dosimetry of the spinal cord. In that case, this dose underestimation might be important, depending on the patient's history of spinal cord irradiation (e.g., prior EBRT) and the volume of cord affected, among other factors. This type of information will guide the development of clinical treatment planning for using radioactive bone cement to treat spinal metastases.

It is noteworthy that only tallies with a relative error less than 0.05 were analyzed, and the MCNP-predicted radial depth-dose curves were extrapolated to radial distances beyond the range of the tally results to which they were fit. Although this extrapolation may have limited the accuracy of the predicted dose rates in the low-gradient region of the depth-dose curves, this approach was necessary to ensure that the depth-dose curves were based on tallies that had an optimal relative error. A number of variance reduction techniques in MCNP may be used to extend the radial distance at which optimal tally results can be obtained. However, that was beyond the scope of this study.

For the more rigorous evaluation of model accuracy, the 95% CI of the measured log-linear depth-dose curve reflected the uncertainty associated with dose measurements using radiochromic film, which can be high as ±15%, as well as uncertainty in the radial distance measurements used to compute the depth-dose curve. Models for four of the specimens predicted the measured dose distribution within this uncertainty without modification. For the remaining four specimens, reducing the marrow density showed that the understatement of dose rate by the unmodified models could be attributed to a loss of bone marrow from the vertebral body. The volume of marrow lost from each specimen could not be quantified, and marrow loss was neither uniform within each specimen nor consistent across all specimens. However, visual observation indicated that marrow loss generally seemed to be most extensive in the specimens that required model modification. Thus, although the magnitudes of the marrow density reductions are somewhat arbitrary, the agreement between the predicted and measured dose distributions after adjusting for marrow loss, and the agreement of the other four models even without modification, demonstrates that the modeling method is fundamentally sound. Hence, in intact vertebrae or in experiments that minimize marrow loss, we can expect that this modeling method can be used to predict dose distributions in vertebrae containing radioactive bone cement.

This study employed P-32 as the radionuclide for radioactive bone cement. A number of other radionuclides might be used (and potentially in combination), such as strontium-89 (Sr-89), yttrium-90 (Y-90) and rhenium-188 (Re-188). However, alternative radionuclides and combinations thereof may produce very different dose distributions than those evaluated in this study, since the energy spectrum and particle emission type may be much different from P-32. The accuracy of MCNP models for radionuclides other than P-32 can be evaluated in a manner similar to this study.

The MCNP modeling method was evaluated using cylindrical radioactive bone cement specimens. However, clinical vertebroplasty may involve cement distributions that are more complex and involve cement-bone interdigitation. The cylindrical cement specimens enabled a repeatable, practical experiment in which the geometry of the radioactive source could be accurately modeled from CT scan images. This experiment allowed the MCNP models to be reliably evaluated with respect to radiation transport through mixtures of bone and marrow, as well as through the radioactive cement itself. The agreement between the predicted and measured dose distributions indicates that the fundamental principles underlying the CT scan-based modeling method are sound, and more sophisticated models involving clinically relevant cement distributions can be developed and analyzed.

With its fundamental principles now established, the CT scan-based MCNP modeling method presented in this study can be used as an analytical tool for use in the development of using radioactive bone cement to treat spinal metastases. Use of the modeling method will enable a systematic analysis of many issues, including the distance from the cement at which a therapeutic dose can be delivered to the bone; the extent to which the implanted activity, bone density, and presence of lesions change this distance; and the resulting maximum volume of bone/tumor that can be treated. The models will also enable estimates of the absorbed dose in the adjacent bone and the cement itself, factors that might potentially lead to degradation of material properties. These issues, among many others, will determine the feasibility of using radioactive bone cement to treat spinal metastases and will help to define guidelines for its clinical use.

A radiation transport modeling method was presented to calculate dose distributions within vertebrae containing radioactive bone cement. This study marked the first-ever attempt to measure such dose distributions, and the accuracy of the modeling method was evaluated by comparing model-predicted dose distributions to those measured experimentally. Differences between the high-gradient regions of the predicted and measured radial depth-dose curves were comparable to differences evaluated using homogenous plastic phantoms and are likely to be clinically insignificant. Differences in the low-gradient regions of the depth-dose curves may be important in situations involving prior spinal irradiation, and this information will guide the development of clinical treatment planning for using radioactive bone cement to treat spinal metastases. Using a more rigorous evaluation of model accuracy, models for four of the specimens predicted the measured dose distribution within the experimental uncertainty without modification. For the remaining four specimens, reducing the marrow density showed that when marrow loss is accounted for, this modeling method can accurately predict dose distributions in vertebrae containing radioactive bone cement. This modeling method is a valuable tool for development of radioactive bone cement as an alternative to the conventional two-step approach to treating spinal metastases.

The following algorithm may be used for treatment planning, which includes determining the distance from the surface of the cement to tissues that will be spared (e.g., neurologic tissues), the prescribed activity concentration, the approximate location(s) at which the cement may be injected, and the planned dose distribution in the target tissues and structures to be spared. The physician first identifies the lesions and tissues to be spared on images from MRI, CT or other imaging modalities that provide accurate measurement of distances to the key anatomical structures. The physician then specifies maximum tolerable dose to each tissue to be spared. For example, 45 Gy to the spinal cord.

Figure 25:
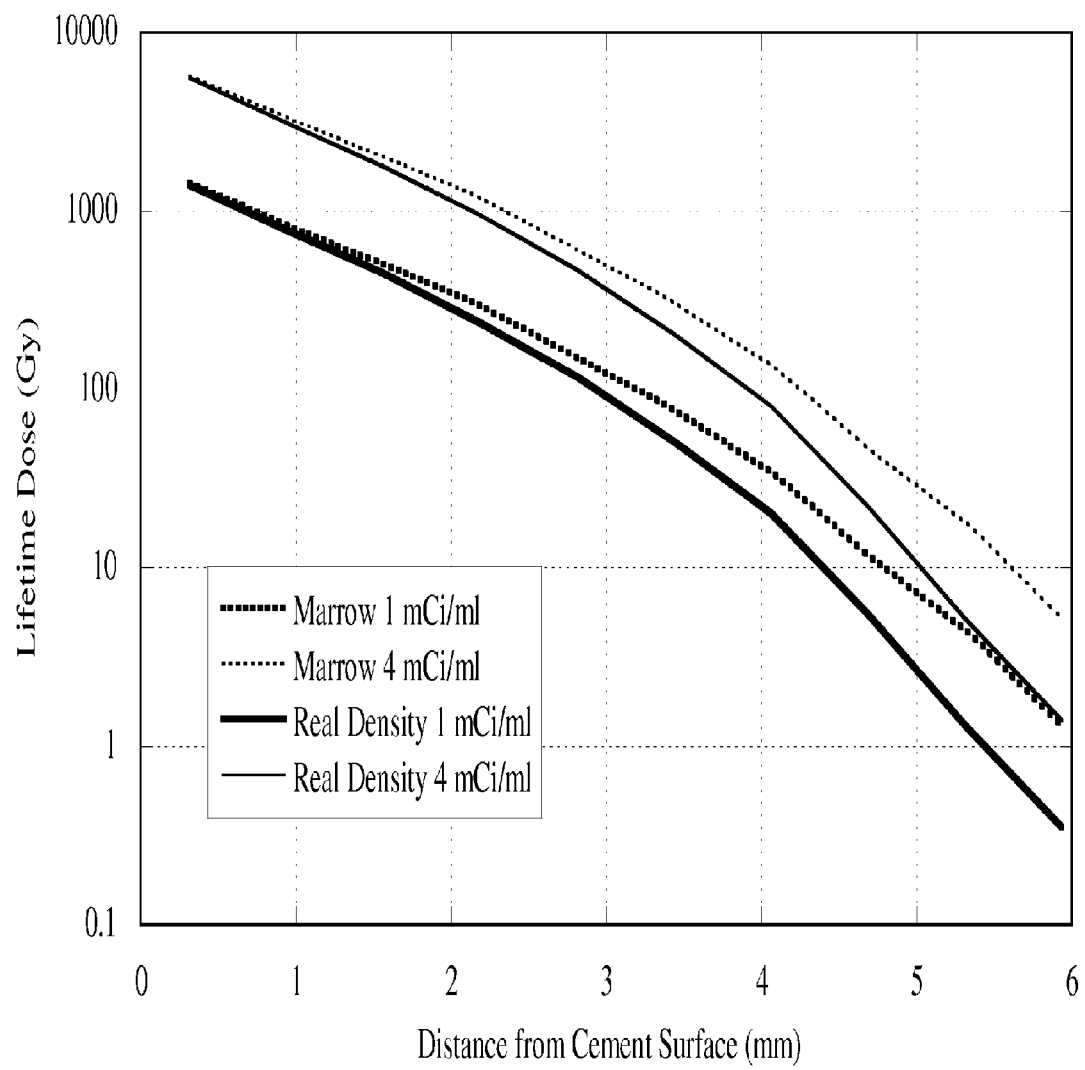
FIG. 25 shows depth-dose curves for a vertebral body with a 15-mm cubic volume of radioactive bone cement indicate that the dose rapidly decreases with distance from the surface of the cement, and the difference between curves for a typical bone density and for bone marrow.

From FIG. 25 or an equivalent table or website that will be available to the physician, and assuming the maximum tolerable dose to the tissues, the physician determines the minimum distance from the cement surface to each tissue for each activity concentration. A "conservative" approach may be used to ensure safety. Thus, in cases with lytic lesions, the curves for pure marrow may be used to determine this distance. For example, for 1 mCi/ml, a distance of at least 4 mm would provide less than 45 Gy to the spinal cord, regardless of bone density. For 4 mCi/ml, a distance of about 5 mm between the cement surface and the spinal cord would be acceptable. Because each distance will be associated with an uncertainty due to the uncertainty in the computed distance (based on the dosimetry model validation experiments), a margin of safety may be built into the tools to be used by the physician. If there is a substantial shell of cortical bone between the cement and the tissue to be spared, the physician may wish to account for the protective effect of the cortex, which will reduce the dose to the tissue to be spared. Such a factor may be included in the tools for the physician, which will allow a greater dose to be delivered to the target. Additional dosimetry curves for bone with blastic lesions will allow the physician to determine the effect of blastic lesions on the dose to the tissues to be spared. These curves will also tell the physician the extent to which the particular activity concentration will allow the radiation to penetrate through the dense bone.

FIG. 25 depicts log-linear depth-dose curves for the vertebral body with a 15-mm cubic volume of radioactive bone cement which indicate that the dose rapidly decreases with distance from the surface of the cement. Depth-dose curves are shown for the actual vertebral bone density (solid lines) and for zero bone density (100% marrow) (dotted lines), for initial activity concentrations of 1 mCi/ml (thick lines) and 4 mCi/ml (thin lines). Other activity concentrations that may be available (2 and 3 mCi/ml) are not shown for clarity. For activity concentrations of 1 mCi/ml to 4 mCi/ml, the distance at which a lifetime dose of at least 10 Gy is delivered increases by less than 0.6 mm when the bone density changes from the actual density to that of pure marrow.

Figure 26:
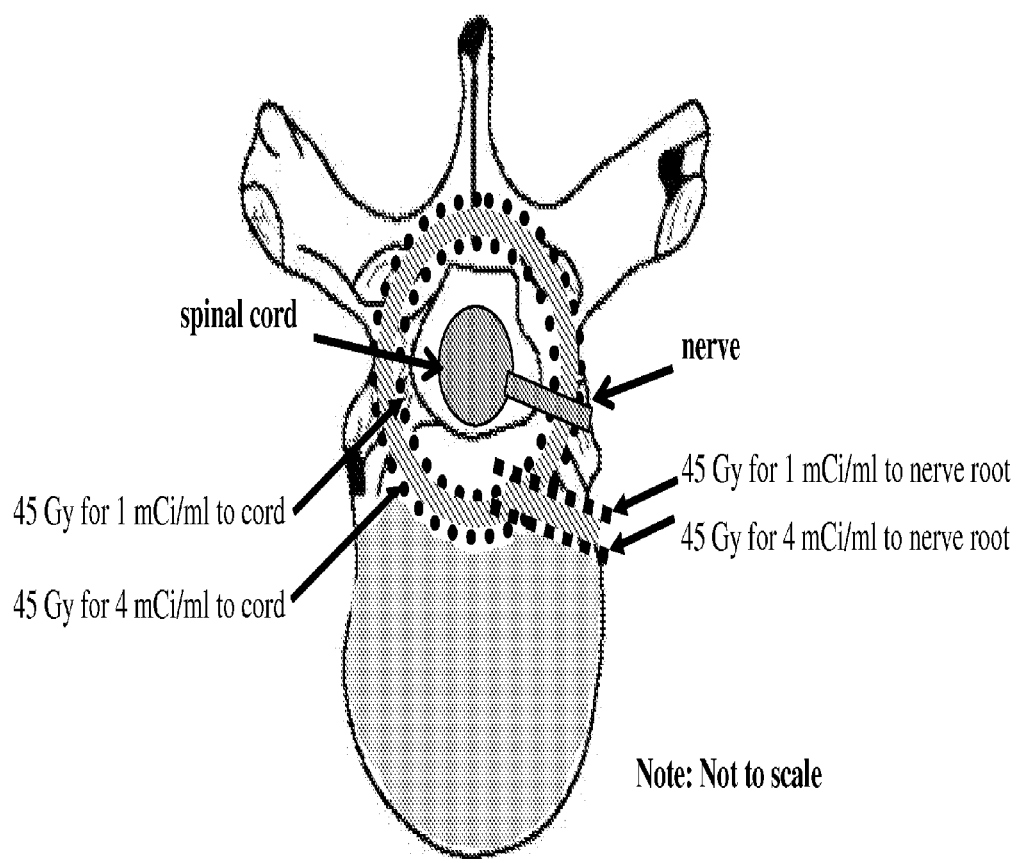
FIG. 26 is a schematic of dosimetry procedure to be performed using transverse images through the vertebral body.

FIG. 26 illustrates a schematic of dosimetry procedure to be performed using transverse images through the vertebral body. Only one nerve root is shown for clarity.

Once the physician determines the distance between the tissue to be spared and the cement surface for each tissue to be spared (e.g., each nerve root and the spinal cord), the physician marks this distance for each activity concentration on at least one transverse image through the vertebra (as shown in FIG. 26 by the dotted lines). If only one image is used, it may be the one that results in the most conservative treatment plan, which would be the image in which the sensitive structure(s) are closest to the target.

The result of the previous step will then determine the activity concentration(s) that can safely be used. If the tumor lies beyond all marked distances for an activity concentration of 4 mCi/ml (e.g., in the speckled area in FIG. 26), then an activity concentration of 4 mCi/ml can be prescribed, and the cement can be safely injected to within the line labeled " . . . for 4 mCi/ml." If the tumor lies completely in the area between the 1 mCi/ml and 4 mCi/ml lines (hatched area in FIG. 26), the lower activity should be used, and cement can be safely injected to within the 1 mCi/ml line. If a tumor or portion of a tumor falls within the marked distance for the lowest activity concentration, the cement may only be injected up to that marked distance. The tumor will still receive a substantial radiation dose, but that dose will decrease with distance as shown in FIG. 25, and the tissues to be spared will not be harmed.

What is claimed:

1. A method of placing a mixture for treating a target tissue in a patient, the method comprising:
   providing a mixture comprising a matrix material and a radioisotope, wherein the radioisotope has an activity concentration in said mixture;
   based on (a) the activity concentration of the radioisotope in the mixture, and (b) a dose of radiation to be delivered to the target tissue by the radioisotope, determining a distance between the target tissue and a surface of the mixture; and
   placing the mixture in the patient with a closest surface of the mixture at the determined distance, wherein the mixture is configured such that, when the mixture is at the determined distance away from the target tissue, the mixture delivers substantially the dose to the target tissue independently of a total volume of the mixture placed in the patient.

2. The method of claim 1, wherein the mixture is configured such that, when the mixture is placed in the patient, only emissions from the radioisotope within about 2.5 mm of the closest surface reach the target tissue.

3. The method of claim 1, wherein the mixture is configured such that, when the mixture is placed in the patient, only emissions from the radioisotope within about 5 mm of the closest surface of the mixture reach the target tissue.

4. The method of claim 1, further comprising mixing the radioisotope with the matrix material.

5. The method of claim 1, further comprising determining an amount of the radioisotope and an amount of the matrix material to be mixed.

6. The method of claim 1, further comprising forming the mixture into a shape comprising at least one selected from the group consisting of a cylinder, a sphere, a cube, and combinations thereof.

7. The method of claim 1, wherein the matrix material comprises bone cement.

8. The method of claim 1, wherein the radioisotope emits gamma rays.

9. The method of claim 8, wherein the gamma-emitting radioisotope comprises at least one of Rhenium, Iridium, Tantalum, Tungsten, Gold, and a Lanthanide series element.

10. The method of claim 1, wherein the matrix material comprises at least one of Rhenium, Iridium, Tantalum, Tungsten, Gold, and a Lanthanide series element.

11. The method of claim 1, wherein the mixture is configured such that, when the mixture is placed in the patient, only emissions from the radioisotope within about 1.9 mm of the closest surface reach the target tissue.

12. The method of claim 1, wherein the radioisotope comprises a beta-emitter and at least one of P-32, Y-90, and Sr-89.

13. The method of claim 1, wherein the radioisotope is a first radioisotope of a plurality of radioisotopes with a range of half-lives, wherein the matrix material comprises the plurality of radioisotopes with a range of half-lives, such that the target tissue is treated with the first radioisotope of the plurality, having a half-life shorter than another of the plurality.

14. The method of claim 1, further comprising mixing at least one of Y-90, P-32, and Sr-89 with the matrix material.

15. The method of claim 1, wherein the mixture is configured such that, when the mixture is placed in the patient, only emissions from the radioisotope within about 1.0 mm of the closest surface reach the target tissue.

16. The method of claim 1, wherein the determining is by a processor and is based on inputs, to the processor, of an indicator of the activity concentration and an indicator of the dose.

17. The method of claim 16, wherein the determining is based on a three-dimensional model generated by the processor and based on (a) the activity concentration of the radioisotope in the mixture, and (b) the dose of radiation to be delivered to the target tissue by the radioisotope.

18. The method of claim 1, wherein the distance is output by a processor.

19. The method of claim 1, wherein the activity concentration of the radioisotope in the mixture is about 4 mCi per ml.

20. The method of claim 1, wherein the mixture is configured such that, when the mixture is placed in the patient, non-target tissue about 6 mm or more from the mixture will be exposed to less than about 30 Gy.

21. The method of claim 1, wherein placing the mixture in the patient comprises placing the mixture in the vertebra of the patient.

* * * * *